US011950839B2

(12) United States Patent
Datta et al.

(10) Patent No.: US 11,950,839 B2
(45) Date of Patent: Apr. 9, 2024

(54) MULTIPLE VACUUM DEVICE FOR MEDICAL FIXTURE PLACEMENT

(71) Applicant: SD Cardiothoracic Innovations, LLC, Delaware, OH (US)

(72) Inventors: Subhajit Datta, Delaware, OH (US); John Bockbrader, Powell, OH (US); Corinne Macnichol, Columbus, OH (US)

(73) Assignee: SD Cardiothoracic Innovations, LLC, Delaware, OH (US)

(*) Notice: Subject to any disclaimer, the term of this patent is extended or adjusted under 35 U.S.C. 154(b) by 533 days.

(21) Appl. No.: 16/943,876

(22) Filed: Jul. 30, 2020

(65) Prior Publication Data
US 2022/0031388 A1 Feb. 3, 2022

(51) Int. Cl.
*A61B 18/14* (2006.01)
*A61B 17/00* (2006.01)
(Continued)

(52) U.S. Cl.
CPC ........ *A61B 18/1492* (2013.01); *A61N 1/0587* (2013.01); *A61B 2017/00292* (2013.01); *A61B 2018/00363* (2013.01); *A61B 2018/00595* (2013.01); *A61B 2018/1253* (2013.01); *A61B 2018/1412* (2013.01); *A61B 2218/007* (2013.01)

(58) Field of Classification Search
CPC ...... A61B 18/1492; A61B 2017/00292; A61B 2018/00363; A61B 2018/00595; A61B 2018/1412; A61B 2218/007; A61N 1/0587
See application file for complete search history.

(56) References Cited

U.S. PATENT DOCUMENTS 4,146,037 A 3/1979 Flynn et al.
4,271,846 A 6/1981 Little
(Continued)

FOREIGN PATENT DOCUMENTS

EP 452278 B1 11/1995
WO 9906104 2/1999
(Continued)

*Primary Examiner* — Joseph A Stoklosa
*Assistant Examiner* — Annie L Shoulders
(74) *Attorney, Agent, or Firm* — Ice Miller LLP

(57) ABSTRACT

The present invention includes devices and methods for pacing contact, lead, conduit or other medical fixture placement in tissues or organs. The invention features an articulating multiple suction foot device, comprising an inner vacuum conduit and foot slidingly contained within an outer vacuum conduit and foot, with the inner vacuum conduit and foot configured to extend beyond the outer vacuum suction foot, and to be further articulated once extended; as well as a separate tissue or waste removal vacuum assembly that extends within the inner vacuum conduit to the inner vacuum foot to remove cut tissue prior to its advancement beyond the outer vacuum suction foot. The device is configured to permit the placement foot, such as a suction foot, to articulate to a desired position with respect to the target tissue, while the pacing contact, lead, fluid conduit or other medical fixture is releasably attached to the placement foot to permit it to be released from the placement foot after stabilization on the target tissue site.

19 Claims, 35 Drawing Sheets

(51) Int. Cl.
    *A61B 18/00*     (2006.01)
    *A61N 1/05*     (2006.01)
    *A61B 18/12*     (2006.01)

(56) References Cited

U.S. PATENT DOCUMENTS

| | | | |
|---|---|---|---|
| 4,972,847 A | 11/1990 | Dutcher et al. | |
| 5,139,033 A | 8/1992 | Everett et al. | |
| 5,203,772 A | 4/1993 | Hammerslag et al. | |
| 5,254,117 A * | 10/1993 | Rigby | A61M 1/774 |
| | | | 606/49 |
| 5,342,413 A | 8/1994 | Hirschberg et al. | |
| 5,882,333 A | 3/1999 | Schaer et al. | |
| 5,902,331 A | 5/1999 | Bonner et al. | |
| 5,972,013 A | 10/1999 | Schmidt | |
| 6,132,456 A | 10/2000 | Sommer et al. | |
| 6,697,677 B2 | 2/2004 | Dahl et al. | |
| 6,868,291 B1 | 3/2005 | Bonner et al. | |
| 7,270,669 B1 | 9/2007 | Sra | |
| 7,526,342 B2 | 4/2009 | Chin et al. | |
| 7,544,197 B2 | 6/2009 | Kelsch et al. | |
| 7,890,192 B1 | 2/2011 | Kelsch et al. | |
| 7,930,040 B1 | 4/2011 | Kelsch et al. | |
| 8,317,786 B2 * | 11/2012 | Dahla | A61B 18/1402 |
| | | | 604/35 |
| 9,511,219 B1 * | 12/2016 | Datta | A61B 18/1492 |
| 9,623,236 B1 | 4/2017 | Datta | |
| 9,656,062 B1 | 5/2017 | Datta | |
| 9,675,799 B2 | 6/2017 | Kroll et al. | |
| 9,987,484 B2 | 6/2018 | Lazeroms et al. | |
| 9,987,485 B2 | 6/2018 | Kroll et al. | |
| 10,039,919 B2 | 8/2018 | Kroll et al. | |
| 10,118,031 B2 | 11/2018 | Kroll et al. | |
| 10,328,243 B2 | 6/2019 | Spear et al. | |
| 10,524,817 B2 | 1/2020 | Grace | |
| 10,525,262 B1 | 1/2020 | Datta | |
| 11,129,566 B1 * | 9/2021 | Perry | A61B 5/4005 |
| 2003/0187461 A1 | 10/2003 | Chin | |
| 2004/0153098 A1 | 8/2004 | Chin et al. | |
| 2004/0215139 A1 | 10/2004 | Cohen | |
| 2005/0004644 A1 | 1/2005 | Kelsch et al. | |
| 2005/0261673 A1 | 11/2005 | Bonner | |
| 2006/0009827 A1 | 1/2006 | Kurth et al. | |
| 2006/0161238 A1 | 7/2006 | Hall | |
| 2007/0005002 A1 * | 1/2007 | Millman | A61M 1/76 |
| | | | 604/30 |
| 2009/0182347 A1 | 7/2009 | Ransbury et al. | |
| 2009/0198251 A1 | 8/2009 | Ransbury et al. | |
| 2009/0299367 A1 * | 12/2009 | Ginnebaugh | A61B 18/1445 |
| | | | 606/49 |
| 2010/0312256 A1 | 12/2010 | Kassab et al. | |
| 2015/0133740 A1 * | 5/2015 | Dierking | A61B 90/30 |
| | | | 600/249 |

FOREIGN PATENT DOCUMENTS

| | | |
|---|---|---|
| WO | 2004058326 A2 | 7/2004 |
| WO | 2008058265 A2 | 5/2008 |

* cited by examiner

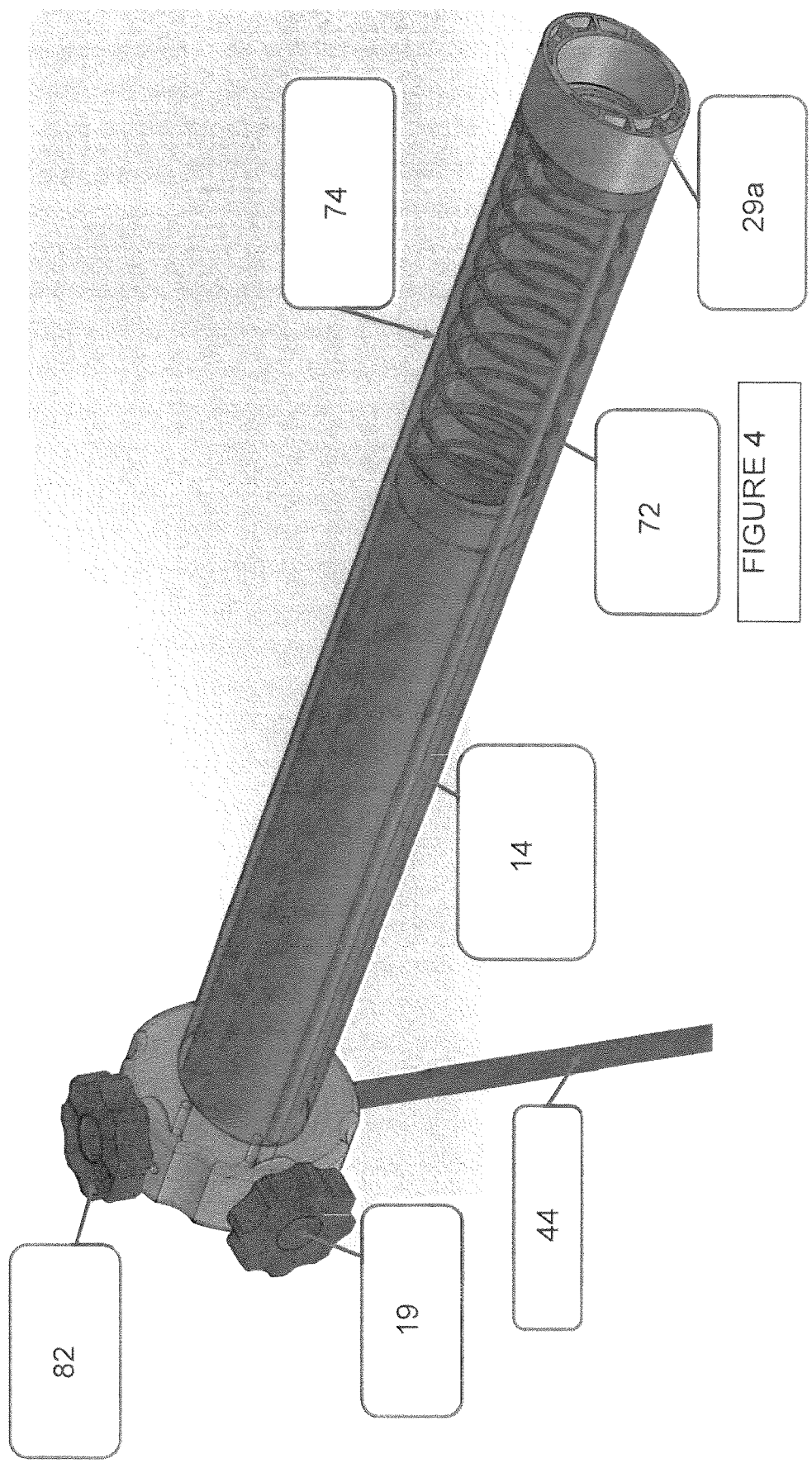

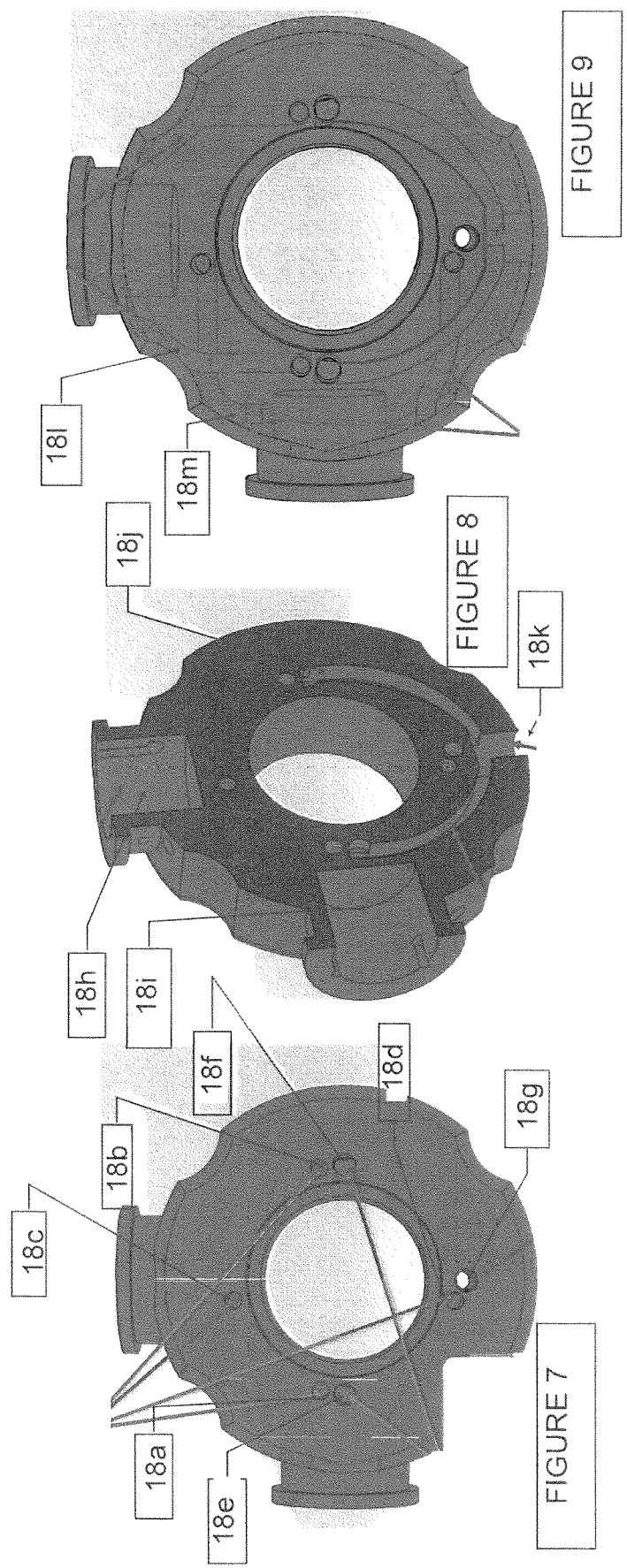

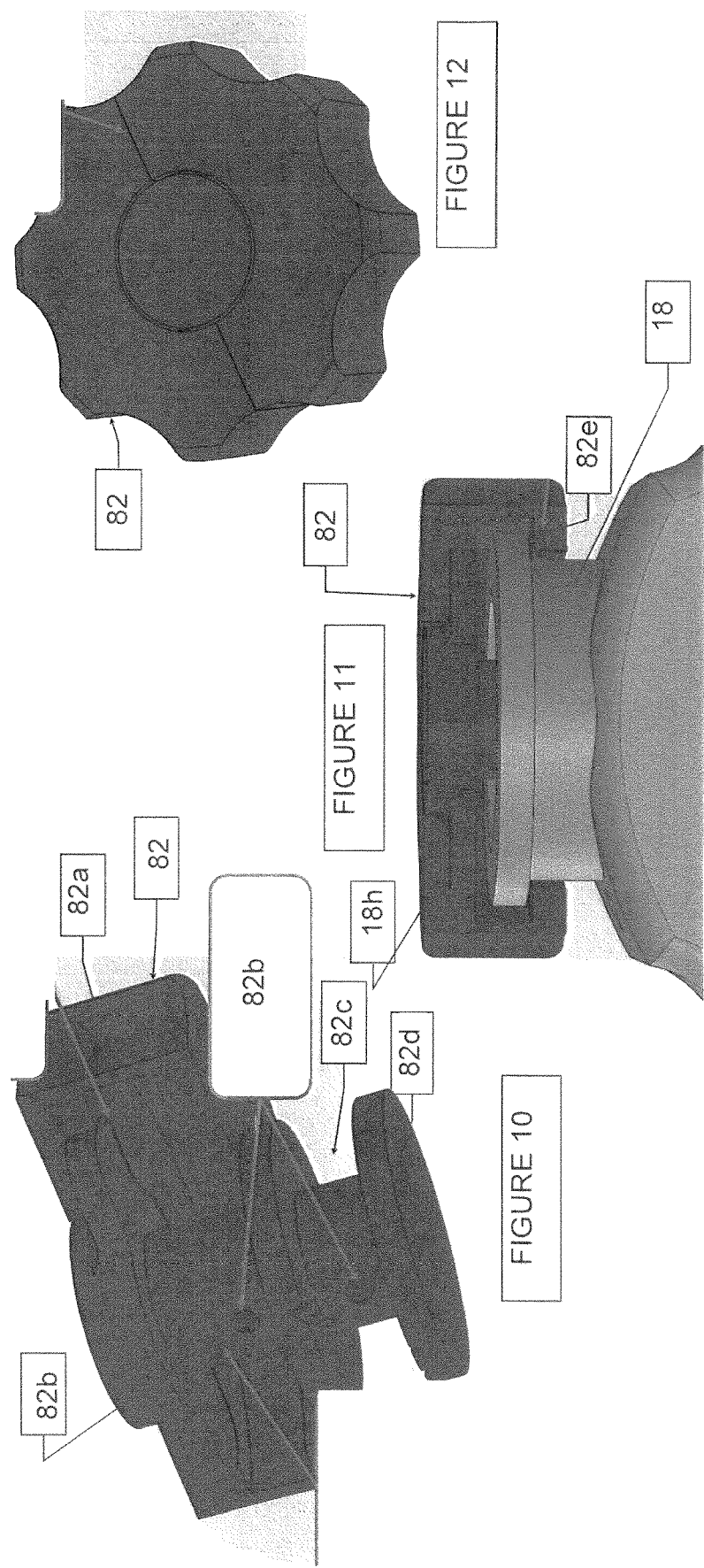

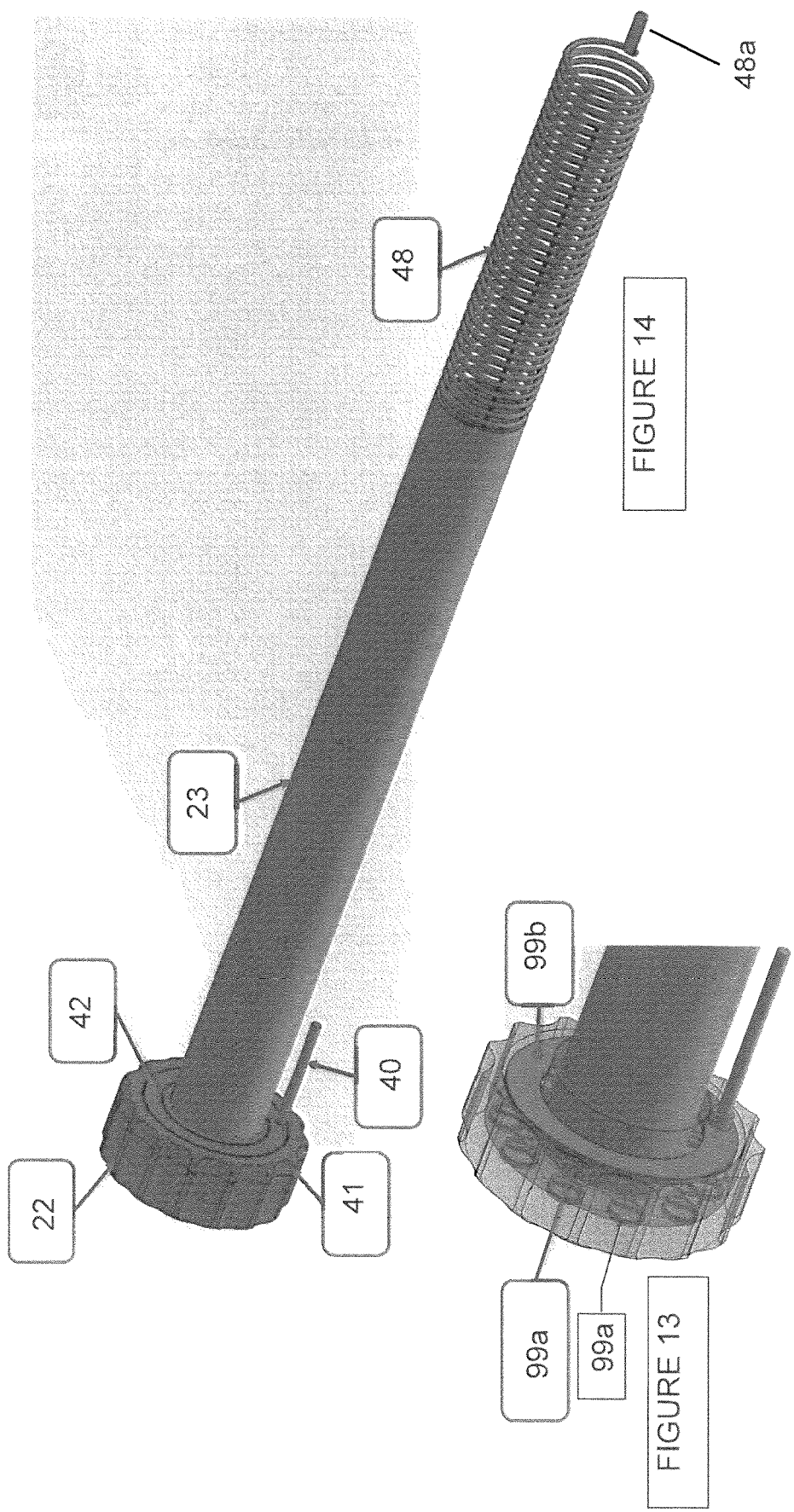

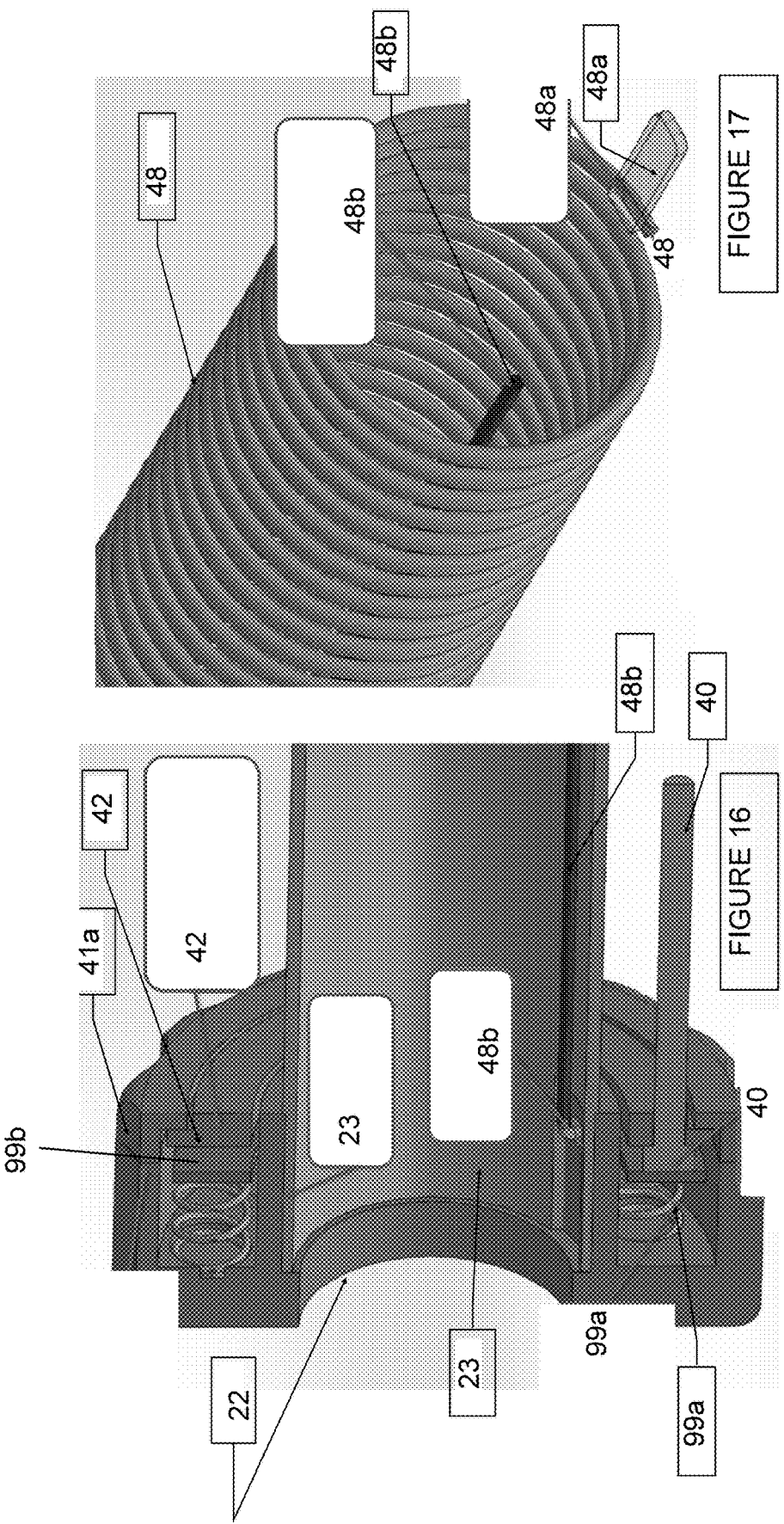

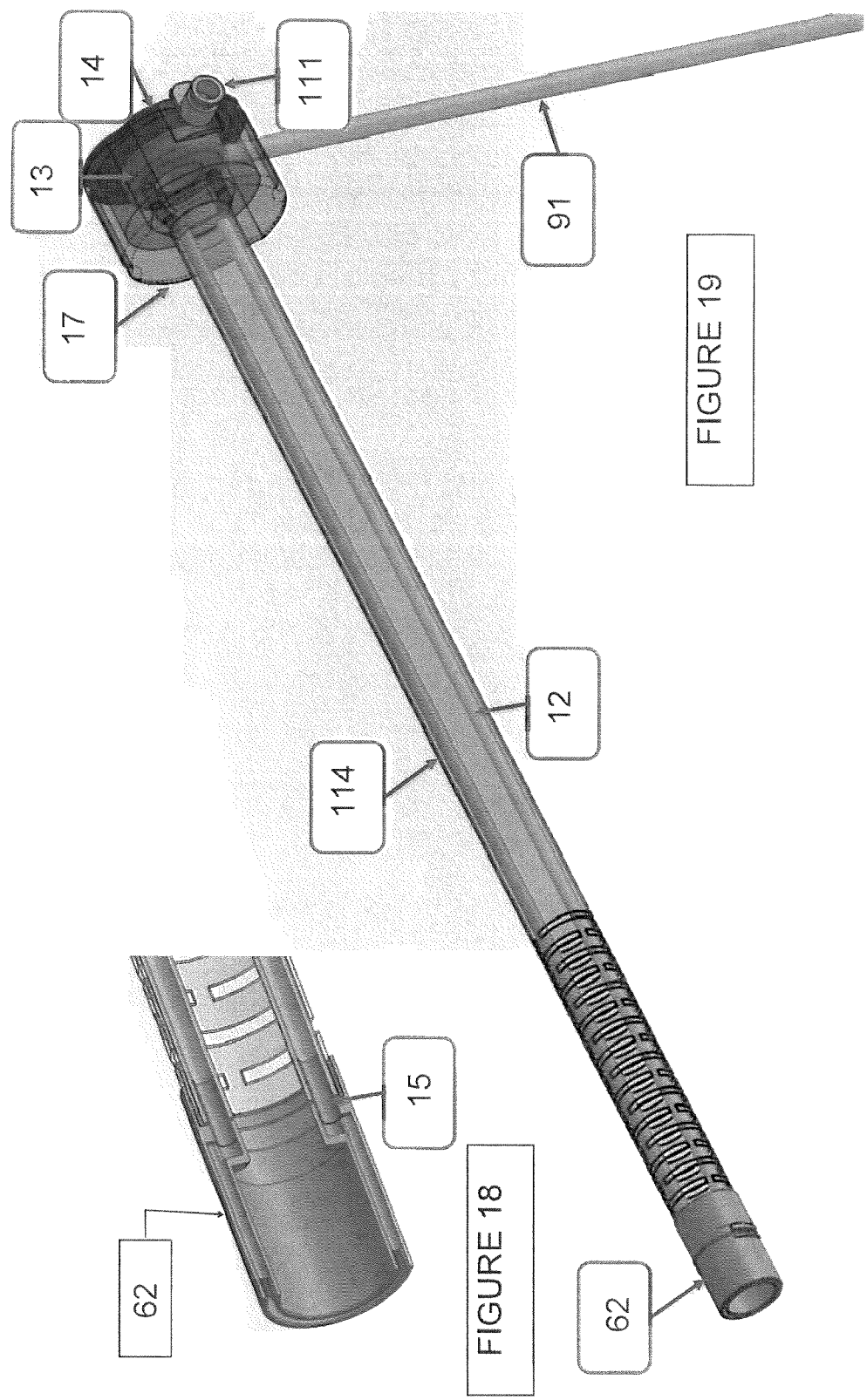

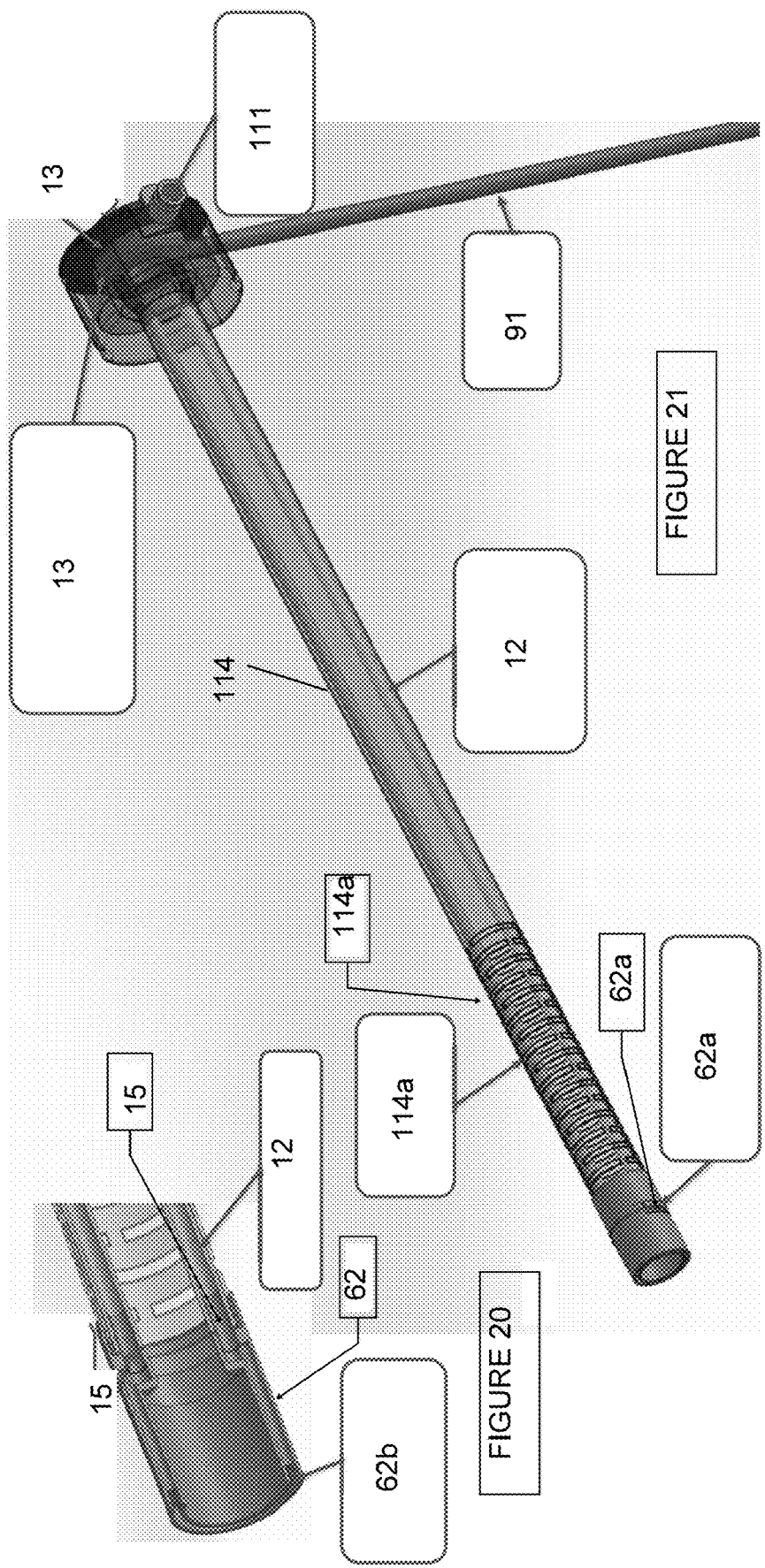

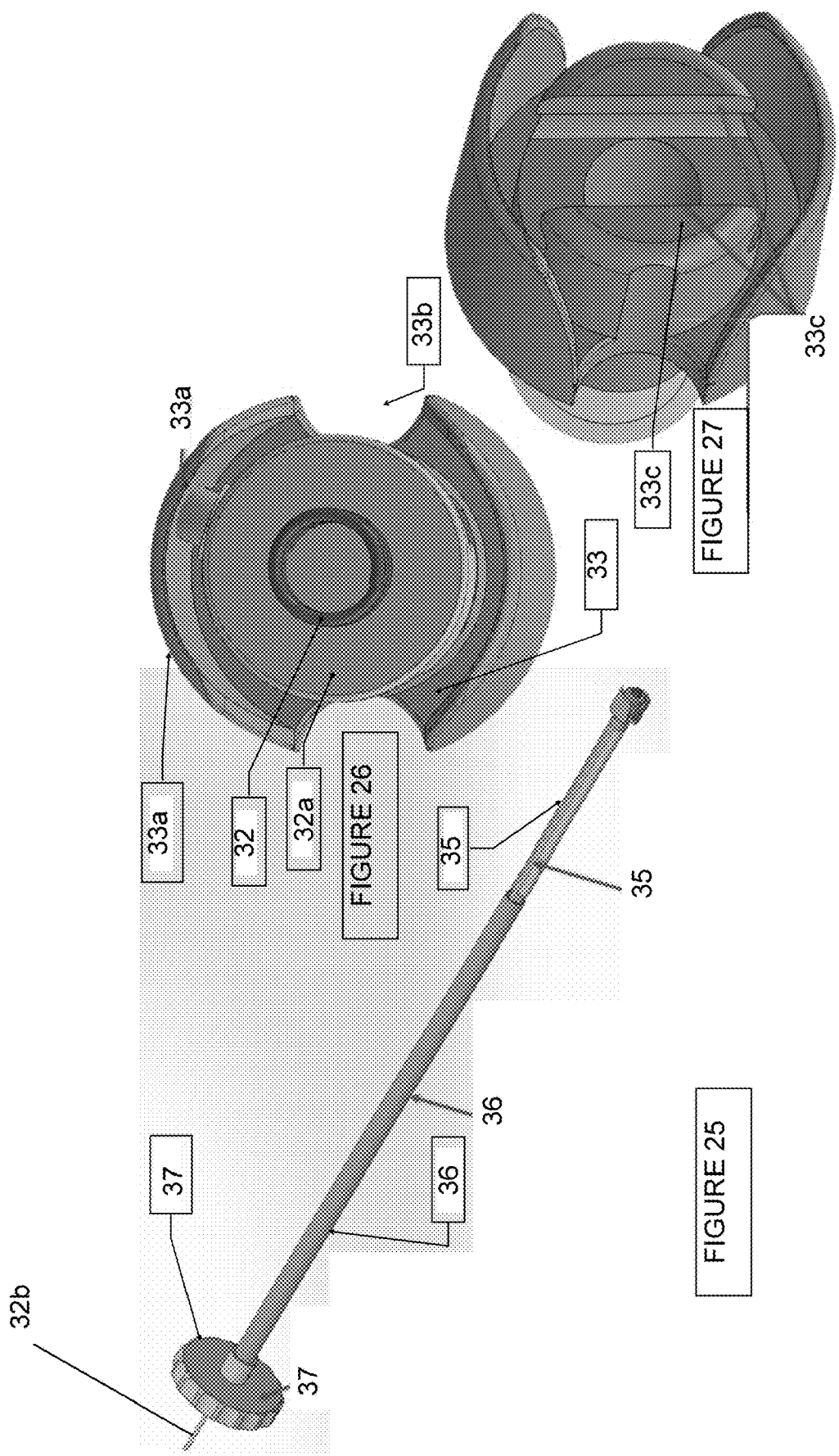

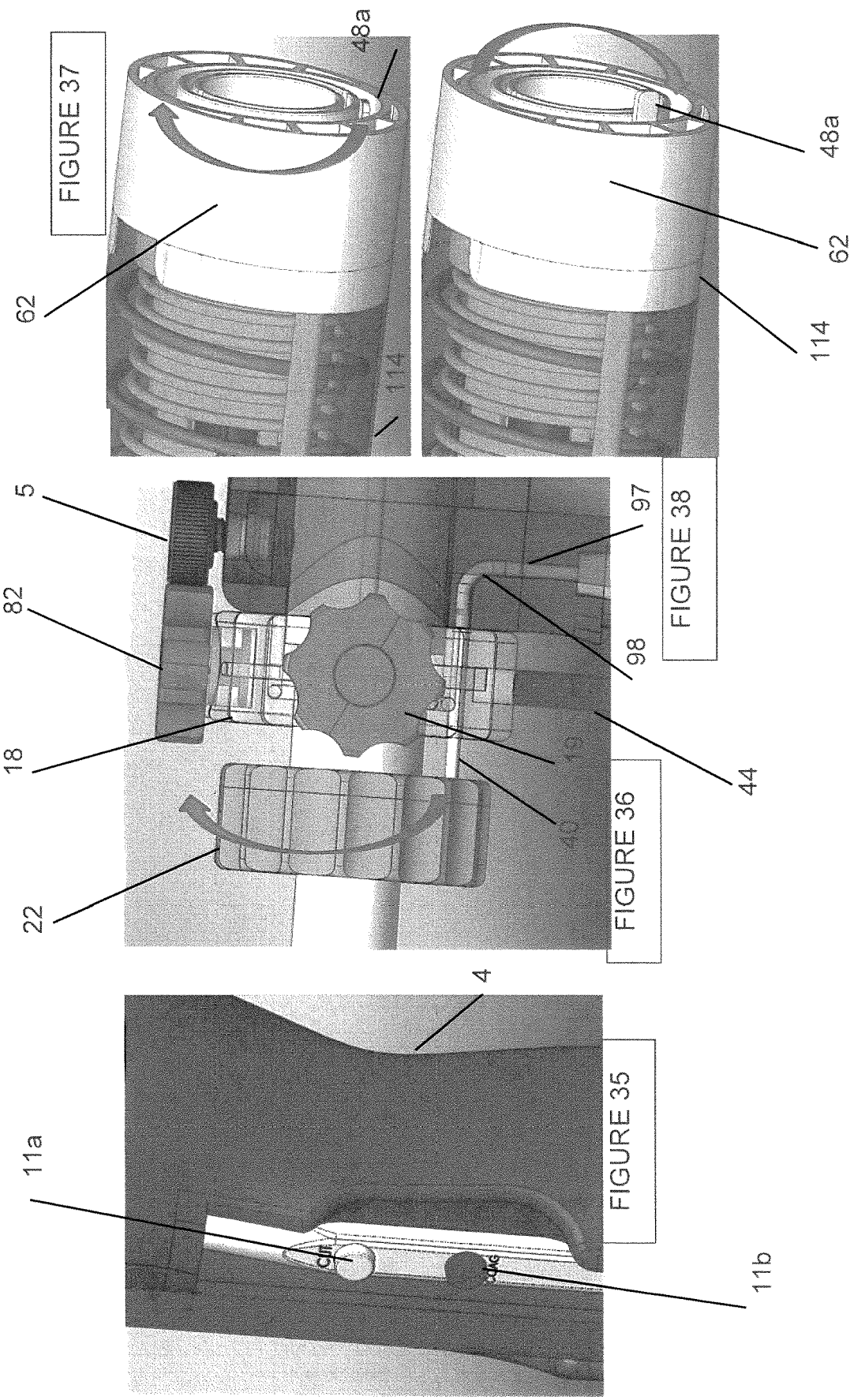

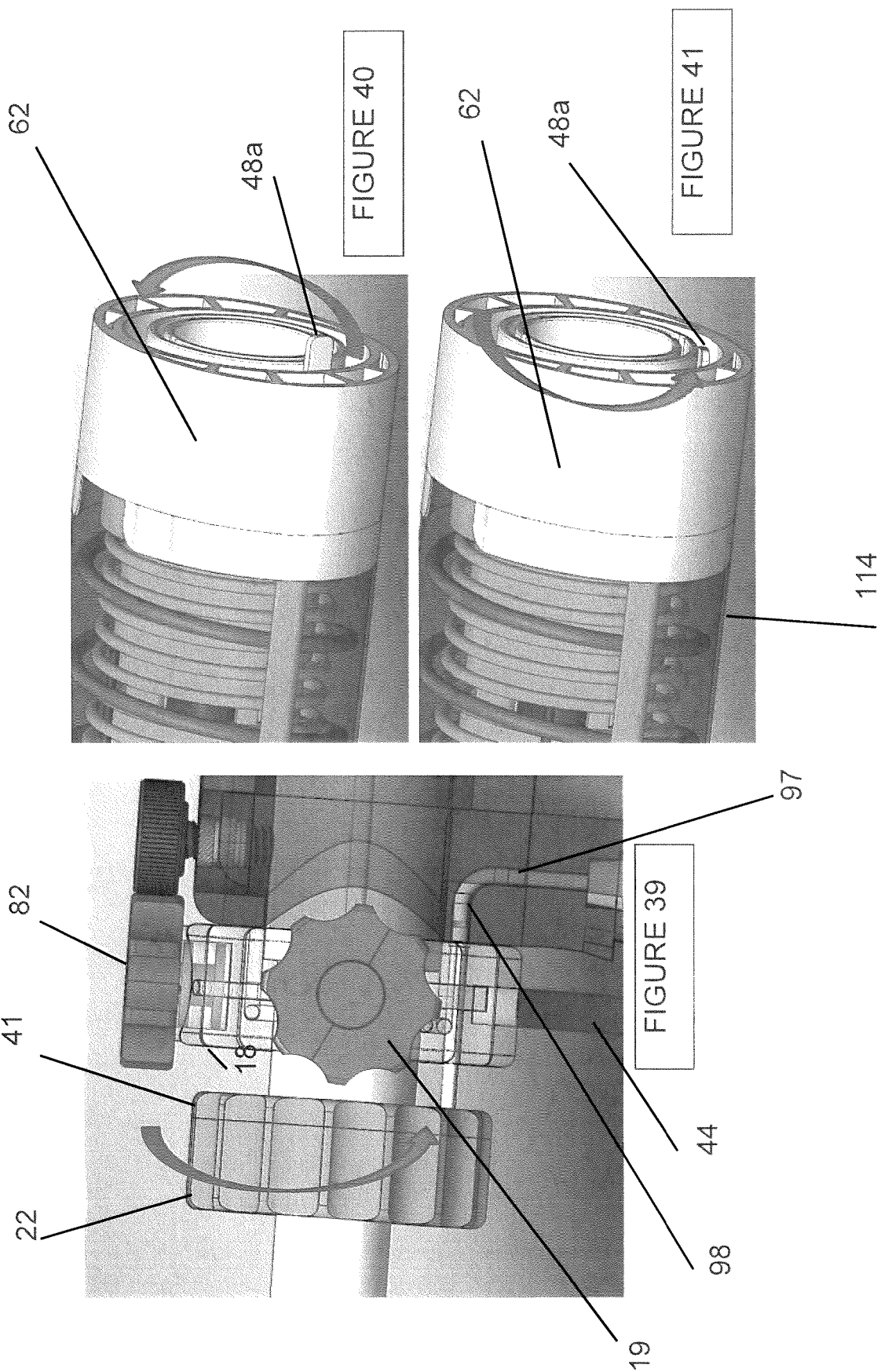

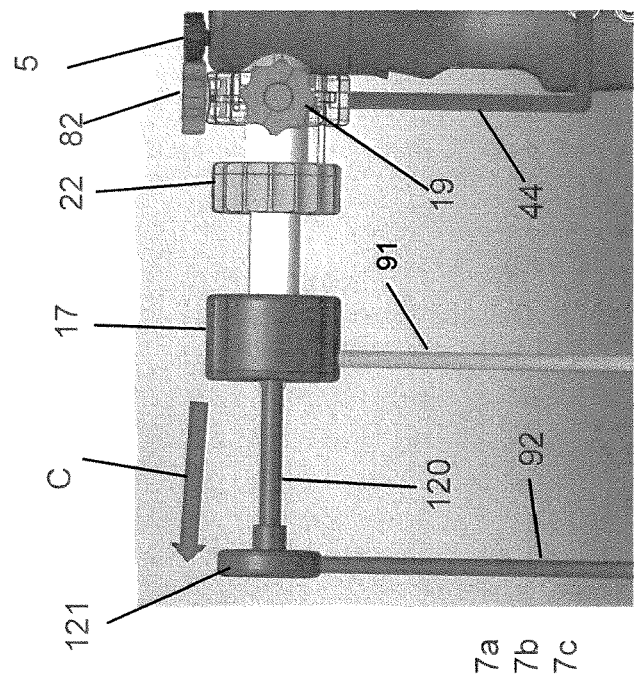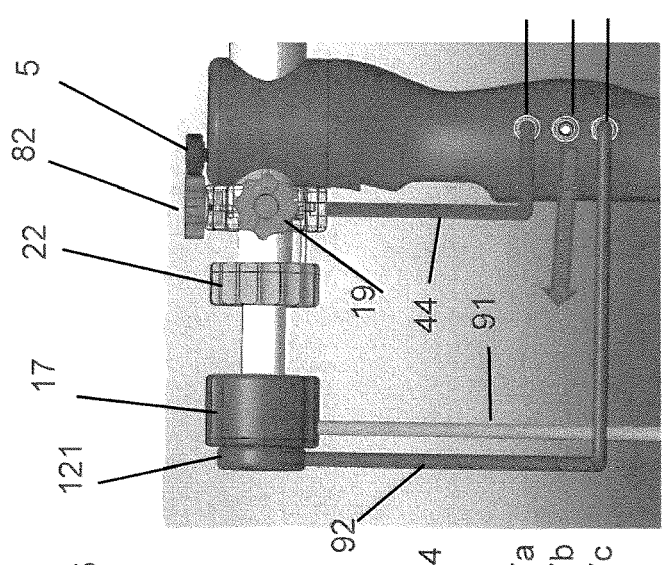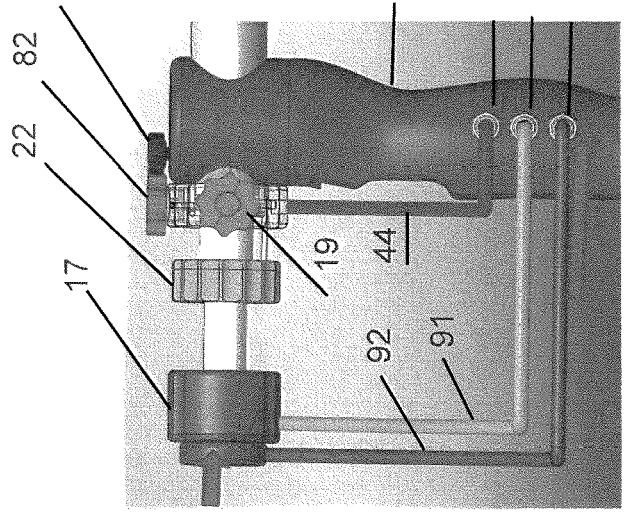

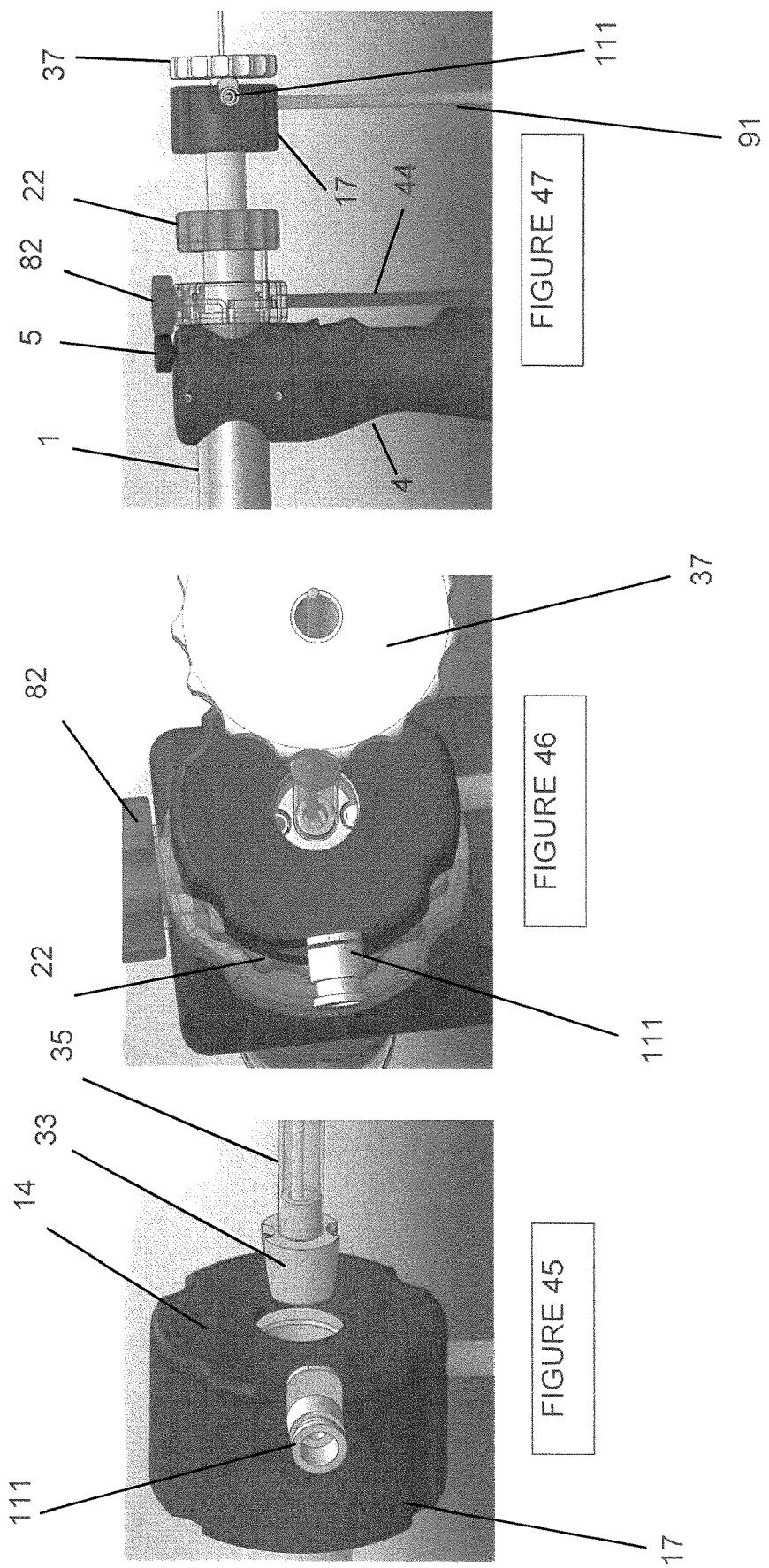

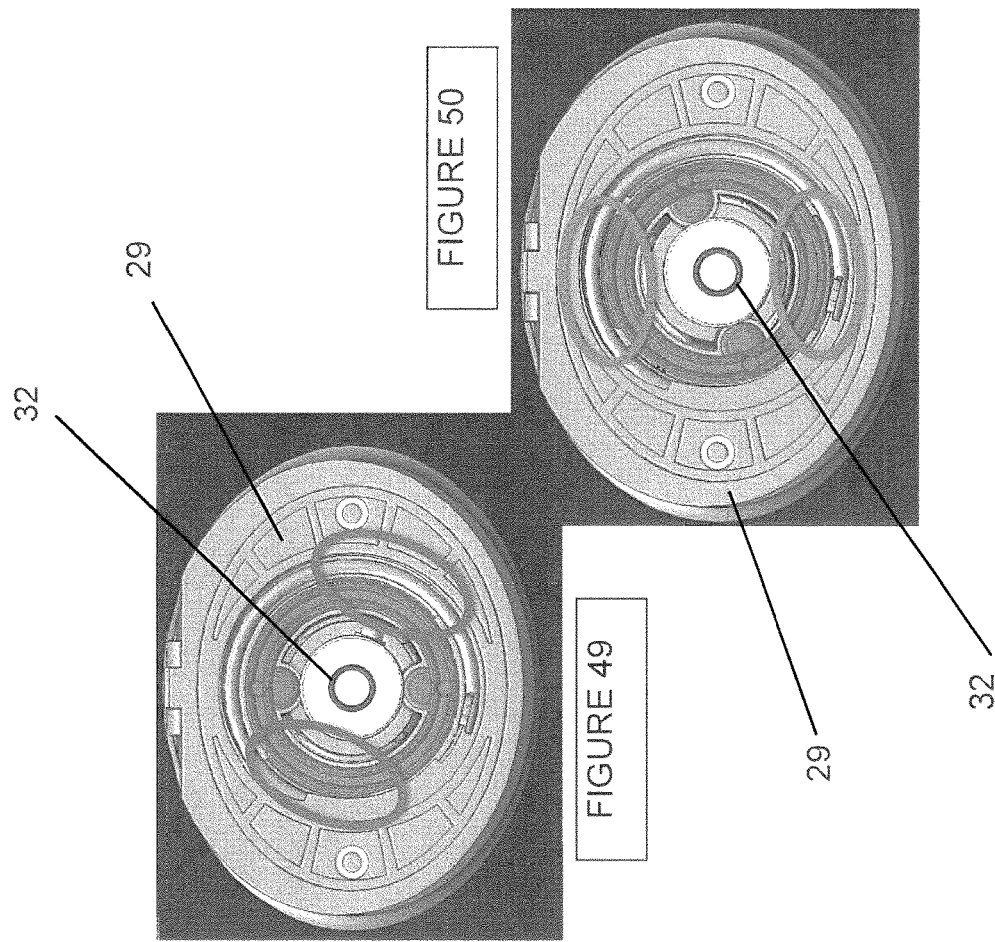
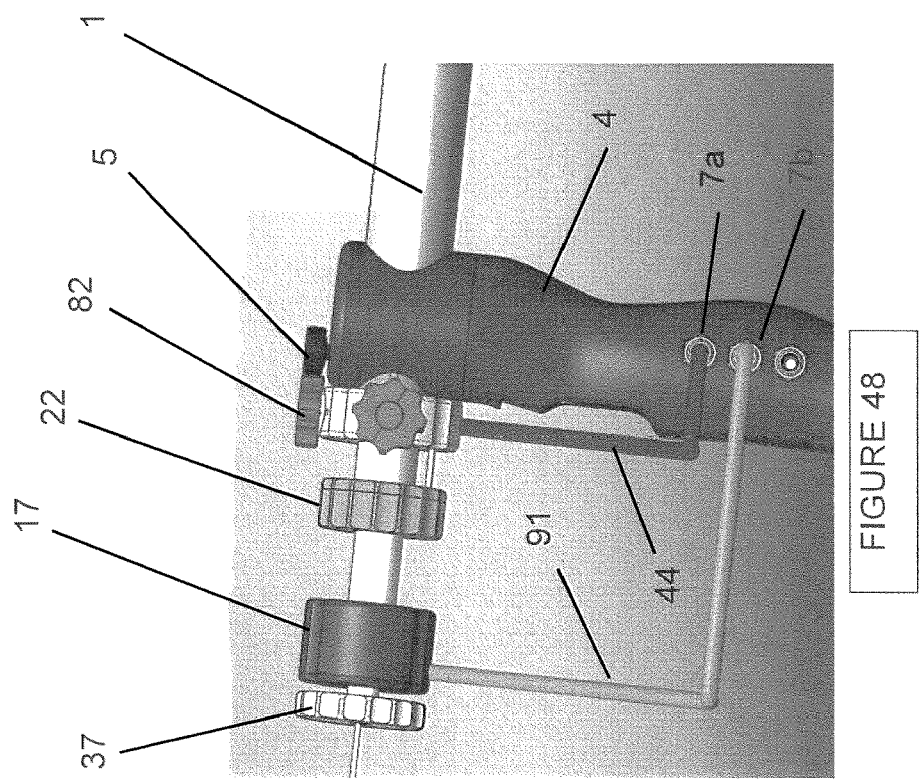

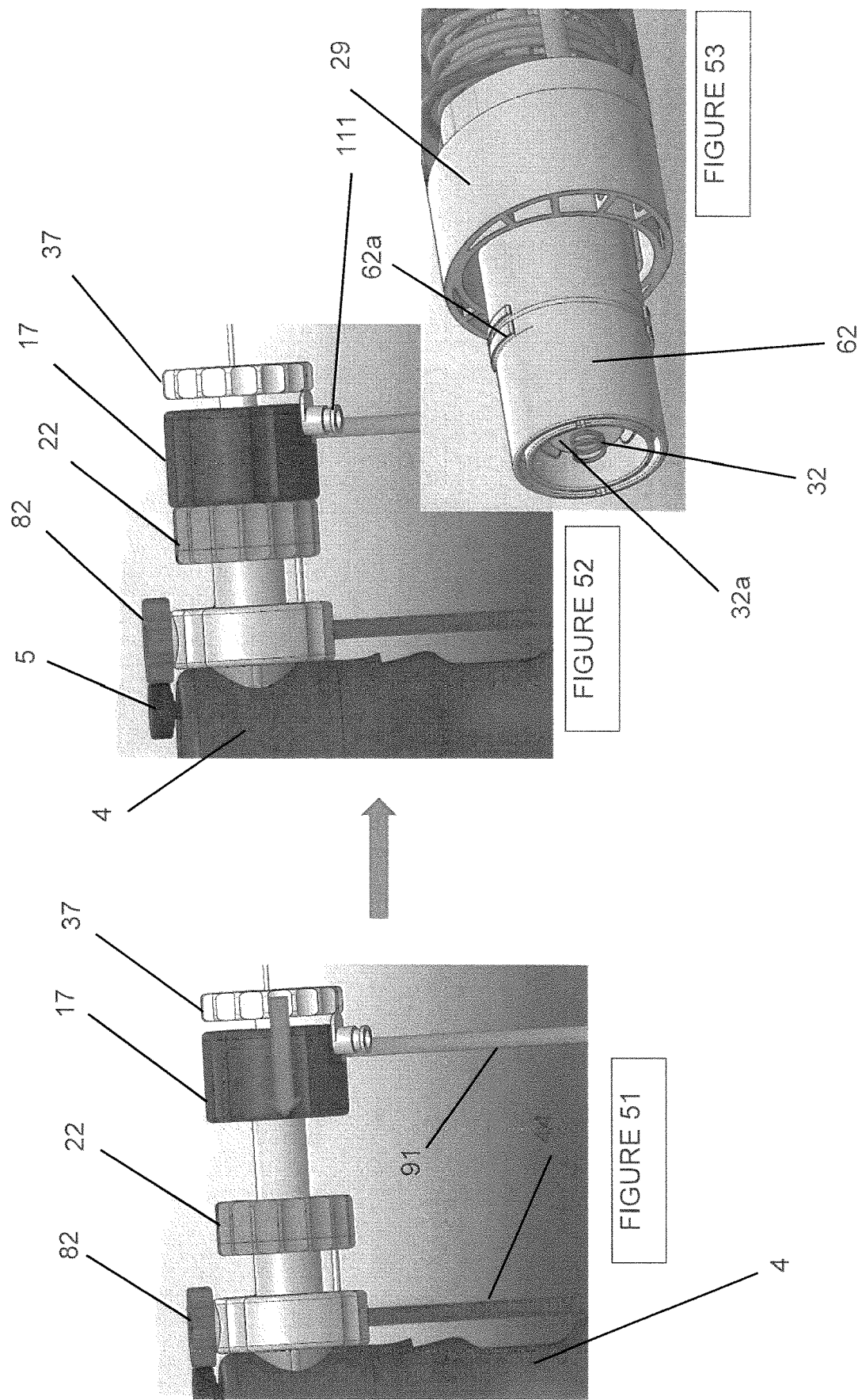

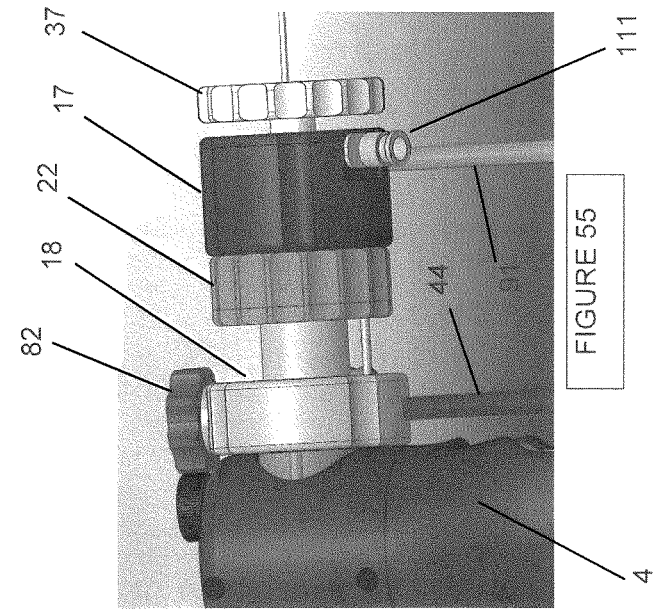
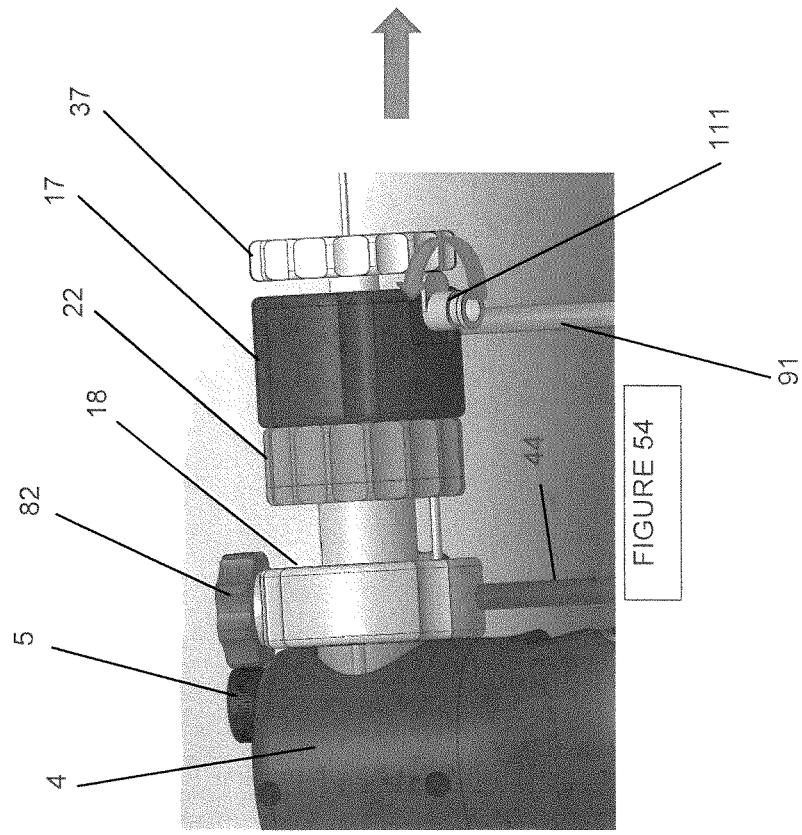

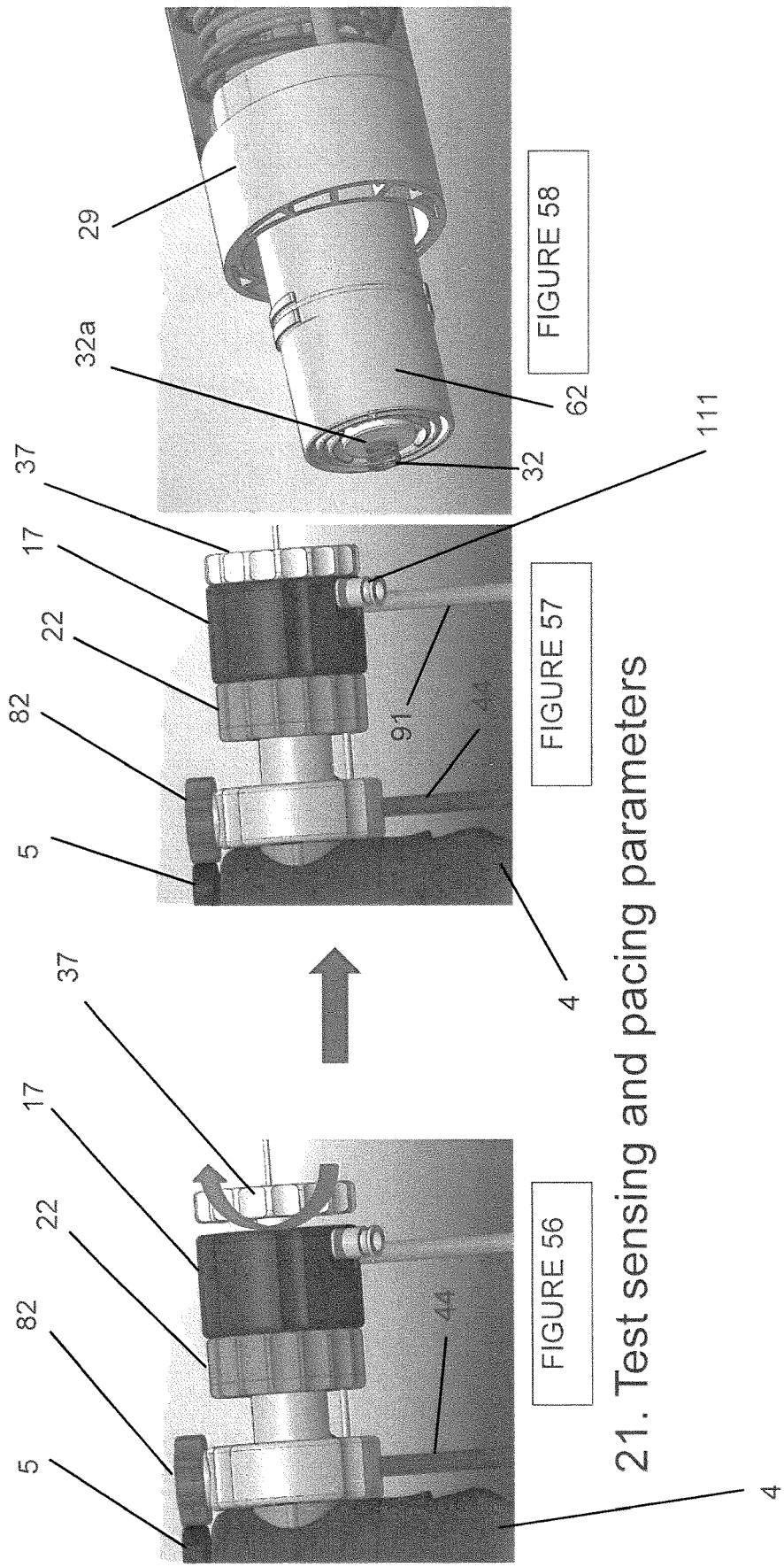

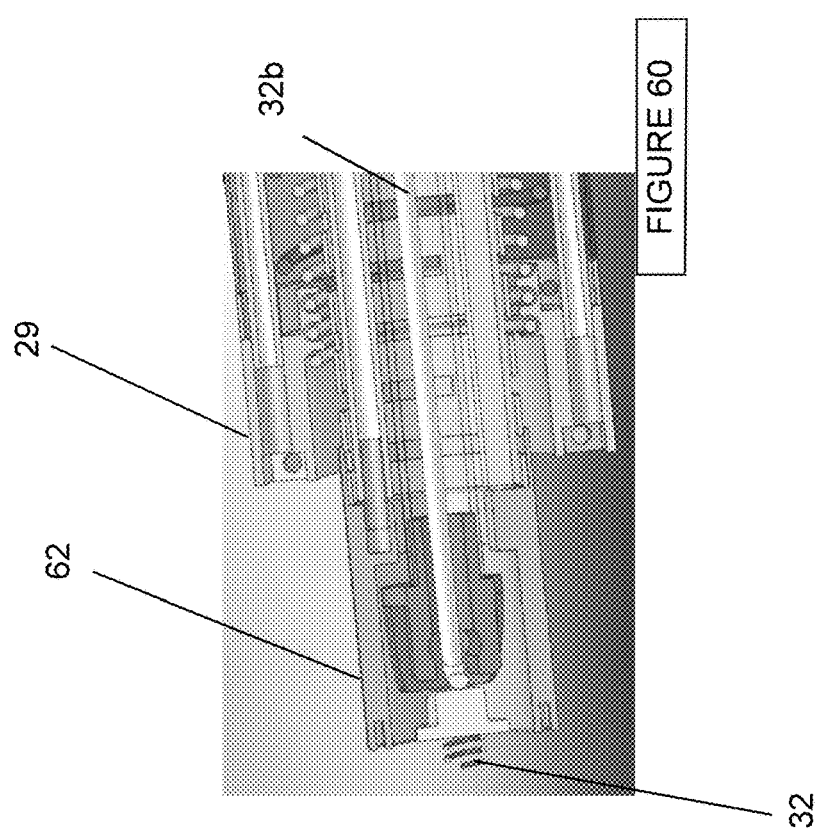
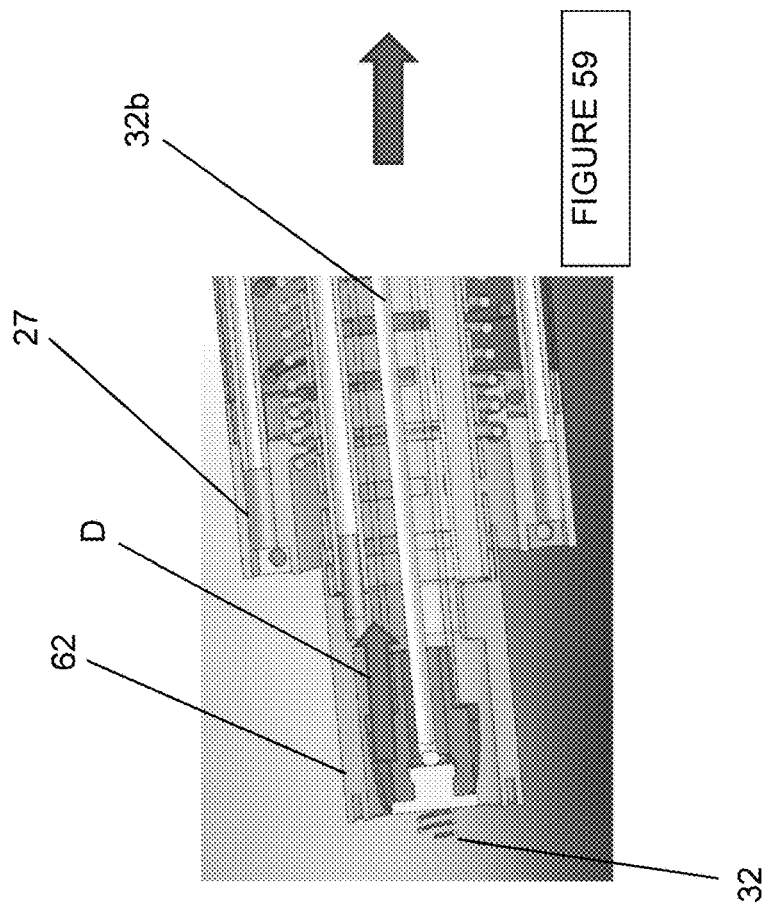

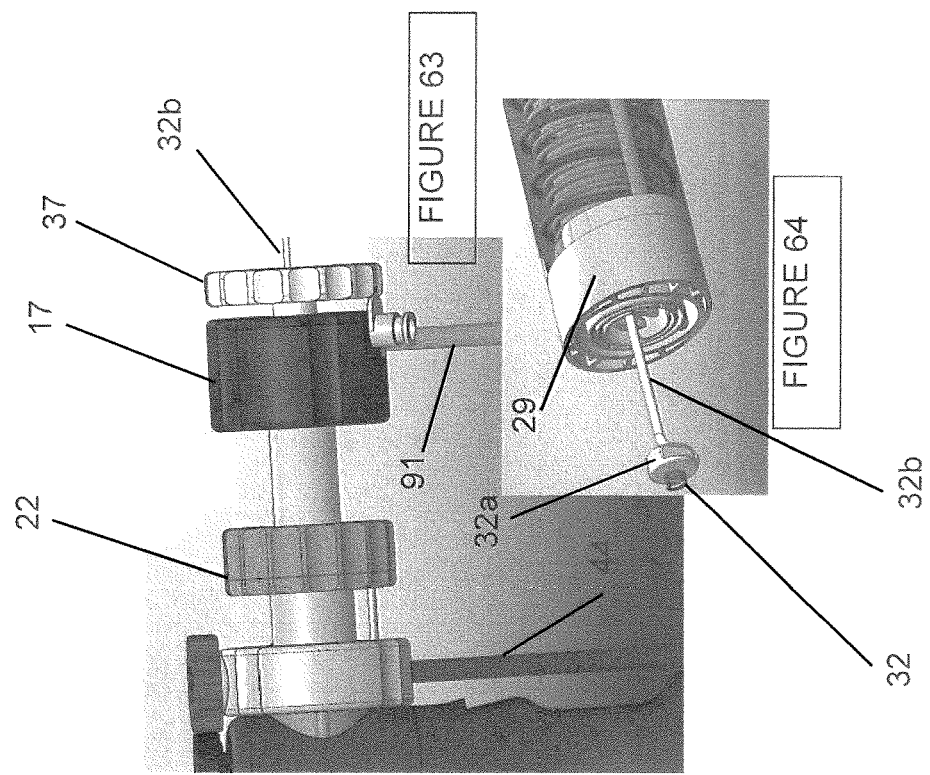
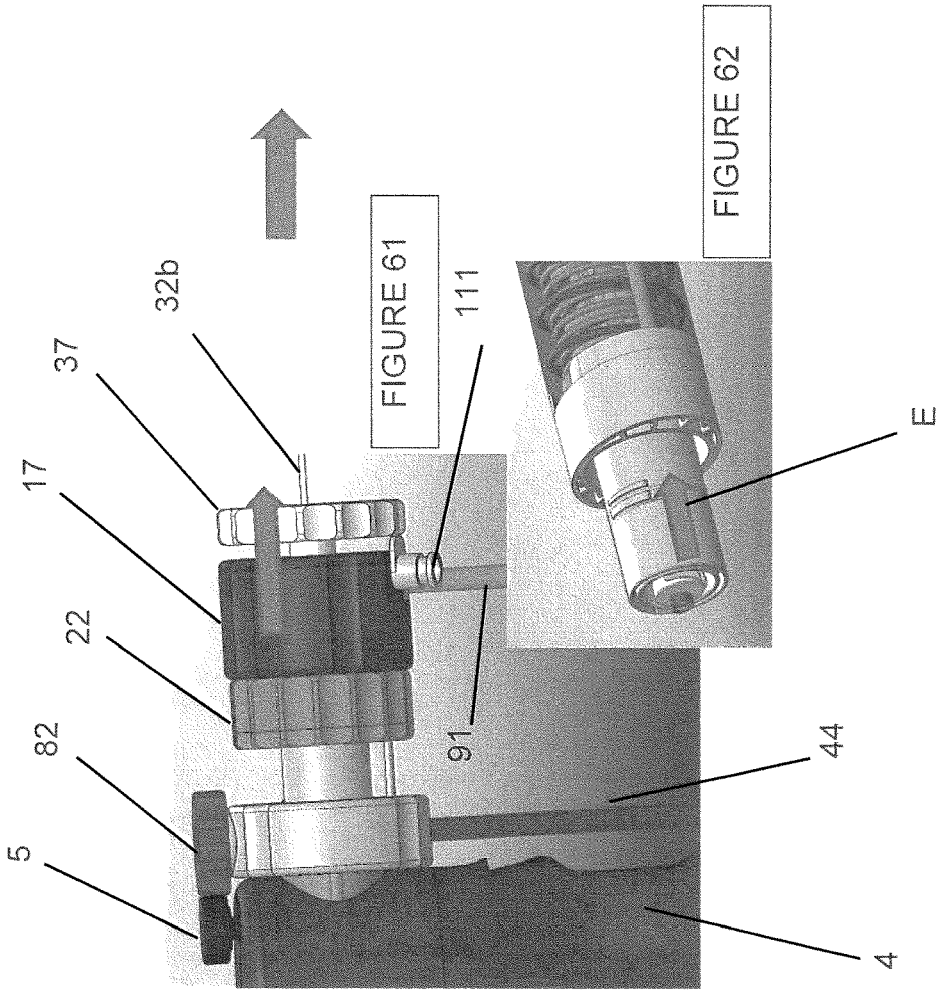

MULTIPLE VACUUM DEVICE FOR MEDICAL FIXTURE PLACEMENT

RELATED APPLICATION DATA

[None]

FIELD OF THE INVENTION

The present invention relates to devices and techniques that may be used in thoracoscopic lead placement, and in similar surgical, therapeutic and testing techniques.

BACKGROUND OF THE INVENTION

According to an AHA statistical brief, nearly 5.8 million people in the United States have congestive heart failure. See Lloyd-Jones D, et al. Heart Disease and Stroke Statistics-2010 Update. A Report from The American Heart Association Statistics Committee and Stroke Statistics Subcommittee. Circulation 2010; 121: E1-E170. About 670,000 people are diagnosed with it each year. Heart failure was a contributing cause of 282,754 deaths in 2006. In 2010, heart failure cost the United States an estimated $39.2 billion. This total includes the cost of health care services, medications, and lost productivity.

Heart failure is a condition in which the heart's pumping power is weaker than normal. With heart failure, blood moves through the heart and body at a slower rate, and pressure in the heart increases. A delay between the contraction of the right and left ventricles (RV and LV) often occurs with heart failure, so the walls of the left ventricle are unable to contract synchronously.

Approximately 25-35% of heart failure patients have ventricles that contract asynchronously, and are therefore candidates for biventricular pacing (between 1.5 and 2.3 million potential patients).

Biventricular pacing, also known as cardiac resynchronization therapy (CRT) utilizes a type of pacemaker that can pace both the septal and lateral walls of the left ventricle.[1] By pacing both the right and left ventricles, the pacemaker can resynchronize a heart. Candidates for CRT include patients with severe or moderately severe heart failure symptoms (NYHA Class II-IV), delayed electrical activation of the heart (such as intraventricular conduction delay or bundle branch block), or those with a history of cardiac arrest or risk factors for cardiac arrest.

[1] Pavia S V, Wilkoff B L. Biventricular pacing for heart failure. Cardiol Clin. 2001 November:19(4):637-51.

CRT improves symptoms of heart failure in about one third of patients who have been treated maximally with medications but still have severe or moderately severe heart failure symptoms. Another third of patients see an improvement in ejection fraction without any major change in symptoms and the last third of the patient population are not responsive to CRT (Non-responders). CRT improves survival, quality of life, heart function, the ability to exercise, and helps decrease hospitalizations in select patients with severe or moderately severe heart failure. CRT can help improve ejection fraction (volume of blood pumped out of the left ventricle) and when combined with an implantable cardiac defibrillator or pacemaker, it can help protect against dangerous, fast heart rhythms.[2] Both CRT pacemakers and CRT defibrillators use a left ventricular pacing lead.

[2] Bristow M, et al. Cardiac-resynchronization therapy with or without an implantable defibrillator in advanced chronic heart failure. 2004. N Engl J Med 350 (21): 2140-50.

The CRT device and its leads can be implanted using an endocardial (transvenous) or epicardial approach. The endocardial approach is the most common method. A local anesthetic is given to numb the area. The leads are inserted through an incision in the chest skin and access into a vein (percutaneous transvenous). Two leads are guided to the right atrium and right ventricle of the heart (endocardial attachment), while the third lead is guided through the coronary sinus (the venous system of the heart) to the left ventricle (theoretically epicardial placement). The lead tips are attached to the heart muscle, while the other ends of the leads are attached to the pacemaker placed in a pocket created under the skin in the upper chest. When the endocardial approach is used, the hospital recovery time is generally 24 hours. The percutaneous technique is technically challenging for LV lead placement. In some cases, this technique may not be successful due to the size, shape or location of the vein(s). If the percutaneous approach cannot be used or is unsuccessful or in Non-responders, the epicardial surgical approach may then be attempted.

The epicardial approach is a less common method in adults, but more common in children. The leads are placed under general anesthesia. The locations of lead placement are identical to the endocardial approach. The pulse generator is placed in a pocket created under the skin in the abdomen or chest. Although recovery with the epicardial surgical approach (more invasive) is longer than that of the transvenous approach (generally about 3 to 5 days), but minimally invasive techniques have enabled shorter hospital stays and recovery times.

There are several complications and costs associated with conventional pacing that may occur during biventricular pacing, including: (a) localized/skin infection, (b) systemic infection secondary to infected pacing box or lead, (c) bleeding, (d) hematoma, (e) lead displacement, (f) equipment failure, i.e. fractured pacing wire, faulty pacing box and (g) pneumothorax.

Standard predictors of operative complications apply, those being degree of heart failure, the surgical environment, diabetes and the duration of the procedure. Although with experience the procedure times reduce, even in the best hands implantation of the left ventricular lead may be time consuming, contributing to an increased infection risk.[3]

[3] Alonso, C, et al. Six year experience of transvenous left ventricular lead implantation for permanent biventricular pacing in patients with advanced heart failure: technical aspects. Heart. 2001; 86(4):405-410.

In the initial studies of biventricular pacing, the right atrial and right ventricular leads were inserted via the standard transvenous approach, but the epicardial left ventricular lead was placed surgically via thoracotomy or thoracoscopically. These approaches required a larger incision and general anesthetic, consequently carrying a significant morbidity and mortality.

In 1998, the preferred method of left ventricular lead insertion using the transvenous approach was introduced.[4] The precise location of the lead is ideally the mid left ventricular cavity in a lateral or posterolateral vein.[5] The use of guiding catheters, wires and balloons within the coronary sinus and the use of purpose-designed leads have increased success rates and ability to reach the target vessel at physiologically desired location. Some of these procedures may require the use of multiple types of catheters and guidewires, adding cost to this procedure. The requirement to position a lead in a branch of the coronary sinus and the techniques required to achieve this account for the additional complications and significant failure rate seen with biventricular pacing. A suitable vein may not be present in the lateral or posterolateral position, prompting placement of left ventricular lead in another ineffective suboptimal location. Thoracoscopic placement of left ventricular lead is not dependent on cardiac venous anatomy. Trans-cardiac-venous placement of left ventricular lead occasionally will cause disturbing phrenic nerve stimulation, causing uncomfortable diaphragmatic twitching and necessitate relocation to suboptimal sites. Thoracoscopic placement visualizes the phrenic nerve and thus placement away from the nerve can be accomplished at the outset.

[4] Daubert, J C, et al. Permanent left ventricular pacing with transvenous leads inserted into the coronary veins. Pacing clin. Electrophysiol. 1998; 21(1 pt 2):239-245.

[5] Auricchio, A, et al. The pacing therapies for congestive heart failure (path-chf) study: rationale, design, and endpoints of a prospective randomized multicenter study. Am. J. Cardiol. 1999; 83(5b):130d-135d.

Although devices of various types have been developed for the endocardial approach, there remains a need for a device that is relatively simple to construct and use that permits firm and accurate lead or conduit placement in tissue, including cardiac tissue at a physiologically desired location with mapping. There also are applications relating to a variety of operations and procedures involving the placement of a variety of leads or conduits in a variety of tissues that likewise would benefit from the device and methods of the present invention.

SUMMARY OF THE INVENTION

The present invention includes additional embodiments of the devices and methods described in Application Ser. No. 61/774,406, filed Mar. 7, 2013, and application Ser. No. 14/186,532, filed Feb. 21, 2014, and in U.S. Pat. Nos. 9,511,219; 9,623,236; 9,656,062 and 10,525,262, all of which are hereby incorporated herein by reference, and whose features may be incorporated independently into the present invention. The present inventions include improvements to the devices and methods disclosed in those applications in addition to inventions related generally to thoracoscopic lead placement, and in similar or related surgical techniques and treatments, such as those for electrical mapping of the heart and the treatment of structural heart disease, that may involve the placement of fixtures and implants on heart.

It is an object of the present invention to provide an improved pacing lead placement device. The object is achieved by a pacing lead placement device and method according to the independent claims. Other more specific embodiments of the invention are given in the dependent claims.

In the context of this specification the term proximal refers to the direction pointing towards the patient during a pacing lead placement procedure, while the term distal refers to the opposite direction pointing away from the patient. In the context of this specification the term distal end refers to the end of the device closer to the patient during a pacing lead placement procedure, while the term proximal end refers to the opposite end nearest the operator of the device; i.e., furthest from the patient.

The present invention includes devices and methods directed to the placement of foreign objects into organs and other body parts, especially where the body parts are in motion, and are described in the context of the placement of a cardiac pacing contact or lead (i.e., the object) on or into the heart (i.e., as an example of an organ and other body part). The invention may be used for contact, lead on other fixture placement in humans or non-humans, and may also include a kit comprising the individual, separable parts of the device of the invention. The devices and methods are particularly adapted for such operations where there is a requirement or some benefit in the articulation of the instrument to facilitate better approach to the target site, as well as where there is a requirement or some benefit to the excision of tissue in advance of the object placement and attachment to a moving organ or tissue before precise placement of a lead or probe.

The present invention includes arrangements that feature the use of three separate vacuum conduits that function to attach to and stabilize tissue surface, allow co-axial telescopic movement of individual suction conduits, to remove tissue with third waste vacuum conduit, such as that cut from the pericardium entry site, to make the procedure more efficient by eliminating the need to extract the relatively inner vacuum conduit components as may be necessary in pericardial or epicardial applications of the device, lead or fixture described in earlier applications.

The present invention includes the provision of a third waste removal vacuum tube positioned so as to remove the monopolar-electrocautery-(ME)-cut pericardium. Thus, the relatively inner vacuum conduit serving the relatively inner vacuum foot need never be removed from the device during its use. The lead driver may then be introduced inside the relatively inner vacuum tube (i.e., inside the area of the tissue removed by the monopolar electrocautery (ME) blade).

In one embodiment, the electrocautery pen may be fit into the handle of the device so as to be removably captive in the handle of the device (as an alternative to having the electrocautery pen being integrated into the handle of the device through original manufacture). The electric connection is passed from the electrocautery pen to the rotatable electrocautery blade by a circular coil or plate such that, when the electrocautery blade rotates in order to bring electrocautery energy to the target tissue in order to cut and remove it, the electrocautery blade remains in electric contact with the electrocautery pen or other electrocautery energized handle.

In one embodiment, the outside suction ends at the electrocautery end of the electrocautery handle, and is split into three lines on the electrocautery side of the electrocautery handle which includes a "push to connect" type adapter that provides the vacuum (gas) fluid connection. The suction of each vacuum tube may be arranged such that each vacuum tube can be individually connected/disconnected to the device handle. The vacuum (gas) fluid connections are thereby arranged such that, when disconnected, the self-locking electrocautery end closes up.

The present invention may be summarized as follows:

Summary of the Elements

There are several optional arrangements of the present invention that are described in its many embodiments.

In general terms, the device of the present invention is adapted for the thoracoscopic placement of a lead or other medical fixture at a target site on an epicardial surface of a heart, and comprises: (a) an inner tubular vacuum conduit having an inner vacuum conduit distal end comprising an inner suction foot portion, the inner tubular vacuum conduit having a flexible distal end and adapted to conduct a vacuum to the relatively inner suction foot portion; (b) an outer tubular vacuum conduit having an outer vacuum conduit distal end comprising an outer suction foot portion, the outer tubular vacuum conduit having a flexible distal end and adapted to conduct a vacuum to the outer suction foot portion, the inner tubular vacuum conduit slidingly engaged within outer tubular vacuum conduit, so as to permit the inner suction foot portion to be moved from a position within the outer suction foot portion to a position extended beyond the outer suction foot portion; (c) at least one actuator adapted to articulate the outer suction foot portion while the inner suction foot portion is disposed within the outer suction foot portion; (d) a waste removal vacuum conduit having a waste removal vacuum conduit distal end, and slidingly engaged within the inner tubular vacuum conduit so as to permit the waste removal vacuum conduit distal end to be urged to the position of the inner suction foot portion; (e) an electrocautery blade extensible from between the inner suction foot portion and the outer suction foot portion; and (f) a support sheath having a proximal inlet and a distal lead outlet for supporting the vacuum conduits.

The invention may also be understood as being a device adapted for the thoracoscopic placement of a lead on an epicardial surface of a heart (or other medical fixture at a target site on an organ or other body part), and comprises: (a) an inner tubular vacuum conduit having an inner vacuum conduit distal end comprising an inner suction foot portion, the inner tubular vacuum conduit being flexible (variable distal end flexible and rest proximal portion being relatively rigid) and adapted to conduct a vacuum to the inner suction foot portion; (b) a lead with lead drive insertable through the inner tubular vacuum conduit proximal end; (c) a lead extending through the lead head portion and having a lead distal end portion, the lead distal end portion extending from the distal end of the inner tubular vacuum conduit for contact with the epicardial surface of the heart; (d) an outer tubular vacuum conduit having an outer vacuum conduit distal end comprising an outer suction foot portion, the outer tubular vacuum conduit being flexible (in one embodiment, the distal end being relatively flexible, and balance of the vacuum conduit; i.e., the proximal portion, being relatively rigid), and adapted to conduct a vacuum to the outer suction foot portion while being adapted to slidingly conduct the inner tubular vacuum conduit, so as to permit the inner tubular vacuum conduit to be extended from the outer vacuum conduit distal end (allowing the longitudinal movement of the former with respect to the latter, and the independent articulation of multiple tubular vacuum conduits both when co-terminal within one another, and when the inner tubular vacuum conduit is extended from the outer tubular vacuum conduit); (e) a support sheath having a longitudinal axis, a proximal end portion and a distal end portion, and having a proximal inlet and a distal lead outlet for extending the inner and outer vacuum conduits therethrough, the support sheath comprising a lead receiving passageway for receiving and conducting the inner and outer vacuum conduits between the proximal inlet and the distal lead outlet; the lead head portion adapted to releasably engage the inner suction foot portion such that such engagement is of sufficient strength to maintain the position of the lead distal end portion as it engages the epicardial surface of a heart, and sufficiently releasable such that the lead head portion may be released from the inner suction foot portion once the lead is attached (i.e., preferably screwed into the heart muscle) to the epicardial surface of a heart; and (f) a first actuator extending from the proximal end portion to the distal end portion and adapted to articulate the outer suction foot portion; (g) a second actuator extending from the proximal end portion to the distal end portion and adapted to articulate the inner suction foot portion; (h) an electrocautery blade extending from between the inner and outer suction foot portions; and (i) a waste removal tubular conduit adapted to conduct a vacuum to the distal end of the device.

The present invention generally includes a lead or conduit placement device that is configured to permit the use of an electrocautery blade extending from between the first, relatively inner and a second, relatively outer vacuum suction foot portions; a waste removal tubular vacuum conduit adapted to conduct a vacuum to the distal end of the device to remove tissue freed by the electrocautery blade (such as a portion of the pericardium tissue of a heart of a human or animal); and at least one actuator to articulate the suction feet to a desired position with respect to the target tissue, while the pacing contact or lead is releasably attached to the placement foot to permit it to be released from the placement foot after fixing the lead or conduit in the tissue.

Another device variant is one adapted for the thoracoscopic placement of a lead at a target site on an epicardial surface of a heart, the device comprising: (a) an inner tubular vacuum conduit having an inner vacuum conduit distal end comprising an inner suction foot portion, the inner tubular vacuum conduit having a flexible distal end and adapted to conduct a vacuum to the inner suction foot portion; (b) an outer tubular vacuum conduit having an outer vacuum conduit distal end comprising an outer suction foot portion, the outer tubular vacuum conduit having a flexible distal end and adapted to conduct a vacuum to the outer suction foot portion while being adapted to slidingly conduct the inner tubular vacuum conduit, so as to permit the inner tubular vacuum conduit to be extended from the outer vacuum conduit distal end and so as to be moveable a first position wherein the inner suction foot portion is substantially coplanar with the outer suction foot portion to a second position wherein the inner suction foot portion extends beyond the plane of the outer suction foot portion; (c) a support sheath having a longitudinal axis, a proximal end portion and a distal end portion, and having a proximal inlet and a distal lead outlet for extending the inner and outer vacuum conduits therethrough, the support sheath comprising a passageway for receiving and conducting the inner and outer vacuum conduits between the proximal inlet and the distal lead outlet (and ultimately to receive and conduct a lead with lead drive); (d) a first actuator adapted to articulate the inner suction foot portion and the outer suction foot portion while the inner suction foot portion is disposed within the outer suction foot portion; (e) a second actuator adapted to articulate the inner suction foot portion when the inner suction foot portion is extended from the outer suction foot portion; (f) an electrocautery blade extending from between the inner and outer suction foot portions; and (g) a waste removal tubular conduit adapted to conduct a vacuum to the distal end of the device. This variation may also include a lead drive having a flexible distal end and inserted within the inner tubular vacuum conduit so as to extend to the inner tubular vacuum conduit distal end, the flexible distal end bearing a lead extending through the lead drive head and having a lead distal end portion, the lead distal end portion extending from the distal end of the lead drive (and urged beyond the distal end of the inner tubular vacuum conduit) for contact with the epicardial surface of the heart. It also includes an electrocautery blade extending from between the inner and outer suction foot portions.

Vacuum Conduits—Articulation while Nested The inner and outer tubular vacuum conduits may be made flexible on their distal ends for instance through the use of a relatively thin portion of its tubular structure at the distal end as compared to the balance of its structure, through the use of a flexible material with tension cords incorporated into the balance of the tubular structure, and/or through the use of laminate or corrugated structures, hinges or flat spiral coils permitting the distal end to flex and thereby articulate. The inner and outer tubular vacuum conduits may be of any material appropriate for medical use, such as disposable plastics or sterilizable metals. The inner and outer tubular vacuum conduits may be of any configuration or cross-section not inconsistent with the described function, such as those of circular, ovoid, polygonal or even arcuate cross-section; and they may be made with telescoping portions where desirable. Accordingly, as used herein the term "conduit" should be understood as including the structures in the device with articulating distal ends and that serve to provide a course through which a vacuum may be conducted to the desired attachment site, and that, in the case of the relatively inner and relatively outer vacuum conduits, are hollow to allow them to be placed in the sliding arrangement with one another, and to slidingly conduct the waste vacuum conduit and the lead drive as described herein.

The contact or lead placement device of the present invention features dual nested suction feet (respectively disposed upon and directed by the first, relatively inner vacuum conduit and the second, relatively outer vacuum conduit), and provided with a vacuum through these cooperating nested vacuum conduits extending through the outer protective support sheath of the device. The inner and outer vacuum conduits are provided with at least one vacuum channel for independently conducting a vacuum to their respective vacuum feet, as well as being hollow to permit, in the case of the outer vacuum conduit, to engage and permit extension of the inner vacuum conduit therethrough (to permit the extension of the inner suction foot to a position distally beyond the outer suction foot) and, in the case of the inner vacuum conduit, to engage and permit extension of the waste vacuum conduit to an effective point in the nested structure to capture and permit withdrawal of tissue severed by the electrocautery blade at the position of the co-extended vacuum feet during operation.

The vacuum channel(s) may be in the form of captive tubules or equivalent chambers within the conduit structure, with the conduit structures being hollow so as to define a channel to permit them to be slidingly nested within one another as exemplified amplified by the described embodiments.

It will be appreciated that in another variation of the invention, that a flexible and resilient attachment portion may extend from the distal end of the inner vacuum conduit to the inner suction foot (being of sufficient strength to steer the inner suction foot), and thereby also serve as a flexible attachment permitting the inner suction foot to be articulated independently once extended from the outer suction foot. The flexible member in this embodiment, and its nature and operation, may be the same or equivalent to that described above with respect to other embodiments. Likewise, the actuator portion, and its nature and operation may be the same or equivalent to that described above with respect to other embodiments described herein.

Relative length of conduits/Spacer Preferably, where the inner tubular vacuum conduit is longer than the outer tubular vacuum conduit, the device may additionally comprise a spacer adapted to maintain the inner suction foot portion within the outer suction foot portion until the inner tubular vacuum conduit is ready to be extended further inside the chest, in the procedure as described here.

Actuators As may be appreciated from consideration of the construction of the described embodiments, the actuators may be any arrangement adapted to exert an articulating force through or around the inner and outer tubular vacuum conduit to being about articulation of the inner and outer suction feet.

The arrangement of the present invention permits the separate functionality of the relatively inner and outer tubular vacuum conduits, including independent articulation of the two tubular vacuum conduits, such as in two separate planes at right angles to each other.

The device also includes actuators that transmit movement to the dual suction feet, such as through deflection of these first, relatively inner and/or second, relatively outer lead vacuum conduits, so as to bring about articulation of the dual suction feet.

As an example, this may be done by using actuators to articulate the distal and relatively flexible portion of the second, relatively outer conduit, with the first, relatively inner conduit nested therein, so as to cause contemporaneous articulation of the distal and relatively flexible portion of the first, relatively inner vacuum conduit nested therein, and wherein the distal ends of the respective dual suction feet held substantially co-planar. The actuators may use any arrangement adapted to transmit a articulating forces from the operator's hand to the nested conduits and their vacuum feet, such as through the use of opposed spooled tension cords as described herein, or through the use of laminate or corrugated structures, hinges or flat spiral coils within the conduit structure permitting the distal ends thereof to flex and thereby articulate.

The device of the present invention thus provides actuators such as in the form of knob portions disposed on the proximal end portion, the knobs adapted to move respective actuators within the support sheath so as to articulate the outermost and relatively inner suction foot portions, including articulating the relatively inner suction foot portion once extended from within the distal portion of the outermost tubular vacuum conduit. The actuators may be in the form of tension cords attached to respective knob portions disposed on the proximal end portion, the knobs adapted to move the tension cords within inner and outer vacuum conduits held by the support sheath so as to articulate the respective inner and outer suction foot portions. In one embodiment, the inner and outer vacuum conduits each comprise a "flat coil" or equivalent mechanical arrangement permitting the rotation action of the knob (or other hand movement) to be translated into an articulating movement of the distal portion of the inner and outermost vacuum conduits such as by hand force transmitted from the knobs as described herein.

The device in one of its embodiments will comprise a hand-driven actuator, such as a knob, to permit the outermost vacuum conduit to be extended from the support sheath by hand, and to be articulated once extended therefrom while containing the relatively inner vacuum conduit.

In some embodiments the device includes a first actuator, such as comprising a knob adapted to articulate the inner suction foot portion and the outer suction foot portion while the inner suction foot portion is disposed within the outer suction foot portion, as well as a second actuator, such as comprising a knob adapted to articulate the inner suction foot portion when the inner suction foot portion is extended beyond the outer suction foot portion. The device thus also will include a hand-driven actuator, such as a knob or other manually operable arrangement, to permit the inner vacuum conduit to be articulated once extended from the support sheath by hand, to articulate the lead drive it guides through articulation in accordance with that of the inner suction foot. This may be done by providing the inner suction foot portion with an engagement aperture, and wherein the pacing lead head portion is adapted to releasably engage the engagement aperture, and to extend therefrom once the lead is placed, and the balance of the device is withdrawn, in the placement procedure.

The device of the present invention thus provides actuators such as in the form of knob portions disposed on the proximal end portion, the knobs adapted to move respective actuators so as to articulate the outermost and relatively inner suction foot portions, including articulating the relatively inner suction foot portion once extended from within the distal portion of the outermost tubular vacuum conduit, while being supported within the support sheath.

The actuators may be in the form of tension cords attached to respective knob portions disposed on the proximal end portion, the knobs adapted to move the tension cords within inner and outer vacuum conduits held by the support sheath so as to articulate the respective inner and outer suction foot portions. In one embodiment, the inner and outer vacuum conduits each comprise a "flat coil" or equivalent mechanical arrangement permitting the rotation action of the knob (or other hand movement) to be translated into an articulating movement of the distal portion of the inner and outermost vacuum conduits such as by hand force transmitted from the knobs as described herein.

Support Sheath The device of the present invention may include support sheath has a proximal end portion and a distal end portion, and has accordingly a proximal inlet and a distal lead outlet for extending the nested vacuum conduits therethrough along its longitudinal axis, so as to permit the vacuum conduits to be collectively supported and facilitate their sliding advancement toward and into the target site within the patient, including while the inner and outer vacuum conduits are advanced to the target site (such as to the pericardium), as the electrocautery blade cuts the tissue, as the waste removal vacuum advances within the inner vacuum conduit to remove the cut tissue, and as the inner vacuum conduit is advanced to have its inner suction foot be urged beyond the outer suction foot to the heart surface.

The support sheath may include a closure lid such as in the form of a moveable cover adapted to reversibly open and close the distal lead outlet, such as though use of a spring-urged closure arrangement.

In one embodiment, the support sheath may be provided with a handle portion extending laterally therefrom for ease of manual use, though it will be appreciated that the invention may be adapted for robotic use. The handle portion, such as a handle extending laterally from the support sheath, allows the operator to advance the device into the surgical site, and further articulate the inner and outer tubular vacuum guides allowing ultimately for the lead drive to insert the cardiac lead through operation of the lead placement device, as described herein. The handle of the sheath is adapted to allow attachment of a commercially available electrocautery pen, such that the electrocautery blade at the distal end between the outermost and relatively inner suction foot can be energized and activated from the handle of the sheath.

The support sheath may be of any length, but typically will have a lead receiving passageway that has a length in the range of 10 cm to 40 cm for manual devices, and preferably about 15 cm in length.

The Manifold/Bulkhead and Actuators The device of the present invention may be constructed to incorporate a manifold bulkhead construction relatively at or near the proximal end of the support sheath to provide physical support to the actuators (such as in the form of knobs), as well as where may be required, to incorporate apertures to permit effective through passage of actuator wires or cords connected to the knobs, to direct them proximally toward the distal end of the inner and outer vacuum feet.

The manifold or bulkhead structure may also be provided with fluid ports and channels to direct and conduct the three independent vacuum leads from the handle to the respective inner, outer and waste removal vacuum conduits.

Releasable Pacing Contact Head Another aspect of the present invention is to arrange and configure the first, relatively inner vacuum suction foot portion adapted to engage with the contact-placing head portion (whether as a lead-placing head portion or battery-bearing contact head portion) releasably attached to this first relatively inner suction foot portion while allowing the articulating movement of this first inner suction foot portion; the lead-placing head portion while being releasable through hand force to permit the lead-placing head portion lead to be separated from this first the inner suction foot portion after fixing the lead, contact or conduit in the tissue.

Lead Drive and Contact Head The lead drive used in accordance with the device of the present invention features a flexible distal end and a lead distal end portion with a pacing contact lead head from which extends a pacing lead. The lead drive is adapted and sized to be inserted within the relatively inner tubular vacuum conduit so as to extend to the relatively inner tubular vacuum conduit distal end where it may be engaged with the interior of the inner vacuum foot in a position to extend the pacing contact lead head beyond the inner vacuum foot for contact with, and ultimately for placement in, the epicardial surface of the heart during the placement procedure, as described herein.

As to the lead drive distal end, the lead drive may present the lead distal end such that it extends from the distal side of the lead drive (typically for about 1-2 mm in one embodiment) such that the tip of the lead comes in good contact with tissue such as the heart surface, to perform electrical assessment such as mapping), i.e., and also from the distal side of the relatively inner suction foot portion holding the lead drive head in place.

In one embodiment, the lead distal end is held by the lead drive so as to extend from the distal end of the lead drive, such as with a lead drive fixture at the distal end thereof. The lead drive will feature a flexible distal end portion to be able to follow the articulation of the inner and outer tubular vacuum conduits during operation as descried herein. The lead drive may be made flexible on its end for instance through the use of a flexible coil or through the use of a flexible material incorporated into the balance of the tubular structure.

Pacing Contact Lead Head and Suction Feet The present invention includes an arrangement including a pacing contact or lead placement head for a device along with cooperating suction feet, adapted for the thoracoscopic placement of a lead at a target site on an epicardial surface of a heart. Such an arrangement comprises: (a) an inner suction foot portion adapted to conduct a first independent vacuum to an inner area of a target site; (b) an outer suction foot portion adapted to conduct a second independent vacuum to an outer area of a target site, the inner suction foot portion and the outer suction foot portion having a longitudinal axis, and being in sliding engagement with one another such that the inner suction foot portion can be extended from the outer suction foot portion along the longitudinal axis, and (c) a pacing contact or lead placement head releasably attached to the inner suction foot portion, and having a pacing lead extending therefrom. This arrangement may also include:

(d) an electrocautery blade extending from between the inner and outer suction foot portions; and (e) a waste removal vacuum conduit adapted to direct a third independent vacuum within the inner suction foot portion.

Foot Shape Also in the many embodiments described herein, the inner and outer suction foot portions may be of any shape, such as presenting a round, polygonal, star or ovoid foot print, though it is preferred that it have a round or other radially symmetric footprint shape, and may comprise a plurality of air channels in fluid contact with the respective inner and outer tubular vacuum conduits, so as to be capable of providing suction to the respective suction foot portions.

It is also optional that the relatively inner and/or outer suction foot portion(s) comprise(s) a plurality of cups connected to air channels, so as to be capable of providing suction to the suction foot portion(s), and in one embodiment the inner and outer suction foot portions may comprise a plurality of suction areas or cups connected to air channels, so as to be capable of providing suction to the relatively inner suction foot portion to stabilize the device prior to lead testing and/or insertion.

The device in one embodiment also includes an electrocautery blade extending from between the inner and outer suction foot portions.

Vacuum Sources The device of the present invention may be a part of a system that additionally comprises a source of vacuum suction in fluid communication with the inner and outer vacuum conduits and thus to their suction feet, as well as a source of vacuum suction provided to the waste vacuum conduit.

With respect to the vacuum conduits and vacuum source for use in the invention in its many embodiments, the device may additionally comprise a source of vacuum suction in fluid communication with the vacuum conduits. The source of vacuum suction in fluid communication with the vacuum conduits may be any source sufficient for operation of the device, and typically may be selected from the group consisting of a hand pump, or a syringe attached to the support sheath, or a motorized pump supplying vacuum suction to the respective inner and outer suction foot portions which in turn may be connected to the proximal, operator end of inner tubular vacuum conduit, and regulated by any appropriate fluid control device or valve, including valves or stop-cocks.

The source of vacuum suction may be introduced to a manifold, such as may be placed in the device handle to control and distribute vacuum suction independently to each subassembly of the device as exemplified herein.

Movement-Restrictive Spacer In one of its embodiments, the device of the present invention additionally comprises a removable spacer adapted to maintain the position of the inner suction foot portion with respect to the outer suction foot portion in which case the inner vacuum conduit is longer that the outer vacuum conduit, such as described in the Figures.

Handle The device may be provided with a handle portion extending laterally directly or indirectly from the support sheath for manual operation, but otherwise may be adapted for robotic use in association with a robotic arm to which it may be readily adapted.

The handle may also be provided with a set screw or mechanical adaptation to hold the outer tubular vacuum conduit with its nested vacuum conduits in a set position with respect to the support sheath to better secure the device during use.

Referring to the handle portion, it may have a lower portion and an upper portion, and a longitudinal axis, and defining a space adapted to accommodate and support an electrosurgical pencil therein; and (1) an electrosurgical pencil disposed within the space and having an electric input contact extending from the lower portion of the handle, and an electric output contact extending from upper portion of the handle; (2) a hollow electrocautery sheath extending from the upper portion at an angle to the longitudinal axis, the hollow electrocautery sheath having a rotatable electrocautery connection, and (3) an electrical connection between the electrosurgical pencil and the electric output to the rotatable electrocautery connection.

The handle may be provided with a vacuum manifold adapted to accept a vacuum connection, and distribute it independently to each of the vacuum conduits. In one embodiment, the handle portion generally has a lower portion and an upper portion, with the lower portion comprising a vacuum manifold adapted to accepted a vacuum connection and to distribute the vacuum independently respectively to each of the (a) inner tubular vacuum conduit, (b) outer tubular vacuum conduit and (c) waste removal vacuum conduit; and the vacuum manifold may comprise three respective push valves governing the vacuum connections to each of the vacuum conduits.

Summary of the Subassemblies

The present inventions also include the subassemblies of the device of the present invention, as well as their mechanical arrangements.

Manifold Bulkhead on Support Sheath with Vacuum and Electrocautery Blade; Electrocautery Subassembly Attached to Electrocautery Blade The device may also feature, on the proximal end of the support sheath, a proximal bulkhead, and wherein: (i) a first of the at least one actuator comprises a first captive articulation knob extending into the proximal bulkhead and having a first spool portion having a spool of first articulation wires; (ii) a second of the at least one actuator comprises a second captive articulation knob extending into the proximal bulkhead and having a second spool portion having a spool of second articulation wires. The proximal bulkhead comprises: (i) a first opposed aperture pair having the first articulation wires extending therethrough; (ii) a second opposed aperture pair having the second articulation wires extending therethrough; and (iii) at least one fluid aperture adapted to transmit a vacuum through the proximal bulkhead. The outer tubular vacuum conduit extending from the proximal bulkhead a first length; and the inner tubular vacuum conduit of sufficient length so as to be adapted to extend from the proximal bulkhead a second length greater than the first length. This arrangement also includes a hollow electrocautery sheath extending from the proximal bulkhead, the hollow electrocautery sheath having a rotatable electrocautery connection, and a spring extending from the distal end of the hollow electrocautery sheath to the electrocautery blade.

Electrocautery Assembly

The device may also feature a rotatable electrocautery assembly comprising a hollow outer electrocautery sheath having a distal end and a proximal end; a rotational knob assembly disposed on distal end of the hollow outer sheath, the rotational knob assembly having an outer shell attached to the proximal end of the hollow outer electrocautery sheath, and having a proximal inner surface and a distal inner surface, and maintaining captive: (i) a floating ring disposed rotatably against the distal inner surface and having a floating ring inner surface and a conductive pin aperture;

(ii) a circular conductive contact ring disposed rotatably along the floating ring inner surface, and having conductive pin extending distally through the conductive pin aperture; and (iii) a plurality of springs positioned so as to urge the circular conductive contact ring against the floating ring inner surface; whereby the floating ring and circular conductive contact ring can rotate within the outer shell while the conductive pin extends distally through the conductive pin aperture.

Lead and Lead Head It will be appreciated that the lead itself may be incorporated into supplementary structure for ancillary purposes such as electrical insulation and to be able to mechanically cooperate with the balance of the device and consistent with its function as described herein (such as by providing sleeves and flanges, etc.) One such arrangement involves having the lead distal end being held by a lead head portion (typically of a polymeric material) so as to extend from the distal side of the lead head portion.

Lead Drive The lead drive may also additionally comprise an interferant release collar attached to the inner tubular vacuum conduit distal end portion and disposed on the distal side of the inner guide suction foot portion, the interferant release collar being larger than the aperture. This allows more precise and oriented lead placement through advancement of the lead head portion distally from the inner tubular vacuum conduit, while preventing accidental or premature retraction of the lead head portion, as described herein.

The actuator of the preferred embodiment of the present invention may comprise a flexible member connecting the suction foot portion to the support sheath. This flexible member may be any part of sufficient flexibility and resilience to permit the suction foot to articulate as described herein. For instance, the flexible member may be in the form of a metal or plastic spring or coil, or equivalent metal or plastic structure.

In one embodiment, the actuators are in turn attached to respective knobs disposed on the proximal end portion of the device (such as by being connected to the handle to provide static support), the knobs adapted to move the actuators within the inner and outer tubular vacuum conduits (once extended from the support sheath), so as to articulate the inner and outer suction feet at their respective ends in unison (prior to the extension of the inner tubular vacuum conduit from within the outer tubular vacuum conduit), as well as to articulate the inner tubular vacuum conduit independently (and thereby the inner suction foot, to provide an articulated path along which the distal end of the lead drive advances as described herein), once extended from the outer tubular vacuum conduit.

Actuators The actuator(s) may be any part of sufficient flexibility and resilience to facilitate the movement of the suction feet to articulate as described herein. For instance, it is preferred that each actuator comprise one or more tension cords attached to a knob portion disposed on the proximal end portion, the knob adapted to move the inner and outer vacuum conduits within the support sheath so as to articulate the suction foot.

Ancillary tube structure The device of the present invention may optionally include one or more tubular structures extending through the vacuum conduits and extending between the proximal inlet and the distal outlet. In one embodiment, in both the inner and outer vacuum conduits, the vacuum or negative pressure traverses through the shell of the relatively rigid, proximal portion of the tubes, and then through a relatively flexible tube to the suction foot in the articulating distal portion of the tubes, as shown in the diagrams.

Test Lead The device of the present invention may also include a supplementary test lead extending from any effective portion of the device, such as from the contact head portion (whether lead- or battery energized) and through the support sheath.

Use with other devices Another aspect of the present invention is a pacing contact placement device with an articulating suction foot as represented, for instance, by the preferred embodiments described herein. It will be appreciated that this aspect of the invention may be constructed and used in other devices beyond that described in one embodiment herein.

Electrocautery blade The electrocautery blade may be in the form of a blade extending from a conductive spring to permit it to accommodate some compression with the assembly, as well as to allow the electrocautery blade to be advanced (such as may be facilitated through threads or threadlike structures within the assembly such as described herein), while still being able to extend from between the outer and the inner tubular vacuum conduits such as those in the form of inner and outer vacuum feet as described herein.

Pacing Contact and Head Still another aspect of the present invention is a lead placement device with suction foot and releasable contact head and lead (or battery), wherein the device may be adapted for use with any tissue type and for the placement of any conduit type (such as conduit of electrical current or signals, or gas or liquid fluids conduits) for any medical or veterinary purpose.

Locking mechanism Other features and embodiments of the device of the present invention may include a locking mechanism adapted to restrict the axial movement of the inner tubular vacuum conduit with respect to the outer tubular vacuum conduit, such as by restricting the axial movement of the inner vacuum foot with respect to the outer vacuum foot, to prevent this movement prior to the appropriate point in the procedure as described herein. This may be done through any mechanical arrangement such as where opposing surfaces of a portion of the nested inner vacuum foot and outer vacuum foot are provided with a locking arrangement featuring a tab-and-channel locking arrangement wherein a tab extending from one surface that restricts movement by being in an interfering relationship with a the opposed surface, which can be released upon turning one conduit/foot with respect to the other, such that the tab may becomes aligned opposite a channel that permits the tab to move distally and thus its supporting surface to be moved longitudinally with respect to the opposed surface.

Hollow multi-vacuum foot arrangement Another aspect of the present invention is the vacuum foot and waste conduit arrangement. The vacuum foot arrangement of the present invention includes: (a) a hollow outer suction foot portion provided with at least one vacuum channel adapted to conduct a vacuum its distal end outer suction foot surface, (b) a hollow inner suction foot portion provided with at least one vacuum channel adapted to conduct a vacuum its distal suction foot surface portion while being slidingly engaged within the hollow outer suction foot portion, such that its suction surface may be moved from a position even with the distal suction surface of the outer suction foot portion to a position beyond the distal suction surface of the outer suction foot portion, and (c) a waste vacuum conduit having a distal suction end and slidingly engaged within the hollow inner suction foot portion, so as to be moveable from a position proximal of the distal suction surface of the outer suction foot portion to a position beyond the distal suction surface of the outer suction foot portion.

Biopsy variant The device of the present invention also may be appreciated as including a variant being adapted for the placement or insertion of a conduit at a target site on a tissue surface, such as for biopsy or injection of medicine into the target site. In this embodiment, the lead, contact head and pacing contact may be replaced with a fluid conduit in the same position, to permit withdrawal or injection of a fluid at the target site. The fluid conduits may be selected from the group consisting of liquid and gas conduits, such as conductive materials such as wires or fluid-conductive tubules, such conduits adapted to be placed into tissues for electrical or fluid assay and/or biopsy, electrical or fluid testing, electrical actuation, or otherwise to bring about electrical or fluid influence or to determine the level of same. Preferably, such conduits will include coiled plastic or metal tubules or a combination of such materials.

This aspect of the present invention may be described as a device adapted for the thoracoscopic placement of a lead at a target site on an epicardial surface of a heart (though it may also be used with other tissues or organs and other purposes, such as biopsy, stent or tubule placement, etc. by substituting the cardiac lead with an alternative with the desired biopsy needle, stent or tubule placement arrangement, as desired, especially where it is desirable or beneficial to remove tissue in advance of reaching a target site on the tissue or organ of interest). This device is essentially the same as the device described herein with the exception that the cardiac lead is replaced by a biopsy needle, stent or tubule placement arrangement, in which case the electronic connection used in the pacing contact device may be replaced with an additional vacuum or pump arrangement to inject, insert or remove medications, other therapeutic or assay-related substances or materials, tissue, fluids or the like.

Methods

The present invention also includes a method of cardiac lead placement with articulating suction foot and releasable cardiac lead. The present invention in general terms comprises a method for the thoracoscopic placement of a lead at a target site on an epicardial surface beyond pericardium tissue of a heart of a human or animal, the method comprising: (a) extending into the pericardial region a device comprising: (1) an inner tubular vacuum conduit having an inner vacuum conduit distal end comprising an inner suction foot portion, the inner tubular vacuum conduit being flexible and adapted to conduct a vacuum to the inner suction foot portion; (2) a lead head portion connected to the lead guide distal end; (3) a lead extending through the lead head portion and having a lead distal end, the lead distal end extending from the inner tubular vacuum conduit distal end for contact with the epicardial surface of the heart; (4) an outer tubular vacuum conduit having an outer vacuum conduit distal end comprising an outer suction foot portion, the outer tubular vacuum conduit being flexible and adapted to conduct a vacuum to the outer suction foot portion while being adapted to slidingly conduct the inner tubular vacuum conduit, so as to permit the inner tubular vacuum conduit to be extended from the outer vacuum conduit distal end; (5) a support sheath having a longitudinal axis, a proximal end portion and a distal end portion, and having a proximal inlet and a distal lead outlet for extending the inner and outer vacuum conduits therethrough, the support sheath comprising a lead receiving passageway for receiving and conducting the inner and outer vacuum conduits between the proximal inlet and the distal lead outlet, the lead head portion adapted to releasably engage the inner suction foot portion such that such engagement is of sufficient strength to maintain the position of the lead distal end portion as it engages the epicardial surface of a heart, and sufficiently releasable such that the lead head portion may be released from the inner suction foot portion once the lead is attached to the epicardial surface of a heart; and (6) a first actuator extending from the proximal end portion to the distal end portion and adapted to articulate the outer suction foot portion; and (7) a second actuator extending from the proximal end portion to the distal end portion and adapted to articulate the inner suction foot portion; (8) an electrocautery blade extendable from between the outer and the inner tubular vacuum conduits; and (b) positioning the inner and outer suction foot portions upon the pericardium tissue, the inner and outer suction foot portions being maintained substantially co-planar to one another; (c) applying suction through the inner and outer tubular vacuum conduits so as to stabilize the inner and outer suction foot portions against the pericardium tissue; (d) cutting a portion of the pericardium tissue while securing the portion of the pericardium tissue to the inner suction foot portion; (e) engaging the vacuum of the waste removal tubular conduit so as to remove the portion of the pericardium tissue from the pericardial region; (f) after loading the lead with lead drive into the inner tubular vacuum conduit, (extending the inner suction foot portion beyond the plane of the outer suction foot portion); (g) inserting the lead distal end portion into the epicardial surface; (h) disengaging the lead head portion from the inner suction foot portion; and (i) releasing the lead from the lead drive; and (j) withdrawing the device from the pericardial region, whereby to leave the lead attached to the epicardial surface.

A corresponding method may be adapted for biopsy or treatment in accordance with the construction of the biopsy or injection variant device.

The foregoing and other objects, features, and advantages of this invention will become more readily apparent from the following detailed description of a preferred embodiment which proceeds with reference to the accompanying drawings, wherein one embodiment of the invention is shown and described, simply by way of illustration of the best mode contemplated of carrying out the invention.

As will be realized, the invention is capable of other and different embodiments, and its several details are capable of modifications in various obvious respects, all without departing from the invention. Accordingly, the drawings and description are to be regarded as illustrative in nature, and not as restrictive. It will also be appreciated that the detailed description represents one embodiment of the invention, and that individual steps of the process of the invention may be practiced independently so as to achieve similar results.

BRIEF DESCRIPTION OF THE DRAWINGS

FIG. 4 is a partially sectioned and transparent distal end perspective view of an outer sheath subassembly for a device in accordance with one embodiment of the present invention.

FIG. 7 is a detailed first lateral elevation view of a proximal end housing of the outer sheath of a device in accordance with one embodiment of the present invention.

FIG. 8 is a sectioned distal perspective view of a proximal end housing of the outer sheath of a device in accordance with one embodiment of the present invention.

FIG. 9 is a partially sectioned and transparent lateral view of a proximal end housing of the outer sheath of a device in accordance with one embodiment of the present invention.

FIG. 10 is a partially sectioned perspective view of an articulation control knob and spool of the outer sheath of a device in accordance with one embodiment of the present invention.

FIG. 11 is a partially sectioned perspective view of an articulation control knob and spool positioned on a proximal end housing of the outer sheath of a device in accordance with one embodiment of the present invention.

FIG. 12 is a top perspective view of an articulation control knob of the outer sheath of a device in accordance with one embodiment of the present invention.

FIG. 13 is a first perspective partially transparent view of the proximal end of an electrocautery blade subassembly of a device, in accordance with one embodiment of the present invention.

FIG. 14 is a partially sectioned and transparent first perspective view of the proximal end of an electrocautery blade subassembly of a device in accordance with one embodiment of the present invention.

FIG. 16 is a detailed sectioned first perspective view of the proximal end of an electrocautery blade subassembly of a device in accordance with one embodiment of the present invention.

FIG. 17 is a detailed perspective view of the distal end of an electrocautery blade subassembly of a device in accordance with one embodiment of the present invention.

FIG. 18 is a partially sectioned distal end perspective view of distal end of an inner vacuum subassembly of a device in accordance with one embodiment of the present invention.

FIG. 19 is a partially transparent perspective view of an inner vacuum subassembly of a device, with vacuum connector, in accordance with one embodiment of the present invention.

FIG. 20 is a partially sectioned and transparent distal end perspective view of the distal end of an inner vacuum subassembly of a device in accordance with one embodiment of the present invention.

FIG. 21 is a partially transparent perspective view of an inner vacuum subassembly of a device, with vacuum connector, in accordance with one embodiment of the present invention.

FIG. 25 is a partially sectioned and transparent distal end perspective view of the proximal end of a lead drive of a device in accordance with one embodiment of the present invention.

FIG. 26 is a distal end elevation view of the distal end of a lead drive subassembly of a device in accordance with one embodiment of the present invention, and also showing the distal end of the lead drive adaptation to securely hold the lead or contact head in place.

FIG. 27 is a distal end lateral perspective view of the distal end of a lead drive subassembly of a device in accordance with one embodiment of the present invention.

FIG. 35 is a detailed partial lateral perspective view of an elongated handle sheath subassembly with electrocautery pen and suction tube in accordance with one embodiment of the present invention.

FIG. 36 is a detailed partially sectioned and transparent lateral elevation view of an elongated handle sheath subassembly with control knobs with electrocautery connection for a device in accordance with one embodiment of the present invention.

FIG. 37 is a detailed partially sectioned and transparent lateral elevation view of the distal end of a device in accordance with one embodiment of the present invention, with the electrocautery blade inside.

FIG. 38 is a detailed partially sectioned and transparent lateral elevation view of the distal end of a device showing the advancement of electrocautery blade with rotation in accordance with one embodiment of the present invention.

FIG. 39 is a detailed partially sectioned and transparent lateral elevation view of an elongated handle sheath subassembly with control knobs, and depicting rotation of electrocautery knob for a device in accordance with one embodiment of the present invention.

FIG. 40 is a detailed partially sectioned and transparent lateral elevation view of the distal end of a device in accordance with one embodiment of the present invention.

FIG. 41 is a detailed partially sectioned and transparent lateral elevation view of the distal end of a device in accordance with one embodiment of the present invention.

FIG. 42 is a detailed partial lateral perspective view of an elongated handle sheath subassembly with control knobs and vacuum conduits for a device in accordance with one embodiment of the present invention.

FIG. 43 is a detailed partial lateral perspective view of an elongated handle sheath subassembly with control knobs and vacuum conduits for a device in accordance with one embodiment of the present invention.

FIG. 44 is a detailed partial lateral perspective view of an elongated handle sheath subassembly with control knobs and vacuum conduits for a device in accordance with one embodiment of the present invention.

FIG. 45 is a detailed partially transparent lateral perspective view of the proximal end of an inner vacuum handle and lead drive assembly of a device in accordance with one embodiment of the present invention.

FIG. 46 is a detailed partially transparent proximal end perspective view of the proximal end of an inner vacuum handle and lead drive assembly of a device in accordance with one embodiment of the present invention.

FIG. 47 is a detailed partially transparent first lateral elevation view of the proximal end of an inner vacuum handle and lead drive assembly of a device in accordance with one embodiment of the present invention.

FIG. 48 is a detailed partially transparent second lateral elevation view of the proximal end of an inner vacuum handle and lead drive assembly of a device in accordance with one embodiment of the present invention.

FIG. 49 is a distal end elevation view of the distal end of a device arrangement, with outer vacuum conduit, inner vacuum conduit and lead drive cooperating, in accordance with one embodiment of the present invention.

FIG. 50 is a distal end elevation view of the distal end of a device arrangement, with outer vacuum conduit, inner vacuum conduit and lead drive cooperating, in accordance with one embodiment of the present invention.

FIG. 51 is a detailed first lateral elevation view of the proximal end of an outer and inner vacuum handle and lead drive assembly of a device in accordance with one embodiment of the present invention.

FIG. 52 is a detailed first lateral elevation view of the proximal end of an outer and inner vacuum conduit handle and lead drive assembly of a device in accordance with one embodiment of the present invention.

FIG. 53 is a detailed partially transparent lateral perspective view of the distal end outer and inner vacuum conduit handle and lead drive assembly of a device in accordance with one embodiment of the present invention.

FIG. 54 is a detailed lower lateral perspective view of the proximal end of an outer and inner vacuum conduit handle and lead drive assembly of a device in accordance with one embodiment of the present invention.

FIG. 55 is a detailed lower lateral perspective view of the proximal end of an outer and inner vacuum conduit handle and lead drive assembly of a device in accordance with one embodiment of the present invention.

FIG. 56 is a detailed first lateral elevation view of the proximal end of an outer and inner vacuum conduit handle and lead drive assembly of a device in accordance with one embodiment of the present invention.

FIG. 57 is a detailed first lateral elevation view of the proximal end of an outer and inner vacuum conduit handle and lead drive assembly of a device in accordance with one embodiment of the present invention.

FIG. 58 is a detailed partially transparent lateral perspective view of the distal end of outer and inner vacuum conduit handle and lead drive assembly of a device in accordance with one embodiment of the present invention.

FIG. 59 is a detailed partially sectioned and transparent lateral elevation view of the distal end of an outer and inner vacuum conduit handle and lead drive assembly of a device in accordance with one embodiment of the present invention.

FIG. 60 is a detailed partially sectioned and transparent lateral elevation view of the distal end of an outer and inner vacuum handle and lead drive assembly of a device in accordance with one embodiment of the present invention.

FIG. 61 is a detailed first lateral elevation view of the proximal end of an outer and inner vacuum conduit handle and lead drive assembly of a device in accordance with one embodiment of the present invention.

FIG. 62 is a detailed partially transparent lateral perspective view of the distal end of an outer and inner vacuum conduit handle and lead drive assembly of a device in accordance with one embodiment of the present invention.

FIG. 63 is a detailed first lateral elevation view of the proximal end of an outer and inner vacuum conduit handle and lead drive assembly of a device in accordance with one embodiment of the present invention.

FIG. 64 is a detailed partially transparent lateral perspective view of the distal end of an outer and inner vacuum conduit handle and lead drive assembly of a device in accordance with one embodiment of the present invention.

DETAILED DESCRIPTION OF THE PREFERRED EMBODIMENTS

In accordance with the foregoing summary, the following provides a detailed description of the preferred embodiments, which are presently considered to be the respective best modes thereof.

As used herein the distal end refers to the working end or patient end, while the proximal end refers to the operator end or actuator end from which the device of the present invention may be operated. The handle as shown in the described embodiment is on the side of the device referred to as the bottom side or the ventral aspect. The side opposite the bottom side is referred to as the top side or dorsal aspect. The right side is the side on the right hand when looking from the operator end, end-on. Conversely, the left side is the side on the left hand when looking from the operator end, end-on.

Figure 1:
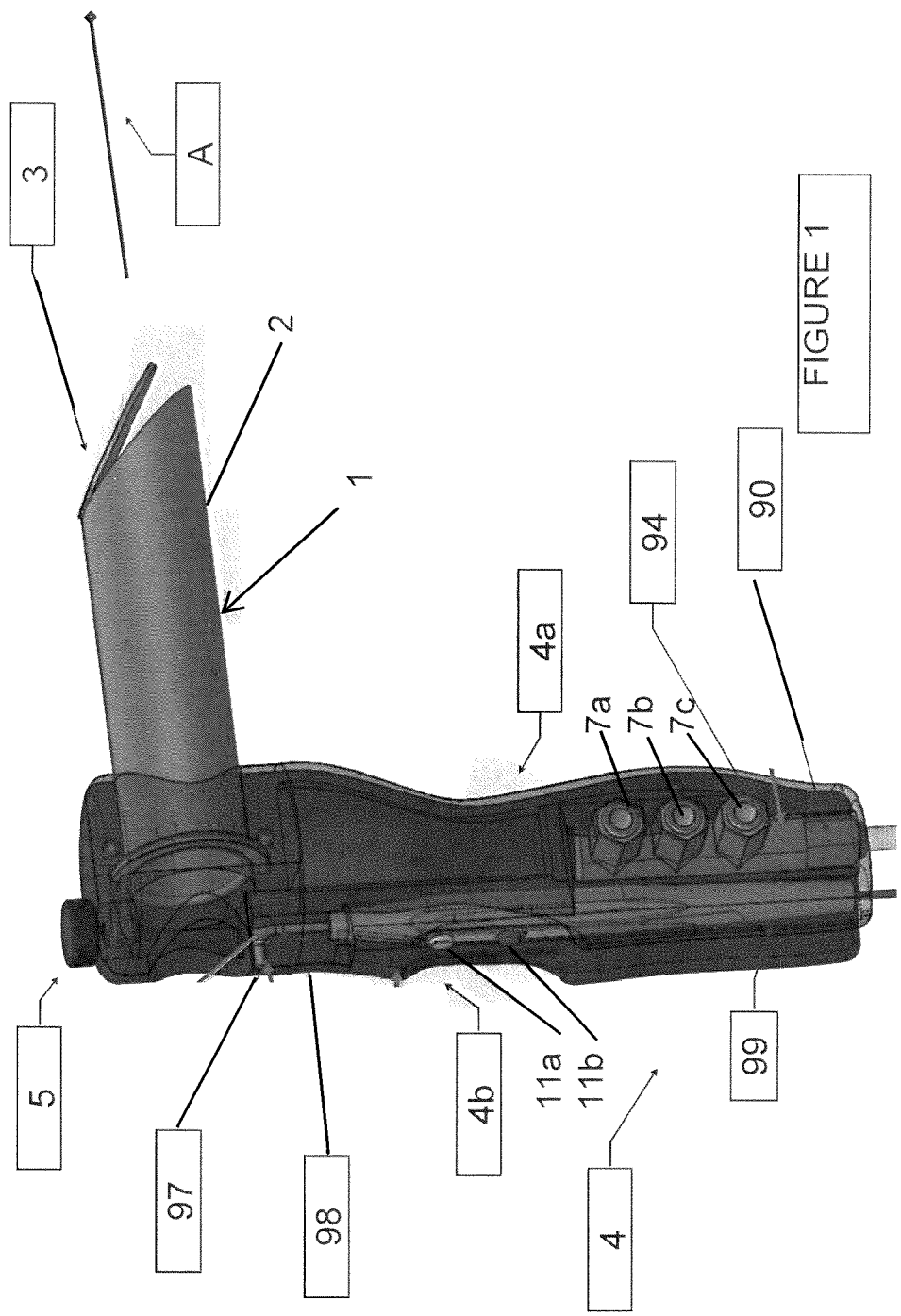
FIG. 1 is a partially sectioned and transparent first side lateral perspective view of an elongated handle sheath subassembly for a device in accordance with one embodiment of the present invention.

FIG. 1 is a partially sectioned and transparent first side lateral perspective view of an elongated handle sheath subassembly for a device in accordance with the displayed embodiment of the present invention. FIG. 1 shows of a support sheath 1 for a device in accordance with one embodiment of the present invention, having longitudinal axis A extending from the proximal to distal end. The displayed embodiment shows how a commercially available electrocautery pen may be fit into the handle. It also shows the outside suction attaches to the lower end of the handle. Inside the ergonomic handle the main suction line splits into 3 lines which opens on the side of the handle with "push to connect" adaptors. Suction or vacuum line for each of the three vacuum tubes can be individually connected or disconnected to the handle. When disconnected, the self-locking "push to connect" adaptor closes up to halt the vacuum.

The support sheath 8071 1 has a beveled distal end 8071*a* 2 with a spring biased door or cover 8030 3. It has a handle 8095 4 to be grasped by the operator, in this embodiment comprising right- and left-hand handle portions 4*a* and 4*b*. The right- and left-hand handle portions 4*a* and 4*b* are shaped so as to accommodate and support commercially available electrosurgical pencil 99.

In the displayed embodiment, the sheath 8071 1 is about 15 cms long, and forms a hollow probe made of solid unyielding material such as metal or hard plastic, to gain access into the chest cavity through the access incision in between the ribs. It also has a set screw 5 on the top surface of the operator end. This set screw when tightened will hold the outer vacuum tube in a set position (see e.g., FIGS. 31-34).

FIG. 1 also shows main vacuum connector 90 that attaches to external line vacuum, such as provided in an operating suite, and manifold 94 that distributes the vacuum to the three vacuum conduits included in the device such as by way of the self-locking "push to connect" adaptor.

FIG. 1 also shows some of the electric components of the device, such as connector wire 97 and adapter 98 that serve to facilitate the electric connection to the electrocautery blade of the device.

Figure 2:
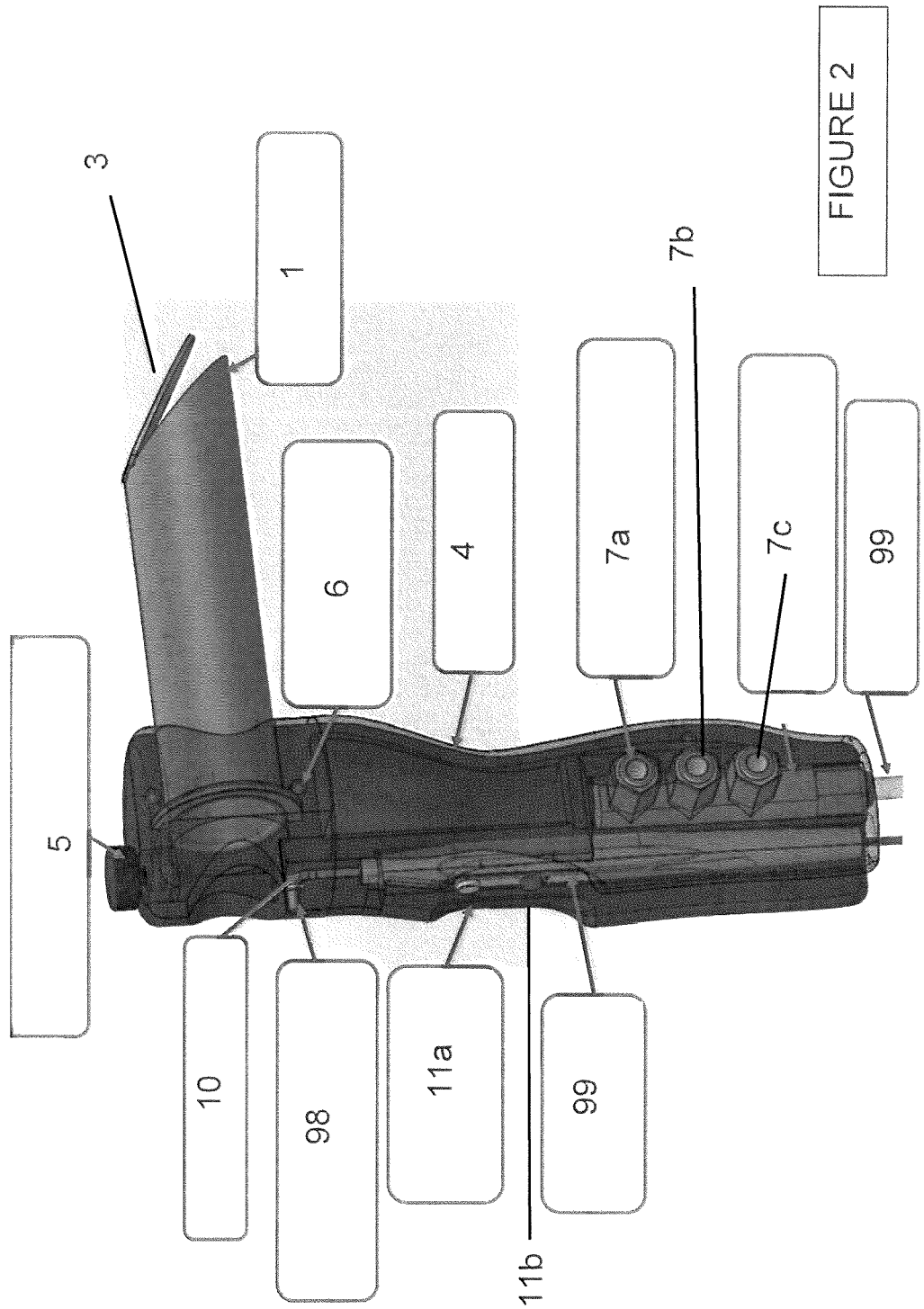
FIG. 2 is a partially sectioned and transparent first side lateral perspective view of an elongated handle sheath subassembly for a device in accordance with one embodiment of the present invention.

FIG. 2 is a partially sectioned and transparent first side lateral perspective view of an elongated handle sheath subassembly for a device in this embodiment of the present invention. FIG. 2 shows the device of FIG. 1, and further describes some of its features, components and component functions, including the set screw 5 to lock position of inserted tubing of the vacuum/electrocautery blade components, the standard diameter connector 10 to the commercially available electrosurgical pencil 99, the open adapter 98 to accept connection from device's electrocautery handle. The indent in handle's shape is to allow the buttons 11*a* and 11*b* to be pressed by the operator. FIG. 2 also shows the position of the commercially available electrosurgical pencil, and the introducer with the flip open cover 3.

Figure 2A:
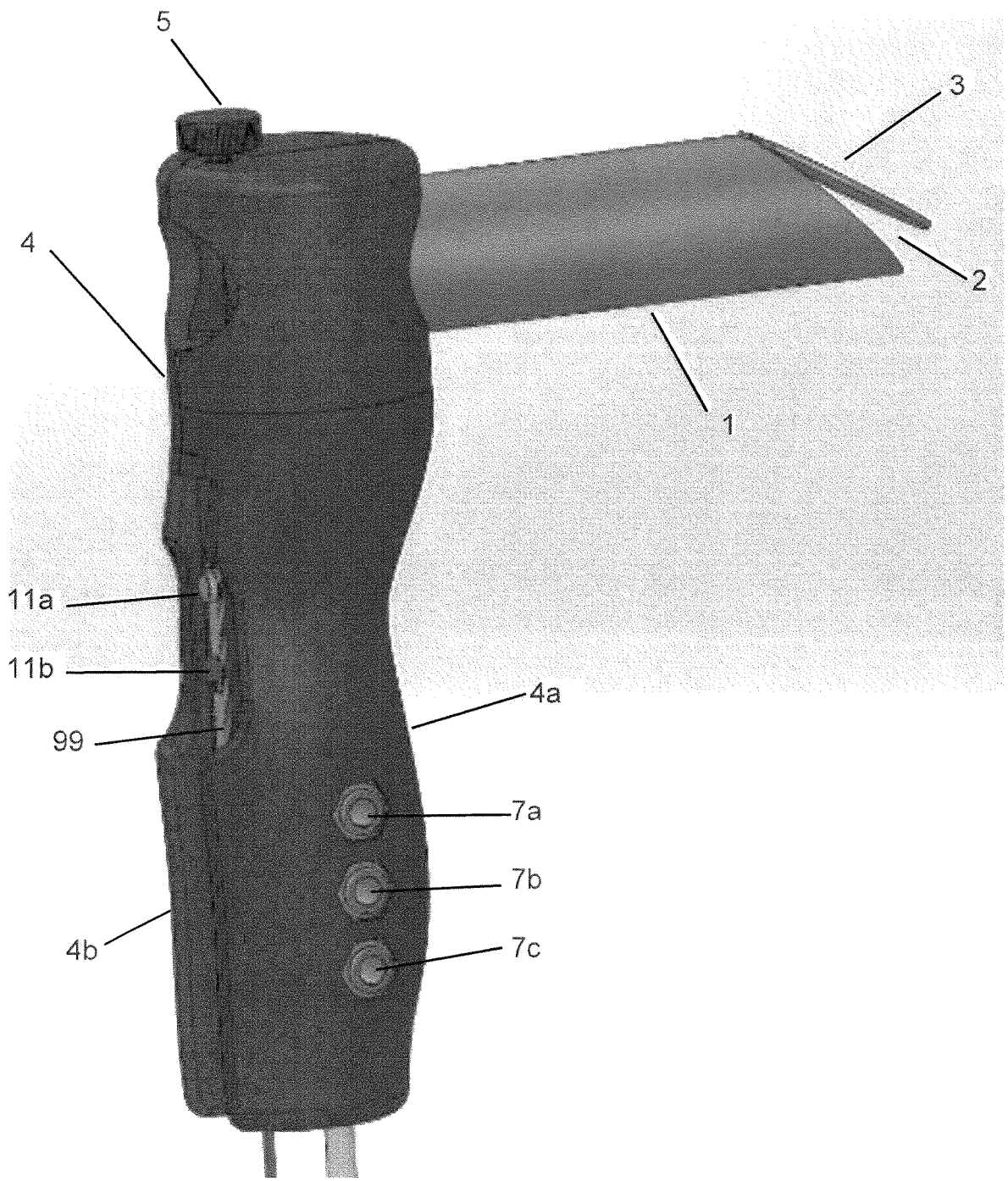
FIG. 2a is a first side lateral perspective view of the same.

FIG. 2 shows the position of two of the three screws 6 used to connect the right-hand 4*a* and left-hand 4*b* sides of the handle 4 which may have any appropriate shape, and which typically will have an ergonomic shape adapted to fit the hand of the operator. FIG. 2 also shows the quick-release valves 7*a*, 7*b* and 7*c* that operate by way of self-locking "push to connect" adaptors, which may incorporate an auto-shut-off valve feature when disconnected. FIG. 2 also shows that the manifold line connector line 90 may connect to wall vacuum (or portable vacuum source) input to three outputs for the device, such as, for example a ¼" OD connector 9 to wall vacuum. FIG. 2*a* is a first side lateral perspective view of the device shown in FIG. 2 without sectioning and wherein like numbers are used to indicate the same structure or features described above.

Figure 3:
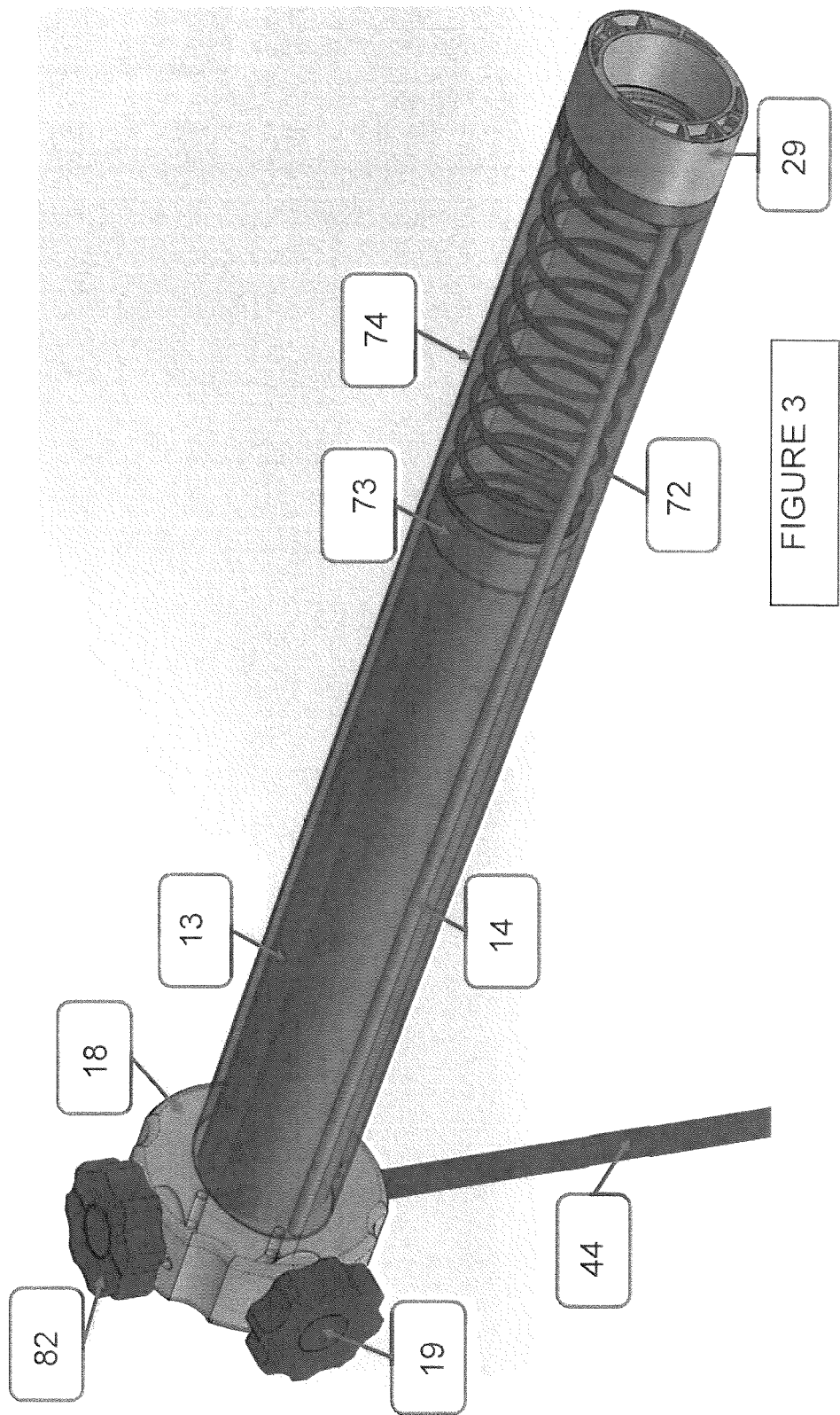
FIG. 3 is a partially sectioned and transparent distal end perspective view of an outer sheath subassembly for a device in accordance with one embodiment of the present invention.

FIG. 3 is a partially sectioned and transparent distal end perspective view of an outer sheath subassembly for a device in accordance with the displayed embodiment of the present invention. FIG. 3 shows outer conduit straight tube 13, vacuum air hose or tubing 14, oval suction foot 29, outer proximal end manifold bulkhead 18 of the device, spool knob 19, pulley knob 82, outer vacuum connector, outer spring 72, inner sleeve 73 and mesh sleeve 74. The proximal end manifold bulkhead 18 of the device supports spool knob 19 and pulley knob 82 and allows their rotation, so as to be able to actuate respective articulation wires (not pictured).

FIG. 4 is a partially sectioned and transparent distal end perspective view of an outer vacuum conduit subassembly for a device of this embodiment of the present invention. FIG. 4 shows manifold bulkhead 18 and outer conduit straight tube 13 which may include mesh sleeve 74.

FIG. 4 shows articulation spool knob 19 that may be rotated to provide side to side articulation and articulation pulley knob 82 that may be rotated to provide up-down articulation. Also shown is the ¼" OD connector to the handle, and vacuum air hose or tubing 14 that supplies vacuum pressure to end effector, and outer spring 72 that allows for articulation flexibility. As may be appreciated from this Figure, the suction foot 29 supplies vacuum force to the area to secure the device to the target tissue site, such as the pericardium. As can be seen in this Figure, vacuum or suction foot 29 has outer suction area 29*a*, conduit aperture 29*b*, locking tabs 29*c* and outer suction foot vacuum hose attachment apertures 29*f*.

In one such embodiment, mesh sleeve 74 protects the device components in the distal articulating portion.

Figure 5:
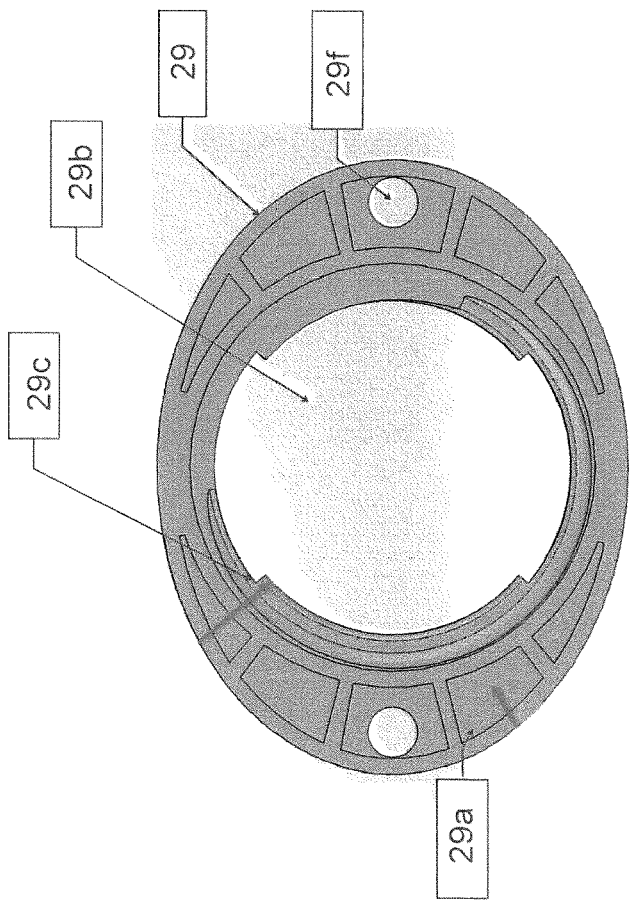
FIG. 5 is detailed plan distal end view of a vacuum foot portion of the outer sheath of a device in accordance with one embodiment of the present invention.

FIG. 5 is a detailed plan distal end view of an outer vacuum or suction foot portion 29 of a device in accordance with this embodiment of the present invention. FIG. 5 shows an oval variant of the outer suction foot 29.

FIG. 5 also shows locking tabs 29*c* to hold the position of inner suction foot portion with respect to outer suction foot portion 29. The tabs cooperate with corresponding locking tabs structure 62*a* on the outer surface of the inner vacuum foot surface to permit the two suction feet to move with respect to one another once the inner suction foot is rotated with respect to outer suction foot portion.

Application of vacuum to outer suction foot portion 29 causes vacuum area 29*a* to be secured against the target tissue area, such as for securement to the pericardium. In the displayed embodiment, an oval shape of outer suction foot portion 29 may be used to maximize vacuum area, though other shapes may be used.

Figure 6:
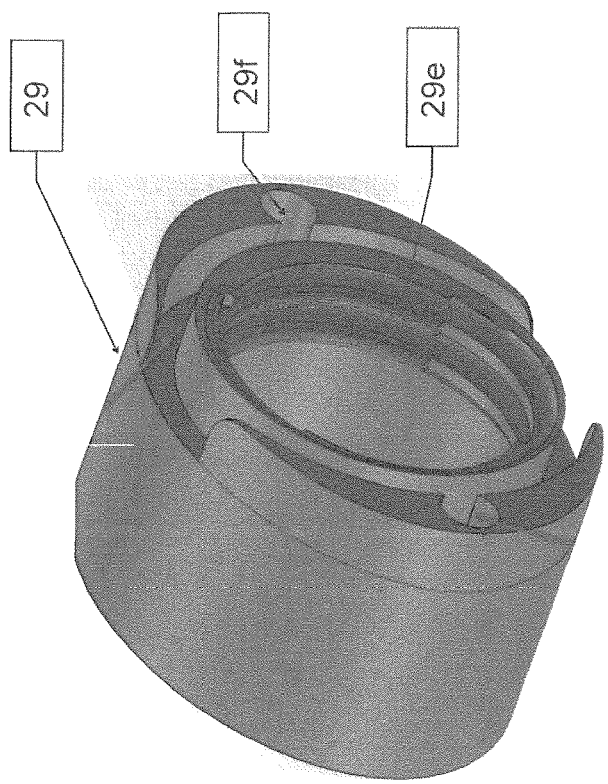
FIG. 6 is a detailed proximal end perspective view of a vacuum foot portion of the outer sheath of a device in accordance with one embodiment of the present invention.

FIG. 6 is a detailed proximal end perspective view of a vacuum foot portion of this embodiment of the present invention. FIG. 6 shows circular opening or channel 29*e* for mounting to outer spring 72. Threaded feature 29*e* in the proximal end of outer suction foot portion 29 is provided to engage electrocautery spring (not shown).

FIG. 6 also shows two opposing vacuum hose attachments 29*f* that are provided to connect the vacuum air hose or tubing 14 as shown in FIG. 3.

FIG. 7 is a detailed first lateral elevation view of a proximal end manifold bulkhead 18 housing of a device in accordance with the displayed embodiment of the present invention. FIG. 7 shows four articulation wire outlets 18*a* 18*d*, with articulation wire outlets 18*a* and 18*b* positioned to accept articulation wires controlled by pulley knob 82 as the articulation knob to be rotated to bring about and control side-to-side articulation, and articulation wire outlets 18*c* and 18*d* positioned to accept articulation wires controlled by spool knob 19 as the articulation knob to be rotated to bring about and control side-to-side articulation.

FIG. 7 also shows two vacuum hose attachment apertures 18*e* and 18*f* that communicate with vacuum air hoses or tubing, such as vacuum air hose or tubing 4. FIG. 7 also shows electrocautery aperture 29 that functions as throughhole for passage of electrocautery connector.

FIG. 8 is a sectioned distal perspective view of a proximal end manifold bulkhead 18 housing of a device of the displayed embodiment of the present invention. FIG. 8 also shows two articulation knob/spool cavities 18*h* and 18*i* that accept and permit rotation of pulley knob 82 and spool knob 19, respectively. FIG. 8 also shows cavity 18*j* for passage of the vacuum-to-vacuum hose attachment apertures 18*e* and 18*f*; and which in turn communicate with attachment point 18*k* for vacuum connector.

FIG. 9 is a partially sectioned and transparent lateral view of a proximal end manifold bulkhead 18 housing of the displayed embodiment of the present invention. FIG. 9 shows routing cavity 18*l* for articulation wires actuated by pulley knob 82, and routing cavity 18*m* for articulation wires actuated by spool knob 19.

FIG. 10 is a partially sectioned perspective view of an articulation control knob and spool of a device in accordance with the displayed embodiment of the present invention. FIG. 10 shows pulley knob 82 and the cutout feature on underside of pulley knob 82 to engage spool having upper spool area 82*a* and aperture 82*b* for attachment of an articulation wire (such as by feeding through and knotting), and lower spool area 82*c* and aperture 82*d* for attachment of an articulation wire (such as by feeding through and knotting).

FIG. 11 is a partially sectioned perspective view of an articulation control knob and spool positioned on a proximal end housing of a device in accordance with one embodiment of the present invention.

FIG. 11 shows lip portion 82*e* of pulley knob 82 to engage the corresponding end feature of proximal end manifold bulkhead 18 housing to prevent knob pull-out during operation.

FIG. 12 is a top perspective view of an articulation control knob, such as pulley knob 82, of a device in accordance with this embodiment of the present invention.

FIG. 12 shows an assembled pulley knob 82 (i.e., made of two handle halves and a spool portion), an adhesive being used to adjoin the handle halves in engagement with the spool portion.

It will be appreciated that spool knob 19 is engaged with and cooperates with proximal end manifold bulkhead 18 housing in the same fashion as does pulley knob 82.

FIG. 13 is a first perspective partially transparent view of the proximal end of an electrocautery blade subassembly of a device of the displayed embodiment of the present invention. In the displayed embodiment, it shows the electrical pin 40 connection to the handle and the continued electrical connection to the electrocautery blade 48*a* at the distal end via a circular coil and copper plate (slip ring mechanism), such that the electrical contact is maintained as the electrocautery blade 48*a* rotates.

FIG. 13 shows circular copper contact plate 99*b* and knob springs 99*a* that maintain sprung distance between rotational knob cap 41 and copper contact plate 99*b* that in turn bears against float ring 42 (slip ring mechanism), as may be appreciated from FIG. 16.

FIG. 14 is a partially sectioned and transparent first perspective view of the proximal end of an electrocautery blade subassembly of a device in accordance with this particular embodiment of the present invention. FIG. 14 shows rotational knob assembly 22, straight electrocautery sheath 23, electrocautery connector pin 40, rotational knob cap 41, float ring 42 and electrocautery spring 48.

Rotational knob cap 41 can be turned to rotate electrocautery spring 48 and the electrocautery blade 48*a* it bears; and advance it longitudinally through threaded feature 29*e* in the inner side of distal end of outer suction foot portion 29*a*. This threaded feature is provided to engage electrocautery spring, as shown in FIG. 6, to permit it to be urged forward to make a circular cutting movement in a reliable and regulated fashion as it is rotated to extend beyond the inner and outer suction feet when in a parallel position.

Figure 15:
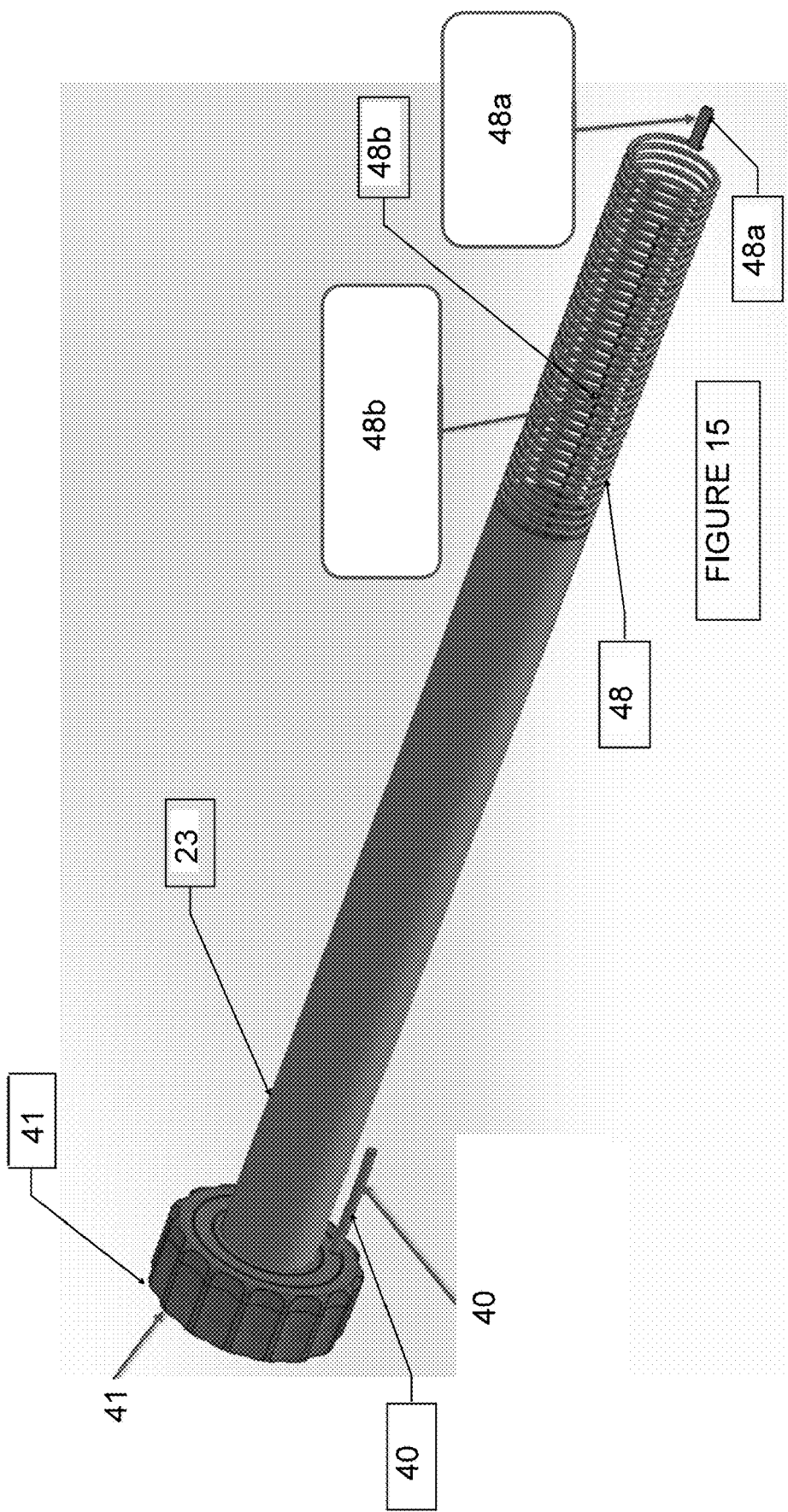
FIG. 15 is a first perspective view of the distal end of an electrocautery blade subassembly of a device, in accordance with one embodiment of the present invention.

FIG. 15 is a first perspective view of the distal end of an electrocautery blade subassembly of a device, in accordance with the displayed embodiment of the present invention. FIG. 15 shows various additional operational features of the electrocautery blade subassembly. FIG. 15 shows that rotational knob cap 841 can be spun to rotate electrocautery spring 48 and associated electrocautery cutter and advance 48*a* longitudinally through threads provided in the suction foot 29 as shown in FIG. 6.

Electrocautery connector pin 40 routes through outer vacuum handle and plugs into adapter on sheath handle.

The electrocautery wire 48*b* thus delivers electrical signal from handle 4 to spring 48/cutter blade 48*a* assembly as shown and described in detail in FIGS. 16 and 17.

FIG. 16 is a detailed sectioned first perspective view of the distal end of an electrocautery blade subassembly of a device in the displayed embodiment of the present invention. This Figure shows the partially sectioned proximal end of the electrocautery assembly. In the displayed embodiment, it shows the electrical pin 40 connection to the handle 4 and the continued electrical connection to the electrocautery blade at the distal end via a circular coil and plate (slip ring mechanism), such that the electrical contact is maintained as the electrocautery blade rotates.

FIG. 16 elucidates that rotational knob cap 41 is assembled by attachment of rotational knob cap bottom closure ring 41*a* that is adhered to rotational knob cap 41 to capture float ring 42 and copper contact plate 99*b* (slip ring mechanism), such that float ring 42 and electrocautery connector pin 40 can rotate freely relative to the balance of the rotational knob assembly 22.

Electrocautery connector pin 40 extends through rotational knob cap bottom closure ring 41*a* of rotational knob assembly 22, and plugs into corresponding adapter on the rotational knob cap 41.

The electrocautery cutter blade 48*a* is welded onto electrocautery spring 48 such that cutter blade 48*a* performs cutting.

Knob springs 99*a* ensure constant contact between circular copper contact plate 99 and electrocautery connector pin 40.

FIG. 16 also shows that an adhesive is used to join knob cap 41 to knob 22, lock in float ring 42, and that the straight electrocautery sheath 23 is fixed relative to rotational knob cap 41.

The electrocautery wire 48*b* is soldered to circular copper contact plate 99*b*.

Electrocautery connector pin 40 is in contact with circular copper contact plate 99*b* which contact is maintained by knob springs 99*a*.

FIG. 17 is a detailed perspective view of the distal end of an electrocautery blade subassembly of a device in accordance with one embodiment of the present invention. FIG. 17 shows electrocautery wire 48*b* attached to electrocautery spring 48 through a conductive epoxy. The electrocautery spring 48 is provided with a flat notch for placement of the weld to attach the electrocautery cutter blade 48*a*.

FIG. 18 is a partially sectioned distal end perspective view of the distal end of an inner vacuum subassembly of a device in this embodiment of the present invention. FIG. 18 shows adapter 15 and its engagement with inner circular suction foot 62.

FIG. 19 is a partially transparent perspective view of an inner vacuum subassembly of a device, with vacuum connector, in accordance with this embodiment of the present invention. FIG. 19 shows inner sheath straight tube 114, inner circular suction foot 62, inner proximal end manifold bulkhead 17, inner vacuum position lock 111, inner air hose 12, floating inner port 13, inner vacuum proximal end cap 14 and inner vacuum connector 91.

Inner sheath straight tube 8114 has two inner air hoses 12 extending from the inner proximal end manifold bulkhead 17. The two inner air hoses 12 supply vacuum pressure to the inner circular suction foot 62 through adapter 15. The vacuum area 62a of inner circular suction foot 62 secures the device to tissue at a target site. FIG. 19 also shows the distal tubular part is flexible and articulating compared to the proximal tubular part that is rigid.

FIG. 20 is a partially sectioned and transparent distal end perspective view of the distal end of an inner vacuum subassembly of a device in accordance with the displayed embodiment of the present invention.

FIG. 20 shows various additional operational features of the inner vacuum subassembly. As shown in FIG. 20, the vacuum lines of the two inner air hoses 12 may be disposed so as to act as a rail for lead holder shown in FIG. 24.

Adapter 15 ensures smooth transition from vacuum line 12 to inner circular suction foot 62 whose vacuum area 62b secures device to the tissue at the target site.

FIG. 21 is a partially transparent perspective view of an inner vacuum subassembly of a device, with vacuum connector, in accordance with this embodiment of the present invention, and shows various additional operational features of the inner vacuum subassembly.

FIG. 21 shows floating inner port 13 piece, within inner proximal end manifold bulkhead 17 and enclosed by inner vacuum proximal end cap 14, allows for longitudinal movement of vacuum lines 12 during articulation, and shows that the port passes vacuum from inner vacuum connector 91 (in this embodiment ¼" OD connector to the handle, and to the tubing of inner air hose 12 that supplies vacuum pressure to end effector, to vacuum area 62b of the inner circular suction foot 62.

The inner vacuum position lock 111 holds position of lead driver (described in FIGS. 24-27) until the operator is ready to attach lead.

Locking tabs 62a hold position of inner vacuum foot 62 relative to the outer oval suction foot 29 until inner vacuum foot 62 is rotated with respect to oval suction foot 29, as described in FIGS. 49 and 50.

FIG. 21 also shows that inner sheath straight tube 14 may be provided with cutouts 14a to allow for articulation flexibility during use.

Figure 22:
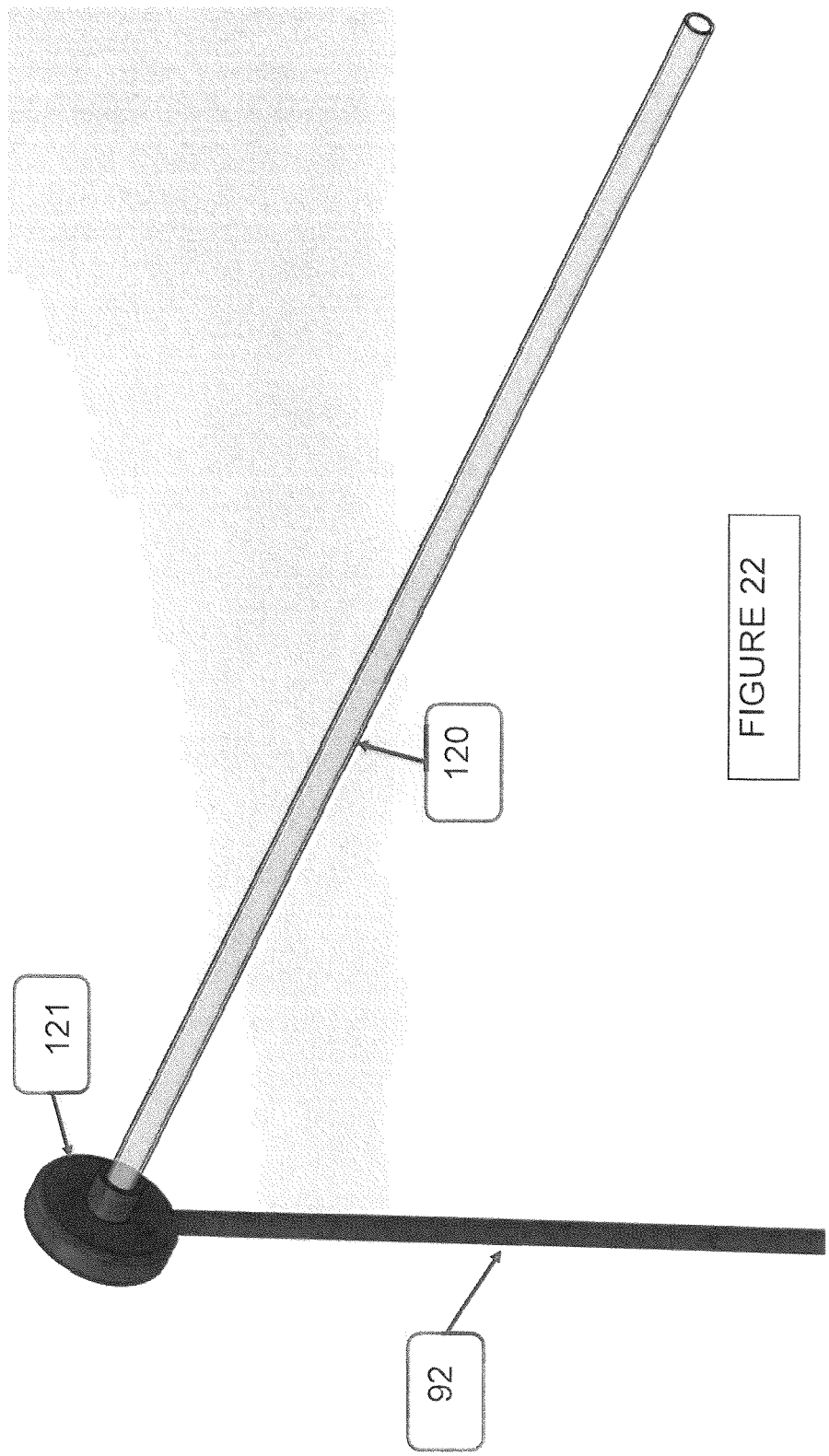
FIG. 22 is a partially transparent perspective view of a tissue or waste removal vacuum subassembly of a device, with vacuum connector, in accordance with one embodiment of the present invention.

FIG. 22 is a partially transparent perspective view of a tissue remover vacuum subassembly of a device, with associated vacuum connector, in accordance with the displayed embodiment of the present invention. FIG. 22 shows tissue remover vacuum tube 120, its tissue remover handle 121 and tissue remover vacuum connector 92.

Figure 23:
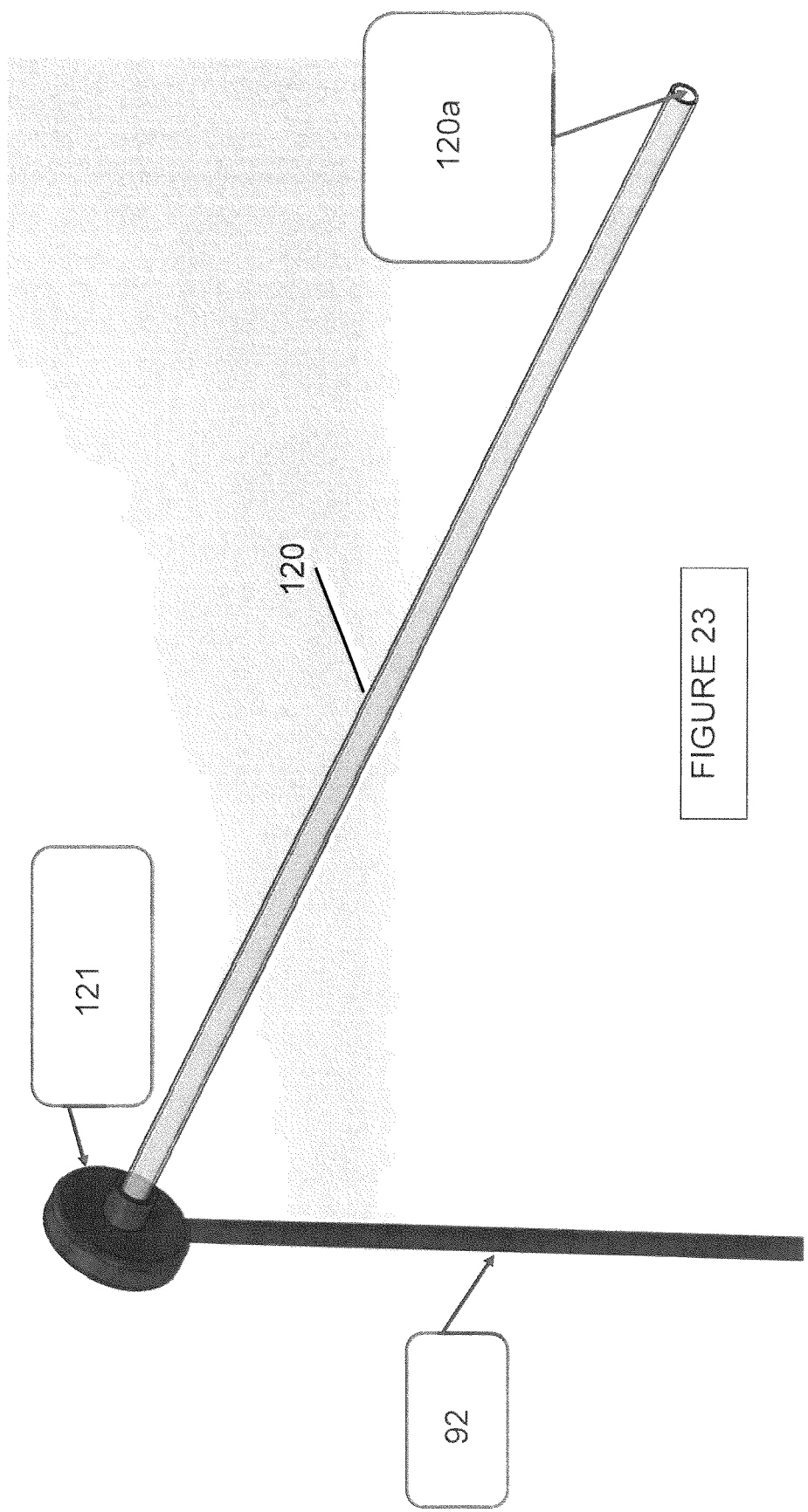
FIG. 23 is a partially transparent perspective view of a tissue remover vacuum subassembly of a device, with vacuum connector, in accordance with one embodiment of the present invention.

FIG. 23 is a partially transparent perspective view of a tissue remover vacuum subassembly of a device, with vacuum connector, in accordance with one embodiment of the present invention, and shows various additional operational features of the tissue remover vacuum subassembly.

FIG. 23 shows that the tissue remover handle 121 conducts the vacuum from the tissue remover vacuum connector 92 (in this embodiment a ¼" OD connector to handle) to the tissue remover vacuum tube 120 which in this embodiment has a ¼" diameter area and sufficient length with respect to the length of the inner sheath straight tube 114 into which it is extended during use, to provide suction to the terminal end 120a to be applied to the pericardial tissue for removal after cutting.

Figure 24:
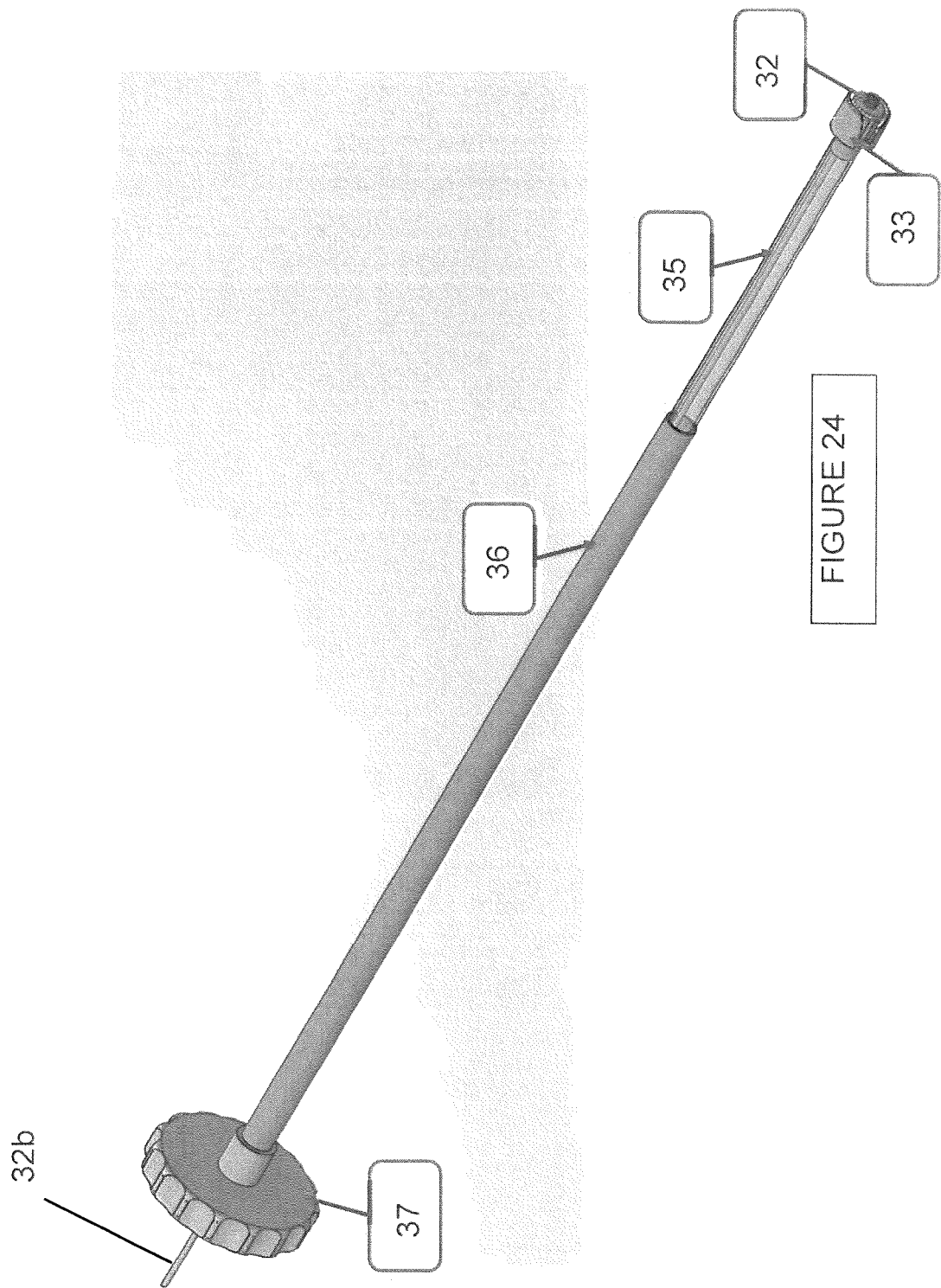
FIG. 24 is a partially sectioned and transparent distal end perspective view of the lead drive subassembly of a device in accordance with one embodiment of the present invention.

FIG. 24 is a partially sectioned and transparent distal end perspective view of the proximal end of a lead drive subassembly of a device in accordance with the displayed embodiment of the present invention.

FIG. 24 shows lead 32, lead wire 32b, lead holder 33, lead drive tube (flexible) extension 35, and lead drive main (relatively stiff) tube 36 and lead drive knob 37.

FIG. 25 is a partially sectioned and transparent distal end perspective view of the proximal end of a lead drive subassembly of a device in accordance with the displayed embodiment of the present invention, and shows various additional operational features of the lead drive subassembly.

FIG. 25 shows that lead drive knob 37 is used to advance the lead 32, and to rotate it to screw the lead 32 into the tissue at the target site.

The relatively stiff lead drive main tube 36 permits easier insertion and rotation of the lead 32 extending from the lead head 32a, while the relatively flexible lead drive tube extension 35 permits the operator to conform to the articulated shape and path provided by the flexible distal portion of the inner vacuum conduit straight tube 114 (that, for instance may be articulated at its distal end, such as by the provision of cutouts 114a, or the use of a relatively flexible material).

FIG. 26 is a distal end elevation view of the distal end of a lead drive subassembly of a device in accordance with the displayed embodiment of the present invention. FIG. 26 shows lead holder outer wall 33a that supports folded lead wire.

Cutouts, such as opposed cutouts 33b in lead holder 33, ride along the tubular shapes of tubes 12 of the inner vacuum conduit, during insertion of the lead drive main tube 36.

FIG. 27 is a distal end lateral perspective view of the distal end of a lead drive subassembly of a device in accordance with the displayed embodiment of the present invention. FIG. 27 shows lead holder inner walls 33c that serve to pinch lead 32 in lead head 32a to hold it in place during insertion.

Figure 65:
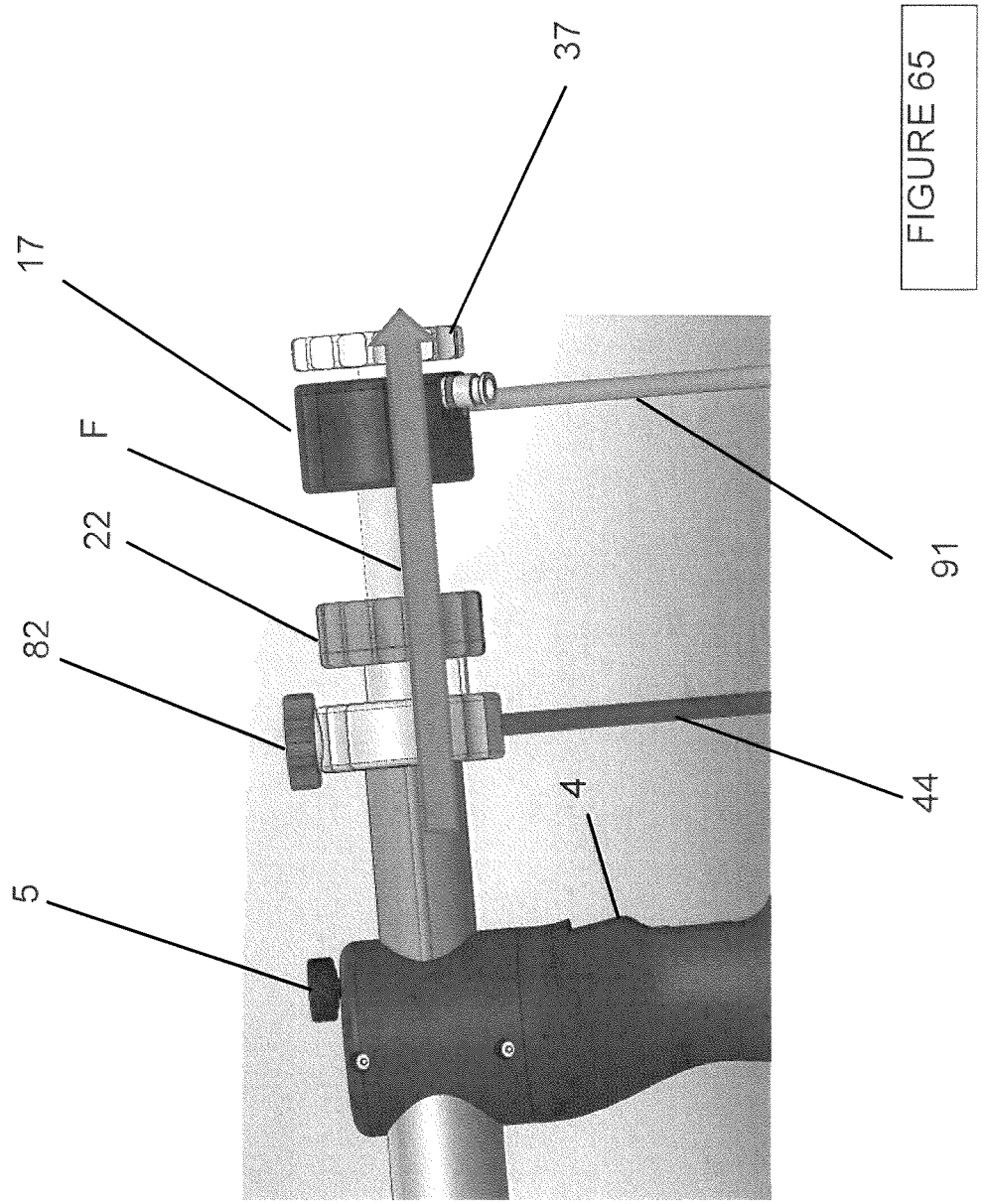
FIG. 65 is a detailed first lateral elevation view of the proximal end of an outer and inner vacuum conduit handle and lead drive assembly of a device in accordance with one embodiment of the present invention.

As to the procedure for using the device of the present invention and otherwise to practice its method, the following steps may be used:

In order to prepare and use the device of the present invention as exemplified by the embodiment shown in FIGS. 1-65, the following procedure may be used as described stepwise by reference to FIGS. 28-65.

Figure 28:
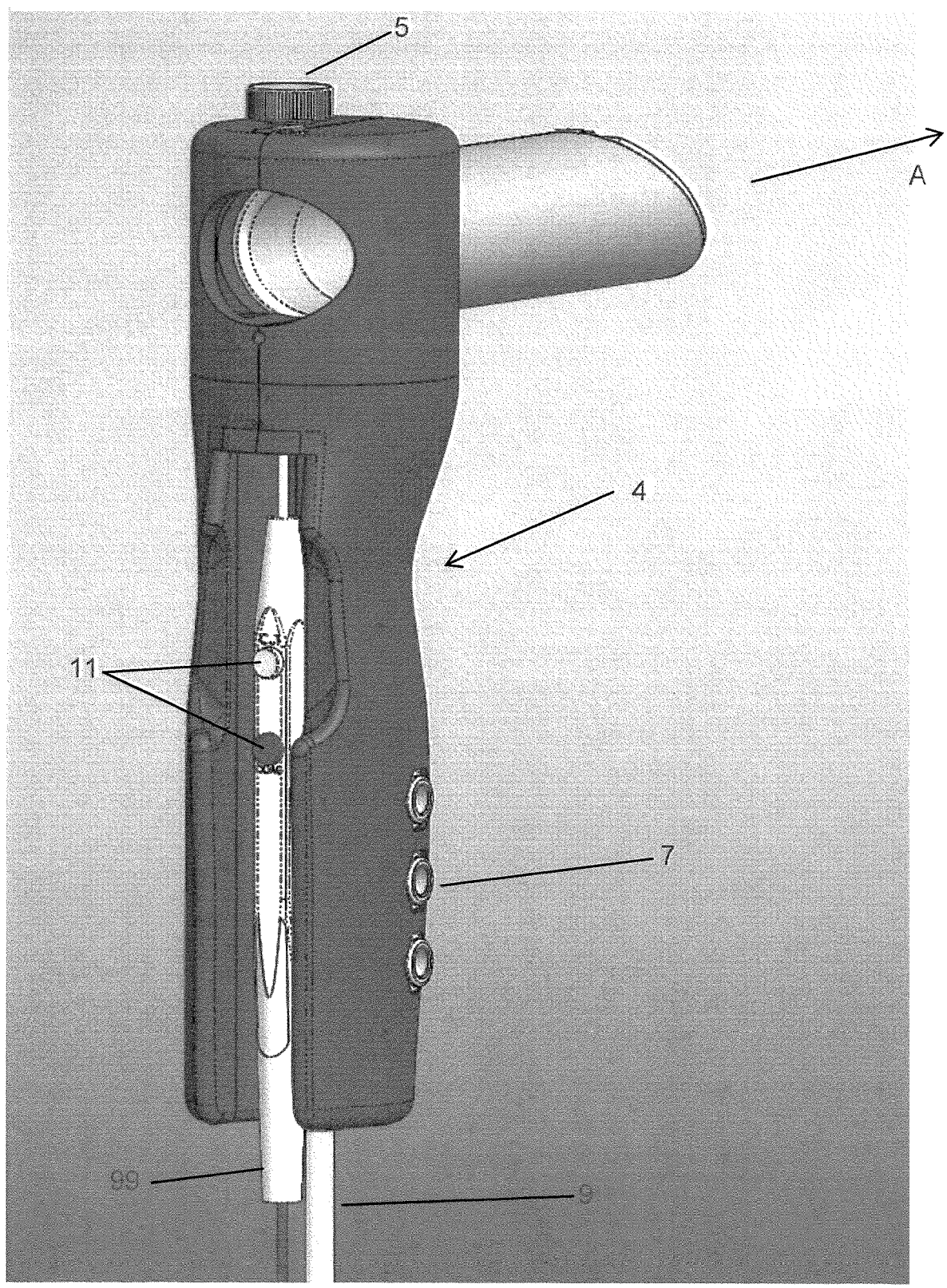
FIG. 28 is a proximal end lateral perspective view of an elongated handle sheath subassembly for a device in accordance with one embodiment of the present invention.

Referring to FIG. 28, the electrocautery (EC) pencil switch is inserted into device handle 4, by plugging it, through connector wire 97, into the embedded connector 98. The device handle tubing is attached to wall suction in the medical treatment suite or operating room through connector 90.

Figure 29:
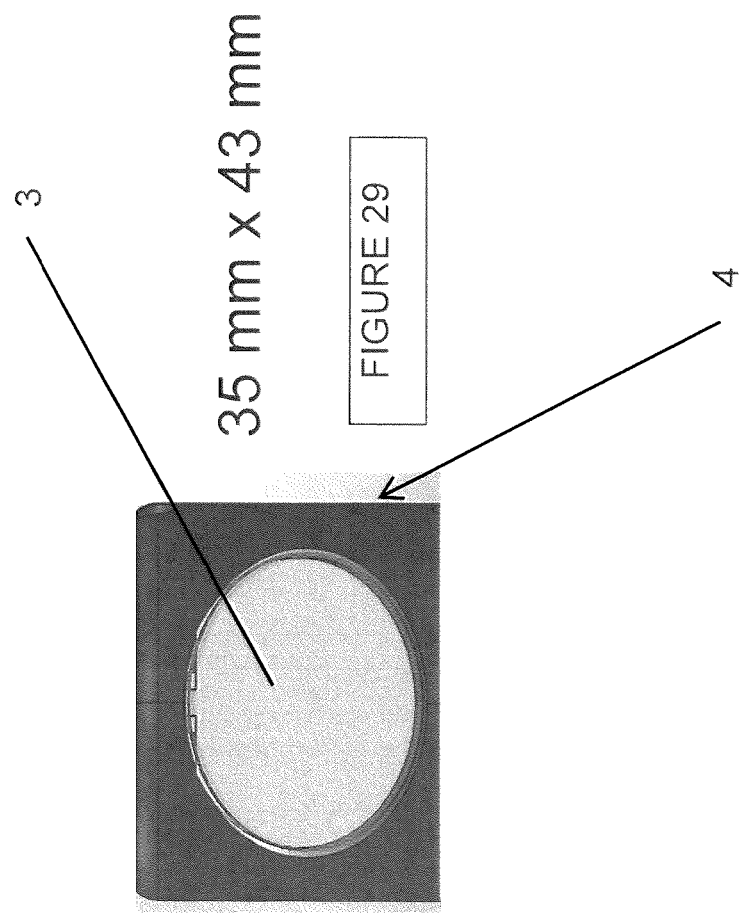
FIG. 29 is a distal end partial elevation view of an elongated handle sheath subassembly for a device in accordance with one embodiment of the present invention.

Referring to distal end view of the device in FIG. 29 showing cover piece 3 and handle 4, an access incision is first made in the left chest wall, with a 3 to 4 cm diameter maximum (e.g., 35 mm×43 mm). The left lung is then decompressed and collapsed, thereby exposing the pericardial sac, such as by using the standard thoracoscopic, single lung ventilation technique.

Figure 30:
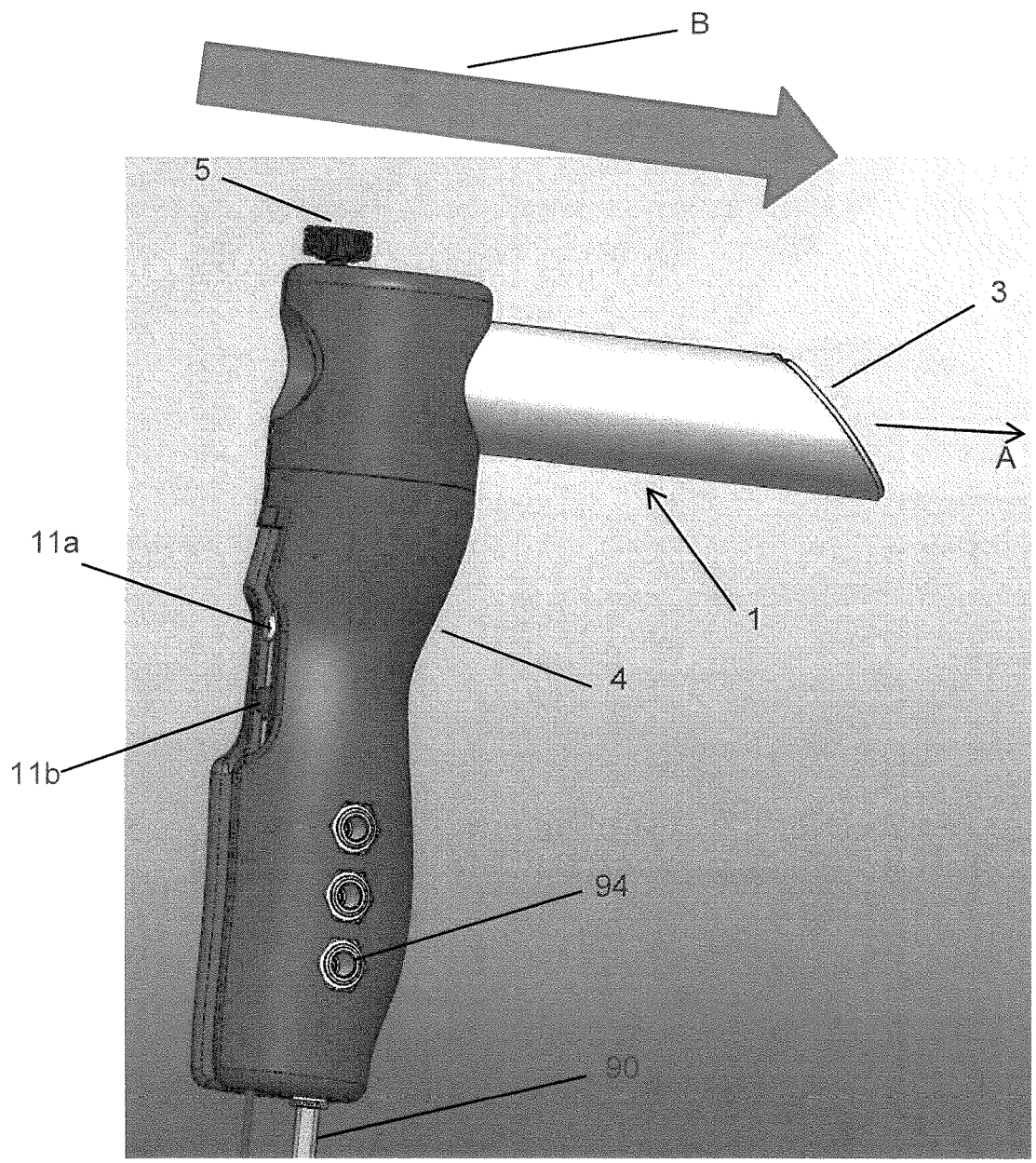
FIG. 30 is a lateral perspective view of an elongated handle sheath subassembly for a device in accordance with one embodiment of the present invention.

As may be appreciated with reference to FIG. 30, the support sheath 1 is then inserted by passing its distal end through the chest wall via the access along insertion direction B.

Figure 31:
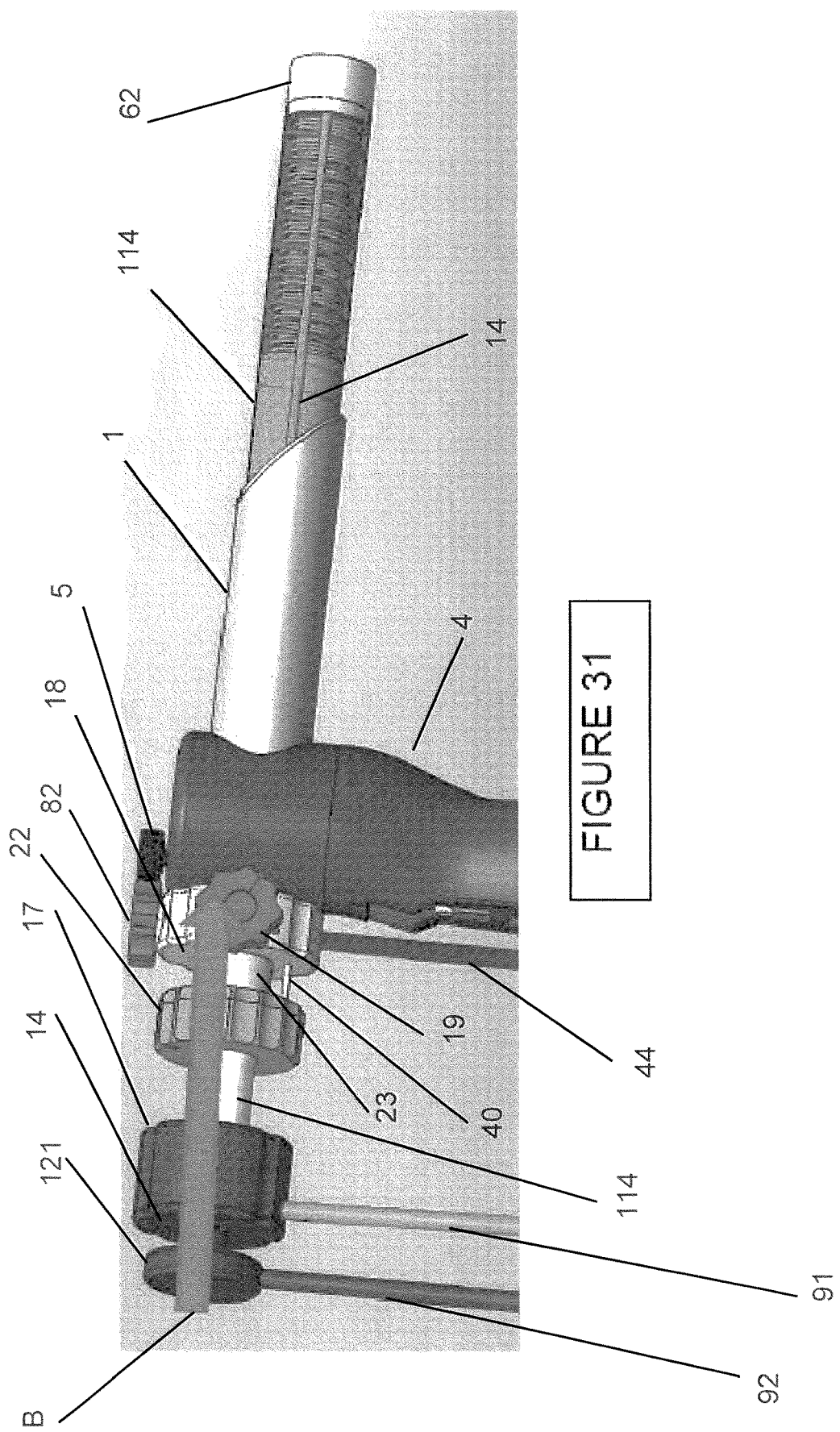
FIG. 31 is a partially transparent partial lateral perspective view of an elongated handle sheath with the outer vacuum conduit, electrocautery knife, inner vacuum conduit and tissue or waste removal vacuum conduit subassembly for a device in accordance with one embodiment of the present invention.

As shown in FIG. 31, the co-engaged outer vacuum assembly, electrocautery subassembly, inner vacuum subassembly, and waste or tissue removal tubes are urged through the sheath 8071 [1] as a unitary assembly unit.

Figure 32:
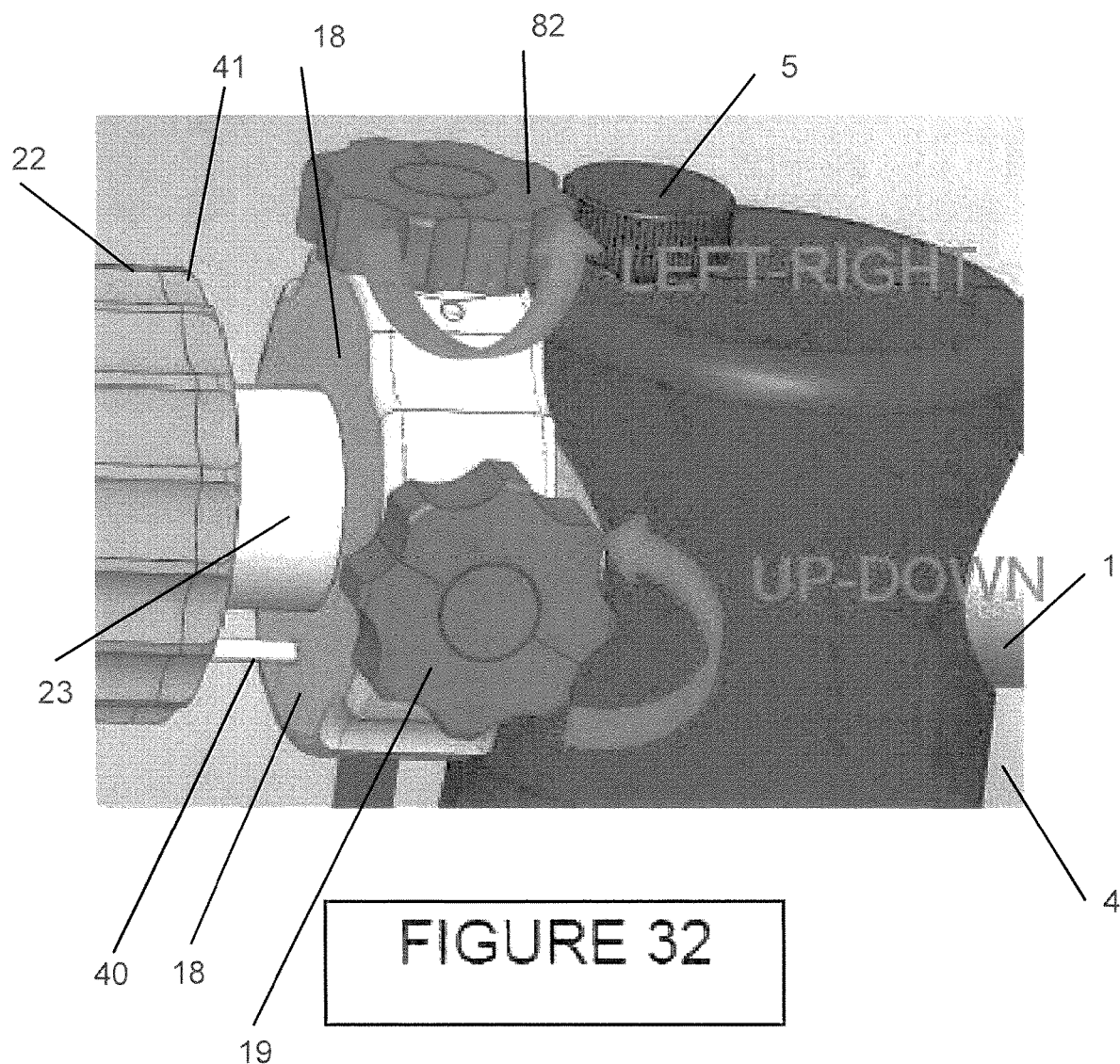
FIG. 32 is a detailed partial lateral perspective view of an elongated handle sheath with outer and inner vacuum conduits subassembly with control knobs for a device in accordance with one embodiment of the present invention.

Referring to FIG. 32, the spool knob 19 may be rotated to provide side-to-side articulation, and articulation pulley knob 82 may be rotated to provide up-down articulation, to position the distally facing faces or surfaces of the inner circular suction foot 62 and outer suction foot portion 29 with respect to the target site.

The distal ends of the coterminously positioned inner and outer vacuum conduits, respectively inner sheath straight tube 114 and inner sleeve 73/mesh sleeve 74 (i.e., presenting respectively inner circular suction foot 62 and outer suction foot portion 29), are urged through the support sheath 1, opening the spring biased cover 3 of the introducing distal end 2 of the sheath 1.

Figure 33:
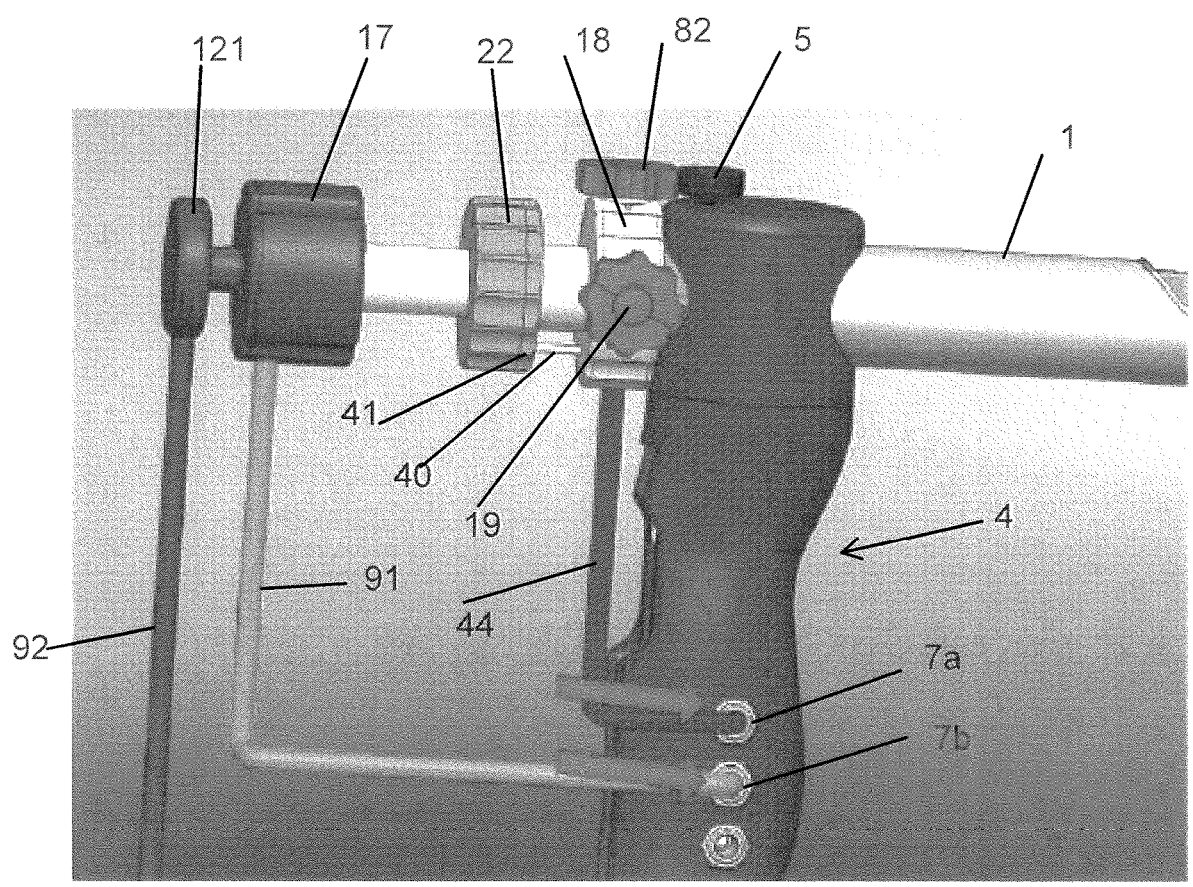
FIG. 33 is a detailed partial lateral perspective view of an elongated handle sheath with the outer vacuum, electrocautery, inner vacuum and waste or tissue removal vacuum conduit subassembly with control knobs for a device in accordance with one embodiment of the present invention.
Figure 34:
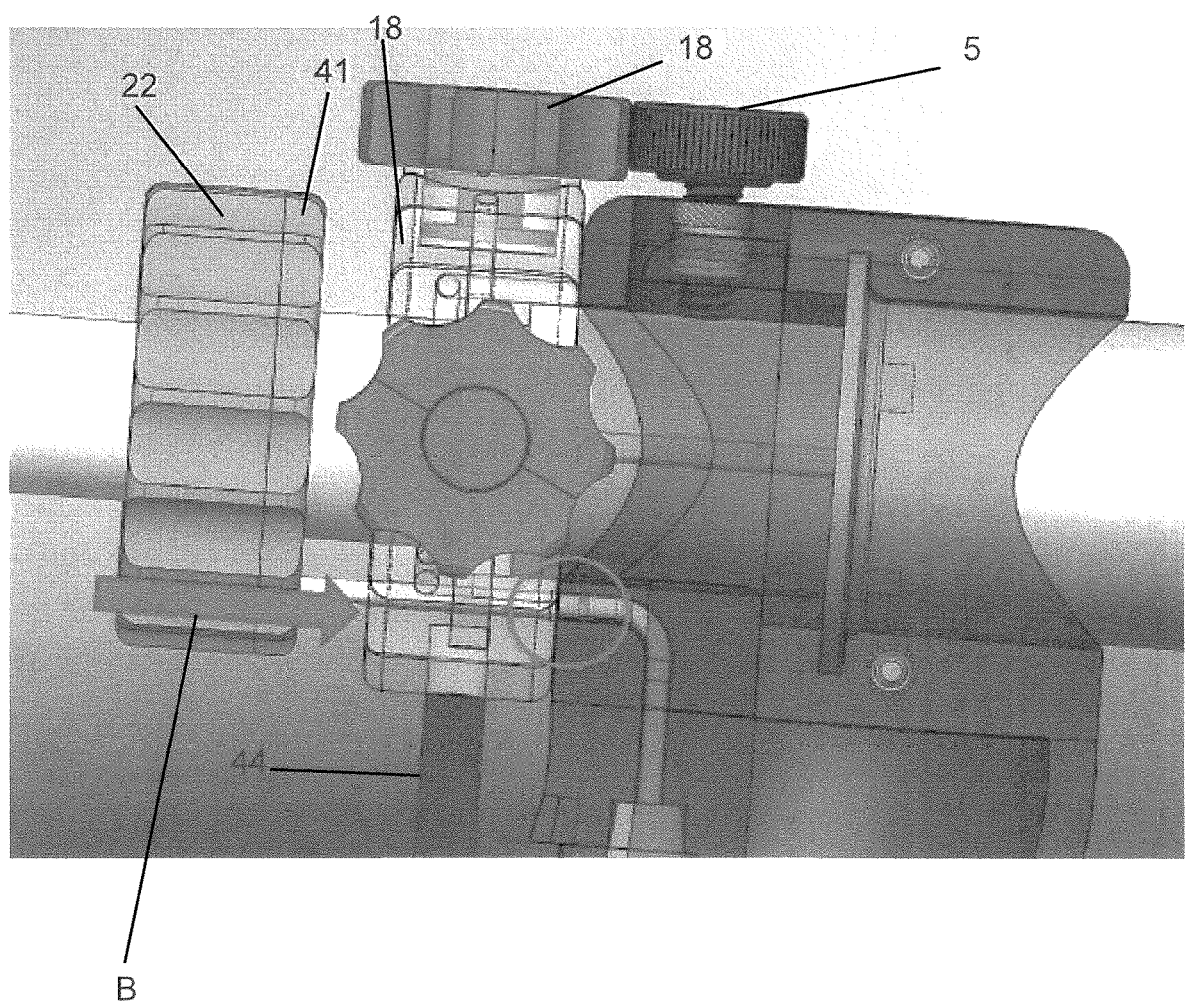
FIG. 34 is a detailed partially sectioned and transparent partial lateral elevation view of an elongated handle sheath with outer and inner vacuum conduits subassembly with control knobs for a device in accordance with one embodiment of the present invention.

As may be appreciated with reference to FIGS. 33 and 34, the inner and outer vacuum connectors 91 and 44 are inserted into the vacuum ports 7a and 7b respectively in device handle 4 to turn on the vacuum suction.

Using rotational knob 22 and cap 41 of the straight electrocautery sheath 23 and the device handle 4, slight traction is brought to the device.

As shown in FIG. 34, the electrocautery knob 22 and cap 41 is urged forward to ensure connection with device handle 4 (with electrocautery connector pin 40 extending through outer proximal end manifold bulkhead 18 of the device), in which case the electrocautery spring 80/18 will compress, such that the electrocautery blade 48a will not move forward.

Making reference to FIGS. 35-37, the switch in handle 4 is operated so as to rotate electrocautery knob counterclockwise (CCW) ~1.25 rotations, such that the electrocautery blade 48a will translate forward 3 mm with each rotation in the displayed embodiment.

As shown in FIGS. 39-41, the electrocautery rotational knob 22 and cap 41 is rotated clockwise (CW) >360° to translate electrocautery blade 48a back to starting position, as shown in FIGS. 40-41.

As shown in FIGS. 42-44, the tissue remover vacuum connector 92 of the tissue removal assembly is connected to its vacuum source via port 7c, and its handle 121 are advanced flush to inner vacuum proximal end cap 14, to secure and remove cut tissue with vacuum suction.

FIGS. 43 shows the step of disconnecting the inner vacuum connector 91 from port 7b in device handle 4 to turn off suction to the inner vacuum assembly comprising generally parts 14, 17, 62 and 114.

As shown in FIG. 44, the tissue removal assembly comprising generally parts 14, 17, 62 and 114 is withdrawn completely from the device to discard the cut pericardial tissue.

As shown in FIGS. 45-47, the lead holder 33 with opposed cutouts 33b are aligned with the vacuum line rails 12 by inserting it into floating inner port 13, such that opposed cutouts 33b in lead holder 33, ride along inner vacuum tubes 12 during insertion, and insert the lead drive assembly up to position lock.

Referring to FIG. 48, the inner vacuum is then turned on.

As shown in FIGS. 49 and 50, inner vacuum assembly is then rotated approximately 70° counterclockwise (CCW) to align keyhole formed by locking tab 29c in the oval suction foot 29 as indicated by the oval lines superimposed over FIGS. 49 and 50.

As shown in FIGS. 51 and 52, inner vacuum assembly comprising generally parts 14, 17, 62 and 114 is advanced to target site by advancing inner sheath straight tube 4114 bearing inner circular suction foot 62 (i.e., lead drive main (relatively stiff) tube 36 with lead drive tube (relatively flexible) extension 35 bearing lead holder 33/lead head 32a/lead 32, through use of lead drive knob 37). This causes inner circular suction foot 62 and lead holder 33/lead head 32a/lead 32 to be advanced beyond oval suction foot 29, as shown in FIG. 53, so as to urge lead driver against left ventricular wall.

Referring to FIGS. 54 and 55, the operator may then test sensing and pacing parameters by contact of the lead 32 to different positions to establish a final lead insertion point. At this point, the inner vacuum position lock 11 may be disengaged 1a rotating it counterclockwise as shown, to permit lead holder 33/lead head 32a/lead 32 to be advanced beyond inner circular suction foot 62.

As shown in FIGS. 56-58, the operator may attach the lead 32 to heart wall by rotating lead drive knob 37 clockwise 3 full rotations.

Referring to FIGS. 59 and 60, the operator may then pull lead drive (i.e., lead drive main (relatively stiff) tube 36 with lead drive tube (relatively flexible) extension 35 bearing lead holder 33) back 5 mm (as indicated by direction arrow D) to release lead 32 with lead head 32a from lead holder 33. At this point the inner vacuum suction may be turned off by removing green inner vacuum connector 91 from port 7b in device handle 4.

As shown in FIGS. 61-64, the lead driver and inner vacuum assembly components are withdrawn to their original position by withdrawing inner sheath straight tube 114 bearing inner circular suction foot 62 has indicated by direction arrow E) to a concealed position within oval outer suction foot 29 (comparing associated positions of FIGS. 61 and 62 with that of FIGS. 63 and 64).

Referring to FIGS. 65, this Figure shows the device in the last steps of the procedure including: turning off the vacuum suction for outer vacuum by removing blue outer vacuum connector from the device handle 4 (i.e., from port 7a); twist spool knob 19 and pulley knob 82 on outer proximal end manifold bulkhead 18 to return device to un-articulated alignment; and fully retract outer vacuum, electrocautery, inner vacuum, and lead holder assemblies (as indicated by direction arrow F).

A summary of an example of a PLAD procedure is presented as follows:
1. Make access in left chest wall
2. Circular or oblong:
   i. 3 cm dia. maximum
   ii. 3 cm×4 cm maximum
3. Decompress/collapse left lung thereby exposing pericardial sac (Standard thoracoscopic, single lung ventilation technique)
4. Pass distal end of sheath through chest wall via access
5. Push distal end of the outer and relatively inner vacuum tubes through sheath with the waste removal vacuum tube resident therein, opening the spring biased cover of the introducing sheath
6. Position faces of outer and relatively inner vacuum feet on pericardium by rotating articulation knob A
7. Tighten set screw on the support sheath for outer vacuum tube 8. May rotate sheath around its long axis for fine positioning
9. Turn on vacuum for outer, inner and waste removal vacuum tubes via stop cocks on all three heads respectively
10. Using handle of sheath, place slight traction to pull the yielding pericardium away from the subjacent myocardium or heart muscle
11. Push Electrocautery knob to position 2
12. Rotate Electrocautery knob>360 degrees thereby cutting pericardium held captive between outer and inner suction ring
13. Cut piece of pericardium held by relatively inner vacuum foot and by waste removal vacuum conduit
14. Pull Electrocautery knob back to position 1
15. Turn off suction in the relatively inner vacuum tube and remove waste removal vacuum conduit (with the held piece of cut pericardial tissue)
16. Turn off vacuum to waste removal vacuum conduit
17. Remove cut pericardial tissue
18. Remove spacer A from relatively inner vacuum tube
19. Load lead and drive assembly into relatively inner tube until drive assembly contacts position lock
20. All this time, the outer vacuum foot is still attached to the pericardium with suction, keeping it taut and splayed with a central hole
21. Position relatively inner vacuum foot against left ventricular wall through the pericardial hole created in Step 9
22. Second plane of plane of articulation possible by rotating articulation knob B
23. May rotate relatively inner vacuum tube along its long axis for fine positioning
24. Turn on vacuum for relatively inner vacuum tube
25. Loaded Lead is positioned inside relatively inner suction tube in such a way that it is in touch with myocardium with the distal end of the pacer lead screw
26. Test sensing and pacing parameters
27. Disengage position lock for drive
28. Attach lead to heart wall by rotating drive clockwise while applying slight axial force
29. Test sensing and pacing parameters
30. Withdraw lead drive
31. Turn off vacuum for relatively inner vacuum tube
32. Remove relatively inner vacuum tube in a direction axial to lead (to prevent dislodgement of lead) by simultaneously relaxing articulation and withdrawing relatively inner vacuum tube from outer vacuum conduit
33. Turn off vacuum for outer vacuum conduit
34. Remove outer vacuum conduit tube in a direction axial to the lead (to prevent dislodgement of lead, if used) by simultaneously relaxing articulation and withdrawing outer vacuum conduit and sheath together from chest cavity
35. The proximal end of the lead can now be channeled and connected with the pacemaker/defibrillator device
36. Close access site From this point, the balance of the surgical operation and energizes of the pacing lead made be completed in accordance with methods and apparatus known and used in the art.

It will be appreciated that the mechanical arrangements in the device and the logical order of the steps in the described methods are used for purposes of illustration only, and that the steps may be varied where not otherwise inconsistent with the purpose and result obtained in the practice of the invention.

It will be also be appreciated that the mechanical arrangements in the device include their individual subassemblies and elements thereof and that the steps of the method include individual steps and series of steps within subroutines of the methods as described.

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description of which the claims are to be read as a portion thereof, and all changes that come within the meaning and range of equivalency of the claims are intended to be embraced therein.

The present invention may be used in accordance with other methods and devices relating to lead and conduit placement, such as those described in the following references that are hereby incorporated herein by reference:

| References |
|---|
| 4146037 |
| 4271846 |
| 4972847 |
| 5139033 |
| 5203772 |
| 5342413 |
| 5882333 |
| 5902331 |
| 5972013 |
| 6132456 |
| 6697677 |
| 6868291 |
| 7270669 |
| 7526342 |
| 7544197 |
| 7890192 |
| 7930040 |
| 9623236 |
| 9656062 |
| 9675799 |
| 9987484 |
| 9987485 |
| 10039919 |
| 10118031 |
| 10328243 |
| 10524817 |
| 10525262 |
| 20030187461 |
| 20030187461 |
| 20040153098 |
| 20040215139 |
| 20050004644 |
| 20060009827 |
| 20060161238 |
| 20090182347 |
| 20090198251 |
| 20100312256 |
| EP452278 |
| WO2004058326 |
| WO2008058265 |
| WO9906104 |

What is claimed is:

1. A device adapted for the thoracoscopic placement of a pacing contact at a target site on an epicardial surface of a heart, the device comprising:
   (a) an inner tubular vacuum conduit having an inner vacuum conduit distal end comprising an inner suction foot portion, said inner tubular vacuum conduit having a flexible distal end and adapted to conduct a vacuum to said inner suction foot portion;
(b) an outer tubular vacuum conduit having an outer vacuum conduit distal end comprising an outer suction foot portion, said outer tubular vacuum conduit having a flexible distal end and adapted to conduct a vacuum to said outer suction foot portion,
said inner tubular vacuum conduit slidingly engaged within outer tubular vacuum conduit, so as to permit said inner suction foot portion to be advanced from a position within said outer suction foot portion to a position beyond said outer suction foot portion distal end;
(c) at least one actuator adapted to articulate said outer suction foot portion while said inner suction foot portion is disposed within said outer suction foot portion;
(d) a waste removal vacuum conduit having a waste removal vacuum conduit distal end, and slidingly engaged within said inner tubular vacuum conduit so as to permit said waste removal vacuum conduit distal end to be advanced to said inner suction foot portion distal end;
(e) an electrocautery blade extensible from between said inner suction foot portion and said outer suction foot portion;
(f) a support sheath for supporting said vacuum conduits, and having a proximal end and a distal end, with respective proximal end inlet and distal end outlet; and
(g) a handle portion extending laterally from said support sheath, said handle portion having a lower portion and an upper portion, and a longitudinal axis, and defining a space adapted to accommodate and support an electrosurgical pencil therein; and (1) an electrosurgical pencil disposed within said space and having an electric input contact extending from said lower portion of said handle, and an electric output contact extending from said upper portion of said handle; (2) a hollow electrocautery sheath extending from said upper portion at an angle to said longitudinal axis, said hollow electrocautery sheath having a rotatable electrocautery connection, and (3) an electrical connection between said electrosurgical pencil and said electric output to said rotatable electrocautery connection.

2. The device of claim 1 wherein handle portion additionally comprising a vacuum manifold comprising valves to supply vacuum to said inner, outer and waste removal vacuum conduits independently.

3. The device of claim 2, additionally comprising a manifold bulkhead disposed on the proximal end of said support sheath, said manifold bulkhead adapted to conduct a vacuum from said vacuum manifold to supply vacuum to said inner, outer and waste removal vacuum conduits independently.

4. The device of claim 1 wherein said relatively inner suction foot portion and said outer suction foot portion each comprise a plurality of air channels.

5. The device of claim 1 wherein said at least one actuator comprise a first actuator and a second actuator, the first actuator comprising a first knob and at least one first tension cord adapted to articulate said outer suction foot portion while said inner suction foot portion and said waste removal vacuum conduit distal end are disposed within said outer suction foot portion; and said second actuator comprises a second knob and at least one second tension cord adapted to articulate said inner suction foot portion when said inner suction foot portion is extended beyond said outer suction foot portion.

6. The device of claim 5, additionally comprising a manifold bulkhead disposed on the proximal end of said support sheath, said manifold bulkhead having said first knob and said second knob disposed thereupon.

7. The device of claim 1 wherein said an inner tubular vacuum conduit is adapted, upon removal of said waste removal vacuum conduit, to slidingly engage a lead guide having a flexible distal portion and a contact head disposed on the distal end thereof, said contact head bearing a pacing lead and adapted to engage said inner suction foot so as to present such that said pacing lead from said inner suction foot, to extend said pacing lead from said inner suction foot.

8. The device of claim 1, additionally comprising a releasable locking mechanism adapted to releasably restrict the axial movement of said inner tubular vacuum conduit with respect to said outer vacuum conduit.

9. The device of claim 1, said distal end portion of said support sheath additionally comprising a moveable cover adapted to reversibly open and close said distal end outlet.

10. The device of claim 1, wherein said inner tubular vacuum conduit is longer than said outer tubular vacuum conduit, and additionally comprising a removable spacer adapted to maintain relatively inner suction foot portion within said outer suction foot portion.

11. The device of claim 1 wherein said electrocautery blade is adapted to be rotated 360 degrees and is energized by a spring biased switch when in an extended position from between said inner suction foot portion and said outer suction foot portion.

12. The device of claim 1, said handle additionally comprising a vacuum manifold comprising valves to supply vacuum to said inner, outer and waste removal vacuum conduits independently.

13. The device of claim 1 additionally comprising a handle portion extending laterally therefrom, said handle portion having a lower portion and an upper portion, said lower portion comprising a vacuum manifold adapted to accept a vacuum connection and to distribute said vacuum to each of said (a) inner tubular vacuum conduit, (b) outer tubular vacuum conduit and (c) waste removal vacuum conduit independently.

14. The device of claim 13, wherein said vacuum manifold comprises three respective push valves governing said vacuum connections to each of said vacuum conduits.

15. The device of claim 1 additionally comprising, on said proximal end of said support sheath:
(a) a proximal bulkhead, and wherein:
 i. a first of said at least one actuator comprises a first captive articulation knob extending into said proximal bulkhead and having a first spool portion having a spool of first articulation wires;
 ii. a second of said at least one actuator comprises a second captive articulation knob extending into said proximal bulkhead and having a second spool portion having a spool of second articulation wires;
said proximal bulkhead comprising:
 i. a first opposed aperture pair having said first articulation wires extending therethrough;
 ii. a second opposed aperture pair having said second articulation wires extending therethrough;
 iii. at least one fluid aperture adapted to transmit a vacuum through said proximal bulkhead;
said outer tubular vacuum conduit extending from said proximal bulkhead a first length;
said inner tubular vacuum conduit of sufficient length so as to be adapted to extend from said proximal bulkhead a second length greater than said first length; and (b) a hollow electrocautery sheath extending from said proximal bulkhead, said hollow electrocautery sheath having a rotatable electrocautery connection, and a spring extending from the distal end of said hollow electrocautery sheath to said electrocautery blade.

16. A device adapted for the thoracoscopic placement of a pacing contact at a target site on an epicardial surface of a heart, the device comprising:
(a) an inner tubular vacuum conduit having an inner vacuum conduit distal end comprising an inner suction foot portion, said inner tubular vacuum conduit having a flexible distal end and adapted to conduct a vacuum to said inner suction foot portion;
(b) an outer tubular vacuum conduit having an outer vacuum conduit distal end comprising an outer suction foot portion, said outer tubular vacuum conduit having a flexible distal end and adapted to conduct a vacuum to said outer suction foot portion,
said inner tubular vacuum conduit slidingly engaged within outer tubular vacuum conduit, so as to permit said inner suction foot portion to be advanced from a position within said outer suction foot portion to a position beyond said outer suction foot portion distal end;
(c) at least one actuator adapted to articulate said outer suction foot portion while said inner suction foot portion is disposed within said outer suction foot portion;
(d) a waste removal vacuum conduit having a waste removal vacuum conduit distal end, and slidingly engaged within said inner tubular vacuum conduit so as to permit said waste removal vacuum conduit distal end to be advanced to said inner suction foot portion distal end;
(e) an electrocautery blade extensible from between said inner suction foot portion and said outer suction foot portion;
(f) a support sheath for supporting said vacuum conduits, and having a proximal end and a distal end, with respective proximal end inlet and distal end outlet; and
(g) a handle portion extending laterally therefrom, said handle having a lower portion and an upper portion, and defining a space adapted to accommodate and support an electrosurgical pencil therein; and an electrosurgical pencil disposed within said space and having an electric input contact extending from said lower portion of said handle, and said lower portion comprising a vacuum manifold adapted to accept a vacuum connection and to distribute said vacuum independently respectively to each of said (a) inner tubular vacuum conduit, (b) outer tubular vacuum conduit and (c) waste removal vacuum conduit.

17. The device of claim 16, additionally a manifold bulkhead disposed on the proximal end of said support sheath, said manifold bulkhead adapted to conduct a vacuum from said vacuum manifold to supply vacuum to said inner, outer and waste removal vacuum conduits independently.

18. The device of claim 16 wherein said at least one actuator comprise a first actuator and a second actuator, the first actuator comprising a first knob and at least one first tension cord adapted to articulate said outer suction foot portion while said inner suction foot portion and said waste removal vacuum conduit distal end are disposed within said outer suction foot portion; and said second actuator comprises a second knob and at least one second tension cord adapted to articulate said inner suction foot portion when said inner suction foot portion is extended beyond said outer suction foot portion.

19. A device adapted for the thoracoscopic placement of a pacing contact at a target site on an epicardial surface of a heart, the device comprising:
(a) an inner tubular vacuum conduit having an inner vacuum conduit distal end comprising an inner suction foot portion, said inner tubular vacuum conduit having a flexible distal end and adapted to conduct a vacuum to said inner suction foot portion;
(b) an outer tubular vacuum conduit having an outer vacuum conduit distal end comprising an outer suction foot portion, said outer tubular vacuum conduit having a flexible distal end and adapted to conduct a vacuum to said outer suction foot portion,
said inner tubular vacuum conduit slidingly engaged within outer tubular vacuum conduit, so as to permit said inner suction foot portion to be advanced from a position within said outer suction foot portion to a position beyond said outer suction foot portion distal end;
said inner tubular vacuum conduit is adapted, upon removal of said waste removal vacuum conduit, to slidingly engage a lead guide having a flexible distal portion and a contact head disposed on the distal end thereof, said contact head bearing a pacing lead and adapted to engage said inner suction foot so as to present such that said pacing lead from said inner suction foot, to extend said pacing lead from said inner suction foot;
(c) a releasable locking mechanism adapted to releasably restrict the axial movement of said inner tubular vacuum conduit with respect to said outer vacuum conduit; and
(d) a waste removal vacuum conduit having a waste removal vacuum conduit distal end, and slidingly engaged within said inner tubular vacuum conduit so as to permit said waste removal vacuum conduit distal end to be advanced to said inner suction foot portion distal end.

* * * * *